(12) United States Patent
Pal et al.

(10) Patent No.: US 11,465,990 B2
(45) Date of Patent: *Oct. 11, 2022

(54) HETEROCYCLIC ANTIESTROGENS

(71) Applicant: SUN PHARMA ADVANCED RESEARCH COMPANY LIMITED, Maharashtra (IN)

(72) Inventors: Ranjan Kumar Pal, Baroda (IN); Amit Pravinbhai Sedani, Baroda (IN); Kaushikkumar Dhanjibhai Prajapati, Baroda (IN); Dijixa Pinakin Rana, Baroda (IN); Sandeep Pankajbhai Pathak, Baroda (IN); Japan Nitinkumar Desai, Baroda (IN); Jayraj Dilipbhai Aradhye, Baroda (IN); Bhavesh Mohanbhai Panchal, Baroda (IN); Indraneel Ghosh, Baroda (IN); Trinadha Rao Chitturi, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/082,488

(22) Filed: Oct. 28, 2020

(65) Prior Publication Data
US 2021/0053947 A1 Feb. 25, 2021

Related U.S. Application Data

(63) Continuation of application No. 15/770,824, filed as application No. PCT/IN2016/050364 on Oct. 26, 2016, now Pat. No. 10,865,199.

(30) Foreign Application Priority Data

Oct. 27, 2015 (IN) .......................... 4058/MUM/2015

(51) Int. Cl.
| C07D 405/10 | (2006.01) |
| C07D 311/60 | (2006.01) |
| C07D 335/06 | (2006.01) |
| C07D 215/12 | (2006.01) |

(52) U.S. Cl.
CPC ......... *C07D 405/10* (2013.01); *C07D 215/12* (2013.01); *C07D 311/60* (2013.01); *C07D 335/06* (2013.01)

(58) Field of Classification Search
CPC .................................................. C07D 405/10
See application file for complete search history.

(56) References Cited

U.S. PATENT DOCUMENTS

| 5,389,646 A | 2/1995 | Labroo |
| 5,395,842 A | 3/1995 | Labrie et al. |
| 5,407,947 A | 4/1995 | Bryant et al. |
| 5,840,735 A | 11/1998 | Labrie et al. |
| 5,916,916 A | 6/1999 | Hauser et al. |
| 6,060,503 A | 5/2000 | Labrie et al. |
| 2004/0034017 A1 | 2/2004 | Kuenzer et al. |
| 2018/0354936 A1* | 12/2018 | Pal ................ C07D 215/12 |

FOREIGN PATENT DOCUMENTS

| EP | 0470310 A1 | 2/1992 |
| TW | 240215 B | 2/1995 |
| WO | WO 99/02512 A1 | 1/1999 |
| WO | WO 01/68634 A1 | 9/2001 |
| WO | WO 2004/091488 A2 | 10/2004 |
| WO | WO 2010/145010 A1 | 12/2010 |
| WO | WO 2011/156518 A2 | 12/2011 |
| WO | WO 2013/090829 A1 | 6/2013 |
| WO | WO 2013/090836 A1 | 6/2013 |
| WO | WO 2013/090921 A1 | 6/2013 |
| WO | WO 2014/203132 A1 | 12/2014 |
| WO | WO 2014/205136 A1 | 12/2014 |
| WO | WO 2014/205138 A1 | 12/2014 |
| WO | WO 2016/097073 A1 | 6/2016 |
| WO | WO 2016/189011 A1 | 12/2016 |

OTHER PUBLICATIONS

Shafie "Estrogen and the Growth of Breast Cancer:New Evidence Suggests Indirect Action" Science, 209 (4457), 1980, pp. 701-702.*
Binkhorst "Individualization of Tamoxifen Treatment for Breast Carcinoma" Clinical Pharmacology & Therapeutics 2012, 92 (4) 431-433.*
Mac Bride "Vulvovaginal Atrophy" Mayo Clin Proc. • Jan. 2010;85(1):87-94.*
Nwachukwu "Predictive features of ligand-specific signaling through the estrogen receptor" Mol Syst Biol (2016)12:864.*
Bolego "Selective Agonists of Estrogen Receptor Isoforms New Perspectives for Cardiovascular Disease" Arterioscler Thromb Vase Biol. 2006;26:2192-2199.*
Sep. 23, 2021, Chinese Office Action Issued for CN application No. 201680072702.8.
Apr. 8, 2020, Ukrainian Office Action issued for related UA Application No. a201805396.
May 19, 2020, Israeli Office Action issued for related IL Application No. 258949.
Written Opinion of the International Searching Authority of PCT/IN2016/050364 dated Apr. 4, 2017.
International Search Report of PCT/IN2016/050364 dated Apr. 4, 2017.
Jun. 10, 2022, European Search Report issued for related EP Application No. 22164031.1.

* cited by examiner

*Primary Examiner* — David K O'Dell
(74) *Attorney, Agent, or Firm* — Paratus Law Group, PLLC

(57) ABSTRACT

The present invention provides novel heterocyclic compounds as anticancer agents, especially as estrogen receptor (ER) antagonists/degraders and process for their preparation.

11 Claims, No Drawings

HETEROCYCLIC ANTIESTROGENS

RELATED APPLICATIONS

This application is a continuation of U.S. patent application Ser. No. 15/770,824 (filed Apr. 25, 2018), which is a National Stage Patent Application of PCT International Patent Application No. PCT/IN2016/050364 (filed Oct. 26, 2016) under 35 U.S.C. § 371, which claims priority to Indian Patent Application no. 4058/MUM/2015 filed on Oct. 27, 2015 which is hereby incorporated by reference.

FIELD OF THE INVENTION

The present invention provides novel heterocyclic compounds as anticancer agents, especially as estrogen receptor (ER) antagonists/degraders and process for their preparation.

BACKGROUND OF THE INVENTION

Endogenous estrogen, 17 β-estradiol (E2) shows a wide variety of biological activities in the reproductive systems, bone metabolism, and the cardiovascular systems, as well as the central nervous system. The link between estrogen and breast cancer growth and development has been well established.

A number of strategies to inhibit the action of endogenous estrogen in estrogen receptor (ER) positive breast cancer are in practice. These include, selective ER modulators (SERMs) such as tamoxifen, which act as selective tissue-specific antagonist of ER in the breast; selective ER degraders (SERD) such as fulvestrant, which promote ER turnover, and aromatase inhibitors (AI) such as exemestane (steroidal), anastrozole and letrozole (nonsteroidal) which inhibit estrogen biosynthesis and are primarily used for postmenopausal women with ER-positive breast cancer. Unfortunately, many women with breast cancer initially respond well to tamoxifen or AI therapy but develop resistance over a period of time during treatment. In resistant form of breast cancer there is evidence that pro-growth signaling pathways downstream of estrogen receptor still play a significant role. Recently, there has been increasing clinical evidence that following treatment with AIs, resistance develop due to mutations in the ligand-binding domain of ER-α rendering it constitutively active even in the absence of ligand, leading to resistance.

Currently fulvestrant is considered as a first-in-class SERD. Unfortunately, significant pharmaceutical liabilities of fulvestrant (requiring intramuscular injection of large volume) limit its widespread use. Therefore, development of an orally bio-available ER-antagonist especially with ER degrading properties would be beneficial to patients who have developed resistance to currently available therapies targeting ER activity. Many non-steroidal ER antagonists are reported in prior art. For instance U.S. Pat. No. 5,395,842 discloses anti-estrogenic compounds and compositions. WIPO application WO 2014203132A1, WO2011156518A1, WO2013090829A1, US patents U.S. Pat. Nos. 5,389,646, 5,407,947 and European patent EP 470310 discloses benzopyran compounds useful for treatment or prevention of conditions modulated through the estrogen receptor.

SUMMARY OF THE INVENTION

The present invention provides a compound of Formula I

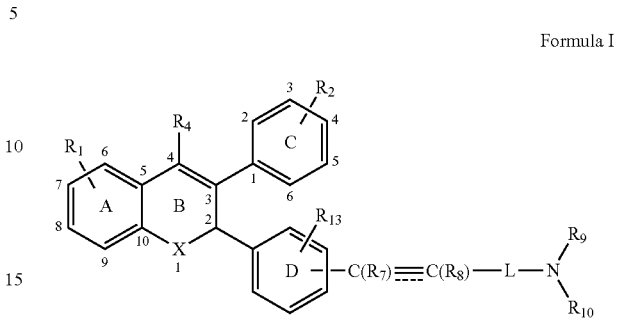

Formula I or salts or stereoisomers thereof wherein, $R_1$ is mono or di-substitution on ring A and is selected from a group comprising —$R_3$, —$OR_3$, halogen, —$C_{1-6}$ haloalkyl, —$OC_{1-6}$ haloalkyl, —CN, —$N(R_3)_2$, —$NR_3SO_2R_3$, —$NR_3CHO$, —$NR_3COR_3$, —$OC(O)R_3$, —$OC(O)N(R_3)_2$, —$OP(O)(OH)_2$ and —$OC(O)OR_3$ wherein $R_3$ at each occurrence is selected from hydrogen, and $C_{1-6}$ linear, branched or cyclic alkyl;

$R_2$ is mono or di-substitution and is selected from a group comprising —$R_{11}$, —$OR_{11}$, halogen, —$C_{1-6}$ haloalkyl, —$OC_{1-6}$ haloalkyl, —CN, —$N(R_{11})_2$, —$NR_{11}SO_2R_{11}$, —$NR_{11}CHO$, —$NR_{11}COR_{11}$, —$OC(O)R_{11}$, —$OC(O)N(R_{11})_2$, —$OP(O)(OH)_2$ and —$OC(O)OR_{11}$ wherein $R_{11}$ at each occurrence is selected from hydrogen, and $C_{1-6}$ linear, branched or cyclic alkyl;

$R_4$ is selected from hydrogen, —$C_{1-5}$ alkyl, —$C_{3-4}$ cycloalkyl, —$OC_{1-5}$ alkyl, —$C_{1-5}$ haloalkyl, halogen;

L is selected from $C_{1-7}$ linear or branched alkyl;

$R_7$ and $R_8$ are absent or independently selected from hydrogen and $C_{1-5}$ alkyl;

$R_9$ and $R_{10}$ are independently selected from hydrogen or $C_{1-20}$ linear, branched or cyclic alkyl or $C_{1-20}$ haloalkyl optionally interrupted with one or more radicals independently selected from —O—, —$NR_5$—, —S—, —SO—, —$S(O_2)$—, —$CR_5$=$CR_5$—, —C≡C—, —$NR_5CO$—, —$NR_5CO$—, —$NR_5CONR_5$—, $NR_5C(O)O$—, and —OC(O)O—; wherein $R_5$ at each occurrence is selected from a group comprising hydrogen or $C_{1-6}$ linear, branched or cyclic alkyl;

or $R_9$ and $R_{10}$ together with the nitrogen atom to which they are attached forms a 4 to 7 membered ring optionally containing 1 to 2 additional heteroatoms selected from oxygen, nitrogen or sulfur, and the ring is optionally substituted with one or more group selected from halogen, —$OR_6$, —$N(R_6)_2$ and R wherein $R_6$, at each occurrence is selected from a group comprising hydrogen, $C_{1-20}$ linear, branched or cyclic alkyl optionally interrupted with one or more radicals independently selected from —O—, —$NR_5$—, —S—, —SO—, —$S(O)_2$—, —$CR_5$=$CR_5$—, —C≡C—, —$NR_5CO$—, —$CONR_5$—, —$NR_5CONR_5$—, $NR_5C(O)O$— and —OC(O)O—;

optionally, $R_6$ is further substituted with one or more groups selected from a group comprising halogen, —$OR_{12}$, —$N(R_{12})_2$, and —$COOR_{12}$, —$CON(R_{12})_2$ or —$CON(R_{12})$OH; wherein $R_{12}$ at each occurrence is selected from hydrogen or $C_{1-6}$ linear, branched or cyclic alkyl;

≡ is a double or a triple bond;

$R_{13}$ is selected from a group comprising —$R_{14}$, —$OR_{14}$, halogen, —$C_{1-6}$ haloalkyl, —$OC_{1-6}$ haloalkyl, —CN, —N(R$_{14}$)$_2$, —NR$_{14}$SO$_2$R$_{14}$, —NR$_{14}$CHO, —NR$_{14}$COR$_{14}$, —OC(O)R$_{14}$, —OC(O)N(R$_{14}$)$_2$, —OP(O)(OH)$_2$ and —OC(O)OR$_{14}$ wherein R$_{14}$ at each occurrence is selected from hydrogen, and C$_{1-6}$ linear, branched or cyclic alkyl; and X is selected from NH, sulfur and oxygen;

with a proviso that, when R$_{13}$ is hydrogen, R$_1$ and R$_2$ are mono substitution and are hydroxyl group and R$_2$ is present at 4 position of the ring C, then R$_1$ is not at position 8 of the ring A.

The compounds of present invention are antagonists/degraders of estrogen receptors and can be used for the treatment of diseases which are related to modulation of ER.

Glossary

The term "halogen", as used herein includes chloro, fluoro, bromo and iodo. The term "haloalkyl" refers to alkyl group substituted with one or more halogen radicals.

The term "alkyl" refers to a saturated hydrocarbon chain that includes carbon and hydrogen atoms in the backbone, either linear or branched, having from 1 to 20 carbon atoms, both inclusive unless defined otherwise. The length of the chain may vary and is defined by the expression, for example, C$_{1-20}$ which means an alkyl chain having 1 to 20 carbon atoms. The term alkyl includes linear as well as branched alkyl. The examples of alkyl chain are methyl, ethyl, n-propyl, 1-methylethyl (isopropyl), n-butyl, n-pentyl, and 1,1-dimethylethyl (t-butyl). Unless set forth or recited to the contrary, all alkyl groups described or claimed herein may be substituted or unsubstituted. The numbers or the range written as subscript in terms like "C$_{1-6}$" refers to the number of carbon atoms in the group. Thus the referred group may have 1, 2, 3, 4, 5 or 6 carbon atoms.

The term "cycloalkyl" or "cyclic alkyl" denotes a non-aromatic monocyclic ring. The size of the ring is described by the expression, for example C$_{3-4}$ which denotes that the ring may have 3 or 4 carbon atoms. Wherever the ring size is not defined, the cycloalkyl or cyclic alkyl ring may contain 3 to 8 carbon atoms. The examples of cycloalkyl ring include, but are not limited to, cylcopropyl, cyclobutyl, cyclopentyl and cyclohexyl. Unless set forth or recited to the contrary, all cycloalkyl groups described or claimed herein may be substituted or unsubstituted.

DESCRIPTION OF THE INVENTION

In one aspect the present invention provides a compound of Formula I

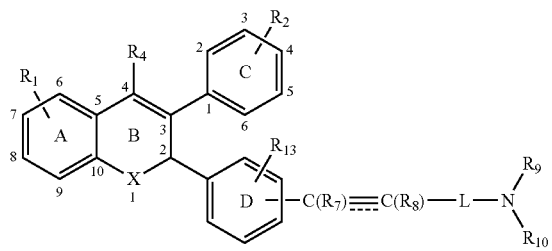

Formula I or salts or stereoisomers thereof wherein,

R$_1$ is mono or di-substitution on ring A and is selected from a group comprising —R$_3$, —OR$_3$, halogen, —C$_1$—, haloalkyl, —OC$_{1-6}$ haloalkyl, —CN, —N(R$_3$)$_2$, —NR$_3$SO$_2$R$_3$, —NR$_3$CHO, —NR$_3$COR$_3$, —OC(O)R$_3$, —OC(O)N(R$_3$)$_2$, —OP(O)(OH)$_2$ and —OC(O)OR$_3$ wherein R$_3$ at each occurrence is selected from hydrogen, and C$_{1-6}$ linear, branched or cyclic alkyl;

R$_2$ is mono or di-substitution and is selected from a group comprising —R$_{11}$, —OR$_{11}$, halogen, —C$_{1-6}$ haloalkyl, —OC$_{1-6}$ haloalkyl, —CN, —N(R$_3$)$_2$, —NR$_{11}$SO$_2$R$_{11}$, —NR$_{11}$CHO, —NR$_{11}$COR$_{11}$, —OC(O)R$_{11}$, —OC(O)N(R$_{11}$)$_2$, —OP(O)(OH)$_2$ and —OC(O)OR$_{11}$ wherein R$_{11}$ at each occurrence is selected from hydrogen, and C$_{1-6}$ linear, branched or cyclic alkyl;

R$_4$ is selected from hydrogen, —C$_{1-5}$ alkyl, —C$_{3-4}$ cycloalkyl, —OC$_{1-5}$ alkyl, —C$_{1-5}$ haloalkyl, halogen;

L is selected from C$_{1-7}$ linear or branched alkyl;

R$_7$ and R$_8$ are absent or independently selected from hydrogen and C$_{1-5}$ alkyl;

R$_9$ and R$_{10}$ are independently selected from hydrogen or C$_{1-20}$ linear, branched or cyclic alkyl or C$_{1-20}$ haloalkyl optionally interrupted with one or more radicals independently selected from —O—, —NR$_5$—, —S—, —SO—, —S(O$_2$)—, —CR$_5$=CR$_5$—, —C≡C—, —NR$_5$CO—, —NR$_5$CO—, —NR$_5$CONR$_5$—, NR$_5$C(O)O—, and —OC(O)O—; wherein R$_5$ at each occurrence is selected from a group comprising hydrogen or C$_{1-6}$ linear, branched or cyclic alkyl;

or R$_9$ and R$_{10}$ together with the nitrogen atom to which they are attached forms a 4 to 7 membered ring optionally containing 1 to 2 additional heteroatoms selected from oxygen, nitrogen or sulfur, and the ring is optionally substituted with one or more group selected from halogen, —OR$_6$, —N(R$_6$)$_2$ and R$_6$ wherein R$_6$, at each occurrence is selected from a group comprising hydrogen, C$_{1-20}$ linear, branched or cyclic alkyl optionally interrupted with one or more radicals independently selected from —O—, —NR$_5$—, —S—, —SO—, —S(O)$_2$—, —CR$_5$=CR$_5$—, —C≡C—, —NR$_5$CO—, —CONR$_5$—, —NR$_5$CONR$_5$—, NR$_5$C(O)O— and —OC(O)O—;

optionally, R$_6$ is further substituted with one or more groups selected from a group comprising halogen, —OR$_{12}$, —N(R$_{12}$)$_2$, and —COOR$_{12}$, —CON(R$_{12}$)$_2$ or —CON(R$_{12}$)OH; wherein R$_{12}$ at each occurrence is selected from hydrogen or C$_{1-6}$ linear, branched or cyclic alkyl;

══ is a double or a triple bond;

R$_{13}$ is selected from a group comprising —R$_{14}$, —OR$_{14}$, halogen, —C$_{1-6}$ haloalkyl, —OC$_{1-6}$ haloalkyl, —CN, —N(R$_{14}$)$_2$, —NR$_{14}$SO$_2$R$_{14}$, —NR$_{14}$CHO, —NR$_{14}$COR$_{14}$, —OC(O)R$_{14}$, —OC(O)N(R$_{14}$)$_2$, —OP(O)(OH)$_2$ and —OC(O)OR$_{14}$ wherein R$_{14}$ at each occurrence is selected from hydrogen, and C$_{1-6}$ linear, branched or cyclic alkyl; and X is selected from NH, sulfur and oxygen;

with a proviso that, when R$_{13}$ is hydrogen, R$_1$ and R$_2$ are mono substitution and are hydroxyl group and R$_2$ is present at 4 position of the ring C, then R$_1$ is not at position 8 of the ring A.

R$_1$ can be mono or di-substitution on ring A. When R$_1$ is di-substitution, the two groups are independently selected from each other and can be same or different. In one embodiment the present invention provides compound of Formula I, wherein R$_1$ is selected from —OR$_3$, —OC(O)R$_3$, —OC(O)N(R$_3$)$_2$, and —OC(O)OR$_3$. In another embodiment R$_1$ is selected from OH, OR$_3$, or —OC(O)R$_3$. In another embodiment R$_1$ is selected from —N(R$_3$)$_2$, —NR$_3$SO$_2$R$_3$, —NR$_3$CHO and —NR$_3$COR$_3$.

R$_2$ can be mono or di-substitution on ring C. When R$_2$ is di-substitution, the two groups are independently selected from each other and can be same or different. In another embodiment the present invention provides compound of Formula I, wherein $R_2$ is selected from —$OR_{11}$, —$OC(O)R_{11}$, —$OC(O)N(R_{11})_2$, and —$OC(O)OR_{11}$. In another embodiment $R_2$ is selected from $OR_1$, and —$OC(O)R_{11}$.

In another embodiment the present invention provides compound of Formula I, wherein $R_2$ is selected from —$N(R_{11})_2$, —$NR_{11}SO_2R_{11}$, —$NR_{11}CHO$ and —$NR_{11}COR_{11}$.

In another embodiment the present invention provides compound of Formula I, wherein $R_{11}$ is selected from —$C_{1-5}$ alkyl or —$C_{1-5}$ haloalkyl.

In another embodiment the present invention provides compound of Formula I, wherein $R_1$ and $R_2$ are hydroxyl group.

The invention intends to exclude the compounds wherein when $R_{13}$ is hydrogen, $R_1$ and $R_2$ are mono substitution and are hydroxyl group and $R_2$ is present at 4 position of ring C, then $R_1$ is not at position 8 of the ring A.

In another embodiment the present invention provides compound of Formula I, wherein L is selected from $C_{1-4}$ linear or branched alkyl.

In another embodiment the present invention provides compound of Formula I, wherein $R_4$ is —$C_{1-5}$ alkyl. In another embodiment $R_4$ is methyl.

In another embodiment the present invention provides compound of Formula I, wherein ═ is a double bond.

In another embodiment the present invention provides compound of Formula I, wherein $R_7$ and $R_8$ are hydrogen.

In one embodiment the present invention provides the compound of Formula I, wherein $R_9$ and $R_{10}$ are independently selected from a group comprising hydrogen or $C_{1-20}$ linear, branched or cyclic alkyl or $C_{1-20}$ haloalkyl optionally interrupted with one or more radicals independently selected from —O—, —$NR_5$—, —S—, —SO—, —$S(O_2)$—, —$CR_5$═$CR_5$—, —C≡C—, —$NR_5CO$—, —$NR_5CO$—, —$NR_5CONR_5$—, $NR_5C(O)O$—, and —$OC(O)O$—; wherein $R_5$ at each occurrence is selected from a group comprising hydrogen or $C_{1-6}$ linear, branched or cyclic alkyl. The phrase "$C_{1-20}$ linear, branched or cyclic alkyl" includes groups wherein and linear or branched chain alkyl group is substituted with a cycloalkyl ring with total number of the carbon atoms in alkyl chain and cycloalkyl ring are equal to or less than 20. For instance, it refers to groups like, but not limited to, $C_{1-10}$ alkyl-$C_{3-6}$ cycloalkyl. $R_9$ and $R_{10}$ can be interrupted by one or more time with same group The substitutions $R_9$ and $R_{10}$ together with the nitrogen to which they are attached may form a 4 to 7 membered ring optionally containing 1 to 2 additional heteroatoms selected from oxygen, nitrogen or sulfur. Examples of such rings include, but not limited to,

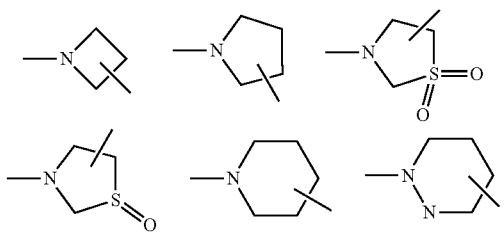

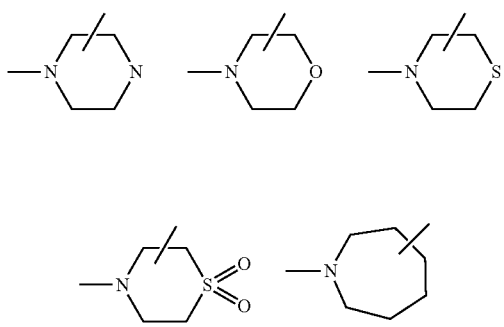

In another embodiment $R_9$ and $R_{10}$ together with the nitrogen atom to which they are attached form a 5 to 6 membered ring optionally containing 1 additional heteroatom selected from oxygen, nitrogen and sulfur. When $R_9$ and $R_{10}$ together with the nitrogen atom to which they are attached forms a ring, the ring may be further substituted with $R_6$, wherein $R_6$ is a $C_{1-15}$ linear or branched alkyl optionally interrupted with one or more radicals independently selected from —O—, —$NR_5$—, —S— or —$CR_5$═$CR_5$—. In another embodiment $R_6$ can be further substituted with one or more groups selected from a group comprising halogen, —$OR_5$, —$N(R_5)_2$, and —$COOR_5$, —$CON(R_5)_2$ or —$CON(R_5)OH$;

In another embodiment $R_9$ is hydrogen or $C_{1-3}$ alkyl and $R_{10}$ is selected from $C_{1-15}$ linear or branched alkyl optionally interrupted with one or more radicals selected from —O—, —$NR_5$—, —S— and —$CR_5$═$CR_5$—.

In another embodiment the present invention provides the compound of Formula I, wherein $R_{13}$ is selected from a group comprising —$R_{14}$, —$OR_{14}$, halogen, —$C_{1-6}$ haloalkyl, —$OC_{1-6}$ haloalkyl, —CN, —$N(R_{14})_2$, —$NR_{14}SO_2R_{14}$, —$NR_{14}CHO$, —$NR_{14}COR_{14}$, —$OC(O)R_{14}$, —$OC(O)N(R_{14})_2$, —$OP(O)(OH)_2$ and —$OC(O)OR_{14}$ wherein $R_{14}$ at each occurrence is selected from hydrogen, and $C_{1-6}$ linear, branched or cyclic alkyl. In another embodiment the $R_{13}$ is a group selected from hydrogen, halogen, —$C_{1-6}$ haloalkyl and —$C_{1-6}$ alkyl.

In another embodiment the present invention provides the compound of Formula I, wherein X is NH.

In another embodiment the present invention provides a compound of Formula Ia

Formula Ia

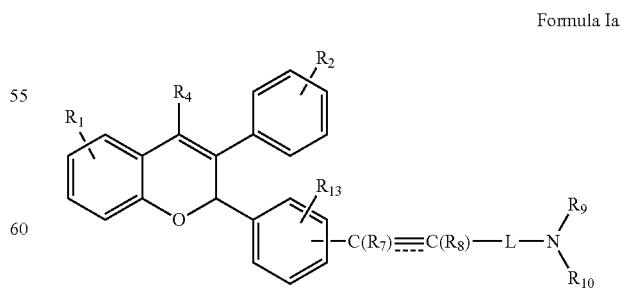

wherein $R_1$, $R_2$, $R_4$, $R_9$, $R_{10}$, $R_{13}$ and L are groups as defined above.

In another embodiment the present invention provides a compound of Formula Ib

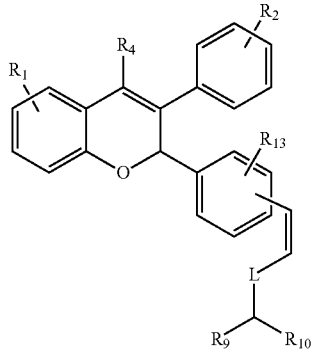

Formula Ib wherein $R_1$, $R_2$, $R_4$, $R_9$, $R_{10}$, $R_{13}$ and L are groups as defined above.

In another embodiment the present invention provides a compound of Formula Ic

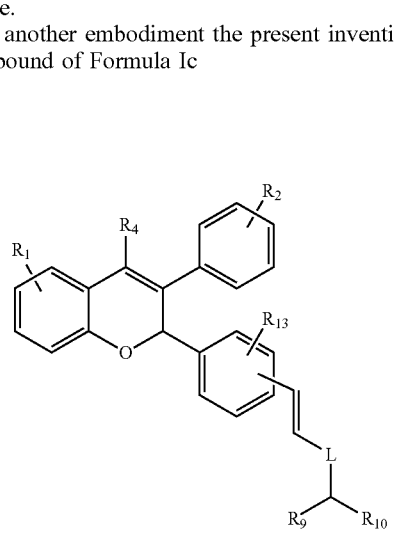

Formula Ic wherein $R_1$, $R_2$, $R_4$, $R_9$, $R_{10}$, $R_{13}$ and L are groups as defined above.

In a preferred embodiment the present invention provides a compound of Formula Id

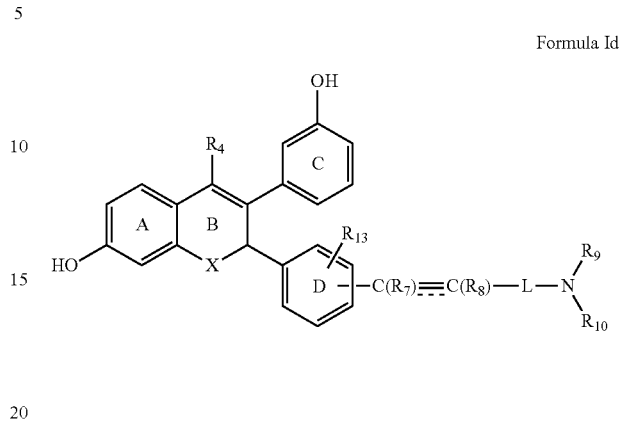

Formula Id wherein $R_4$, $R_7$, $R_8$, $R_9$, $R_{10}$, $R_{13}$, X and L are groups as defined above.

In another preferred embodiment the present invention provides a compound of Formula Ie

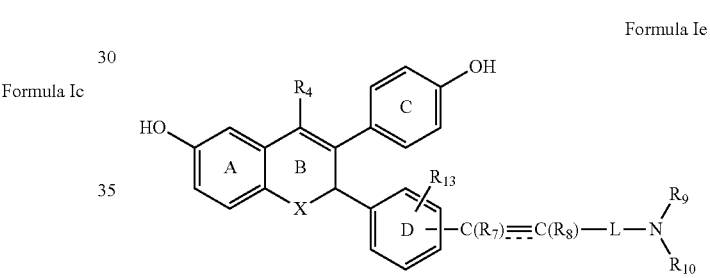

Formula Ie wherein $R_4$, $R_7$, $R_8$, $R_9$, $R_{10}$, $R_{13}$, X and L are groups as defined above.

In another preferred embodiment the present invention provide a compound of Formula I, Ia, Ib, Ic, Id and Ie wherein the substitution on Ring D is at 4 position.

In another embodiment, the compound of Formula Ia or Ib can be prepared by the route as depicted in the following Scheme 1.

Scheme 1

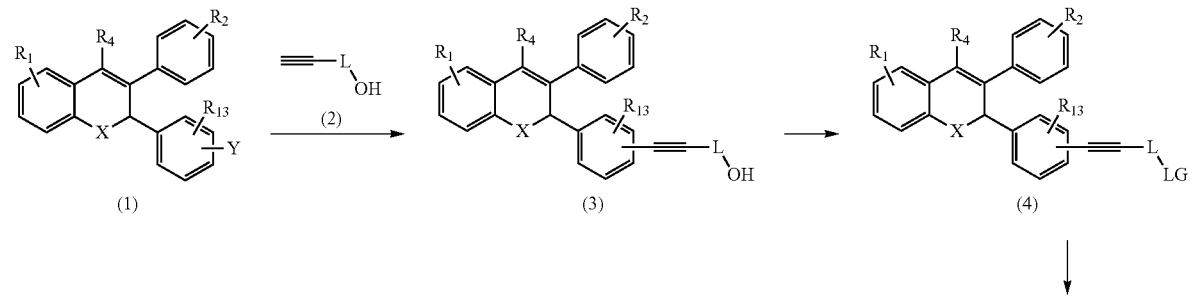

-continued

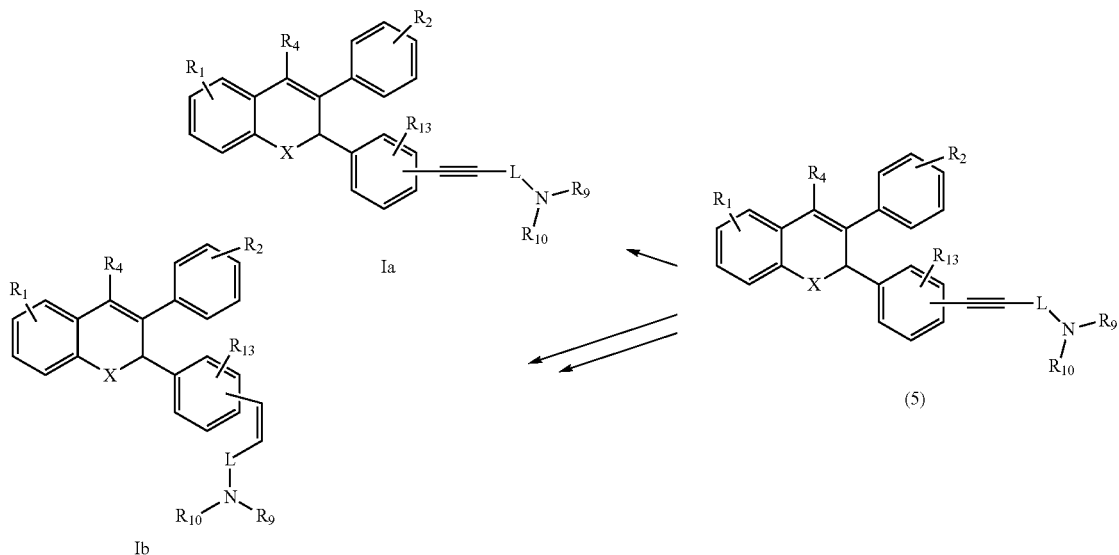

Compound (1) can be prepared by the processes reported in the art for example US patent application publication 20140107095A1 and their obvious modifications. It is well under general purview of those skilled in the art that when the substituent groups $R_1$ and $R_2$ are selected from one which may interfere with the general course of the reaction scheme, the groups may be protected with a suitable protecting group such as provided in text book Greene's Protective Groups in Organic Chemistry by Peter G. M. Wuts and Theodora W Greene, 4th edition, published by Wiley Interscience.

Compound (3) can be prepared by reacting compound (1) (where in Y is halide) with alcohol (2) by Sonogashira reaction in a presence of suitable catalyst, like $Pd(PPh_3)_2Cl_2$ and CuI. Alcohol group of compound (3) can be converted to a suitable leaving group (LG) such as —OMs, —Cl, —Br, —I, —OTs, —OTf to produce compound (4). In some embodiments, where LG- is —OMs, compound (4) may be converted to compound of formula (5) by reacting with suitable amine. Deprotection of compound (5) would give compound Ia. The reduction of compound of formula (5) using reducing agent such as Lindlar catalyst followed by deprotection can provide compound of Formula (Ib).

In some embodiments, the compounds of formula Ic can be prepared as described in the following Scheme 2.

Scheme 2

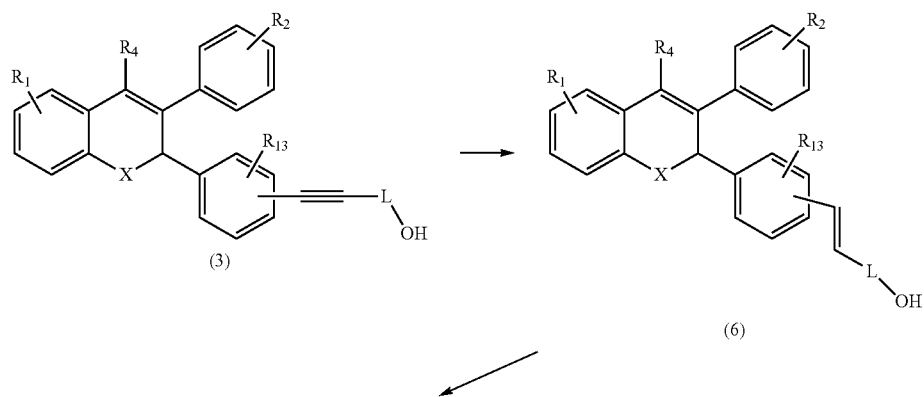

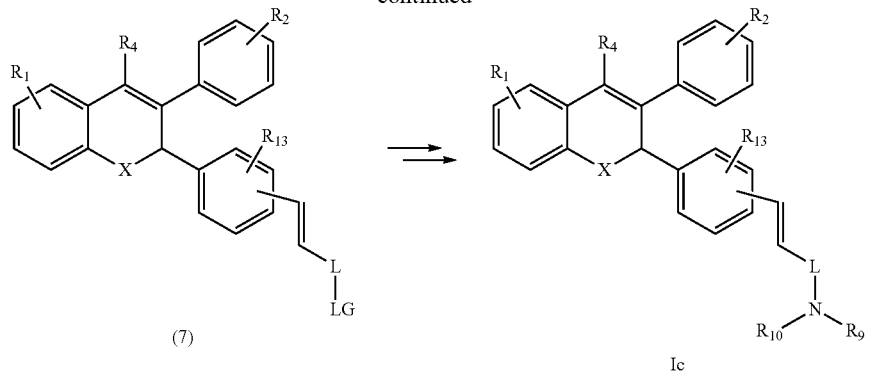

The compound (3) can be reduced using reducing agent such as lithium aluminium hydride (LAH) in a suitable solvent to compound (6). Alcohol group of compound (6) is further converted to suitable leaving group like —OMs, —Cl, —Br, —I, —OTs, —OTf to yield compound (7). In some embodiments, where LG- is —OMs, compound (7) can be converted to compound of Formula (Ic) by reacting with suitable amine followed by deprotection.

Alternatively the compound of Formula Ib can also be prepared as outlined in the following Scheme 3.

Scheme 3

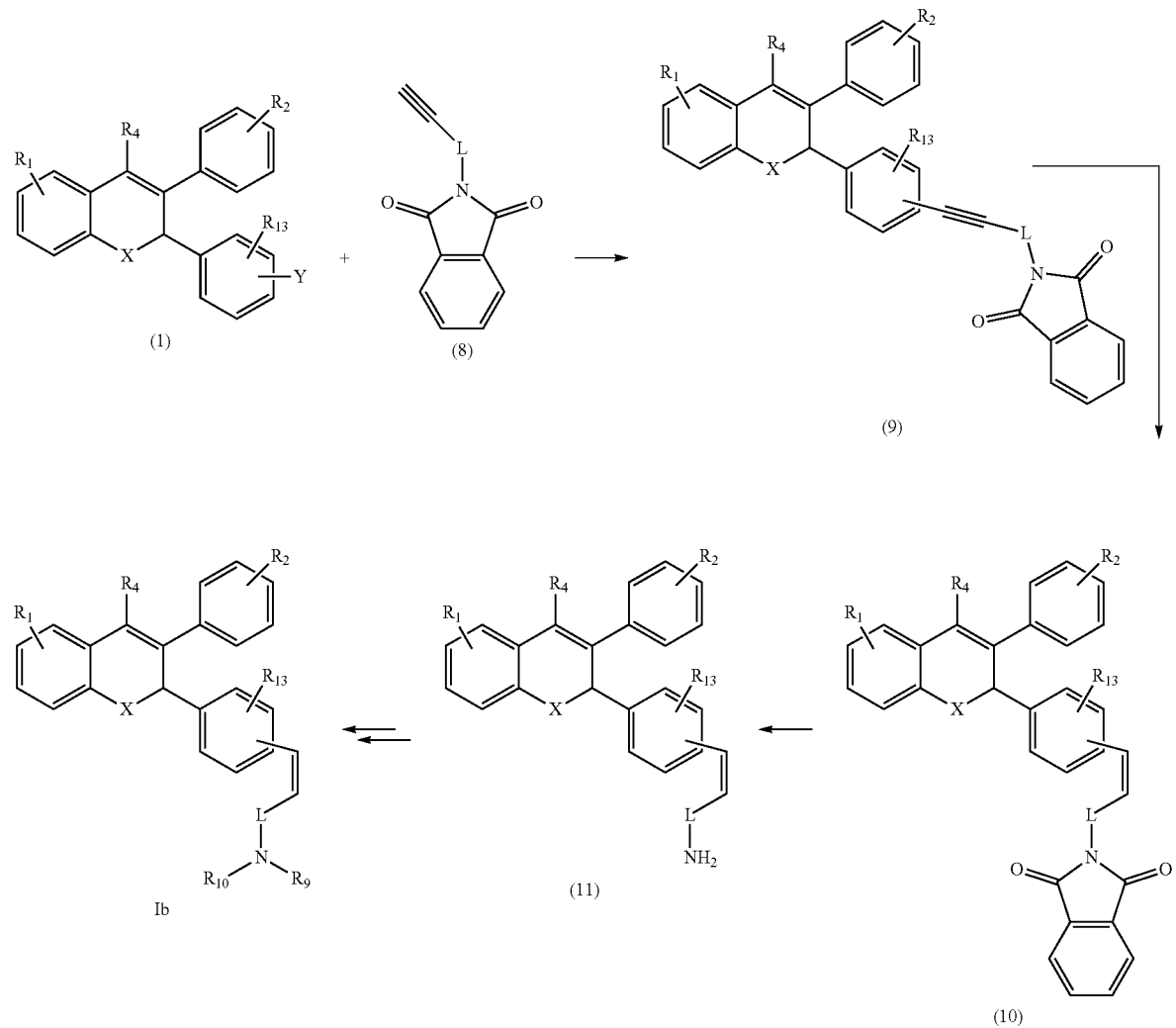

The compound (1) (where in Y is halide) may be reacted with alkyne (8) in a presence of suitable catalyst, like Pd(PPh$_3$)$_2$Cl$_2$ and CuI (Sonogashira reaction) to yield compound (9). It is then reduced to compound (10) using Lindlar catalyst. Compound (10) may be converted to amine (11) which may then be converted to compound of Formula Ib under suitable reaction condition which may include deprotection step.

The substituents R$_1$ and R$_2$ are suitably protected with suitable protecting groups before proceeding for chemical transformations as and when it is required.

Alternatively compounds described herein can also be prepared by Heck reaction, Stille or Suzuki coupling as shown in Scheme 4 (where M is hydrogen, —Sn(alkyl)$_3$, —Cl, —Br, —I or —OTf)

Scheme 4

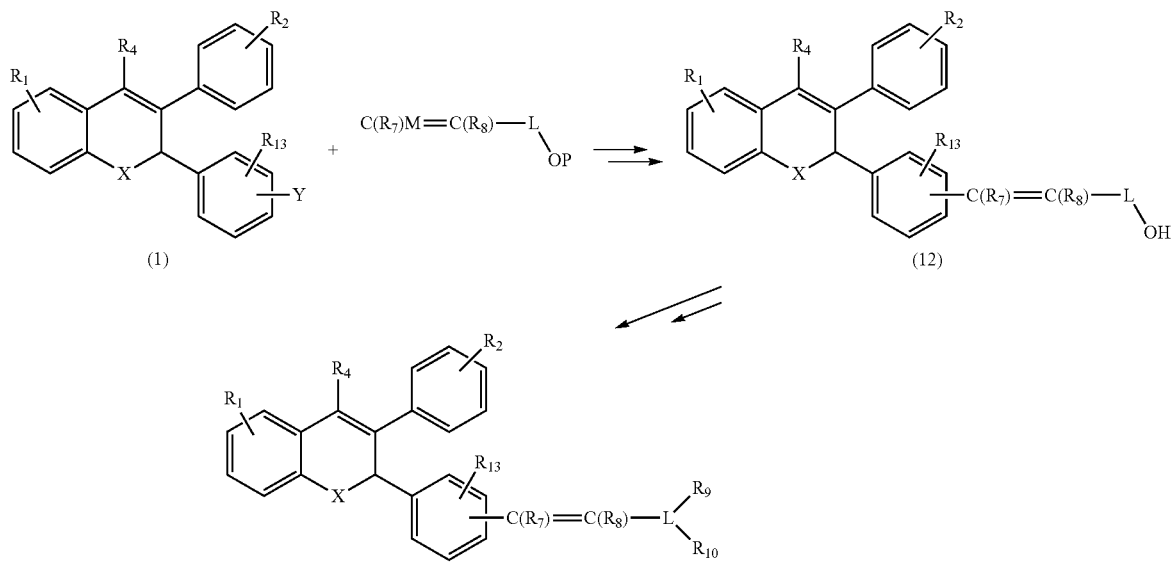

Table 1 provides few exemplary compounds of Formula I.

TABLE 1

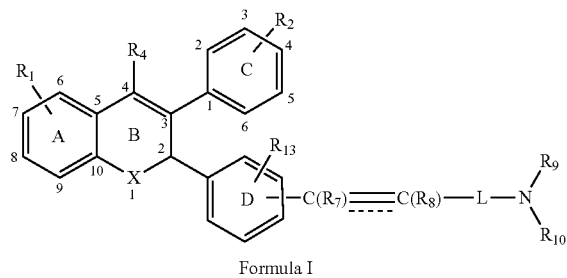

Formula I

| # | R$_1$ | R$_2$ | R$_4$ | X | —C(R$_7$)≡C(R$_8$)— | L | R$_{13}$ | —N(R$_9$)(R$_{10}$) |
|---|-------|-------|-------|---|---------------------|---|----------|---------------------|
| 1. | -7-OH | -3-OH | —CH$_3$ | —O— | -(Z) CH=CH— | —CH$_2$— | H | —NHCH$_3$ |
| 2. | -7-OH | -3-OH | —CH$_3$ | —O— | -(Z) CH=CH— | —CH$_2$— | H | —N(CH$_3$)$_2$ |
| 3. | -7-OH | -3-OH | —CH$_3$ | —O— | -(Z) CH=CH— | —CH$_2$— | H | —NH(n-C$_{12}$H$_{25}$) |
| 4. | -7-OH | -3-OH | —CH$_3$ | —O— | -(E) CH=CH— | —CH$_2$— | H | —NH(n-C$_{12}$H$_{25}$) |
| 5. | -7-OH | -3-OH | —CH$_3$ | —O— | -(Z) CH=CH— | —CH$_2$— | H | 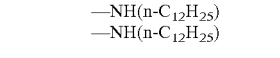 |
| 6. | -7-OH | -3-OH | —CH$_3$ | —O— | -(Z) CH=CH— | —CH$_2$— | H | —NH(CH$_2$)$_2$N(CH$_3$)$_2$ |
| 7. | -7-OH | -3-OH | —CH$_3$ | —O— | -(Z) CH=CH— | —CH$_2$— | H | —NH(CH$_2$)$_9$S(CH$_2$)$_3$CF$_2$CF$_3$ |
| 8. | -7-OH | -3-OH | —CH$_3$ | —O— | -(E) CH=CH— | —CH$_2$— | H | —NH(CH$_2$)$_9$S(CH$_2$)$_3$CF$_2$CF$_3$ |

TABLE 1-continued

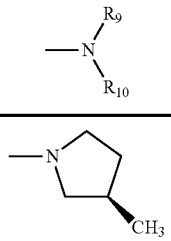

Formula I

| # | $R_1$ | $R_2$ | $R_4$ | X | —C($R_7$)=C($R_8$)— | L | $R_{13}$ | $\begin{array}{c}R_9\\|\\-N\\|\\R_{10}\end{array}$ |
|---|---|---|---|---|---|---|---|---|
| 9. | -7-OH | -3-OH | —CH$_3$ | —O— | -(Z) CH=CH— | —CH$_2$— | H | 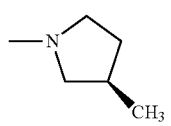 |
| 10. | -7-OH | -3-OH | —CH$_3$ | —O— | -(E) CH=CH— | —CH$_2$— | H | 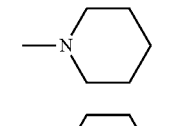 |
| 11. | -7-OH | -3-OH | —CH$_3$ | —O— | -(Z) CH=CH— | —CH$_2$— | H | 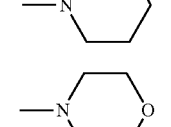 |
| 12. | -7-OH | -3-OH | —CH$_3$ | —O— | -(E) CH=CH— | —CH$_2$— | H | 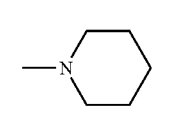 |
| 13. | -7-OH | -3-OH | —CH$_3$ | —O— | -(Z) CH=CH— | —CH$_2$— | H | 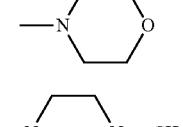 |
| 14. | -7-OH | -3-OH | —CH$_3$ | —O— | -(Z) CH=CH— | —CH$_2$— | H | 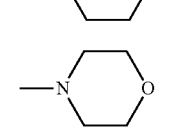 |
| 15. | -7-OH | -3-OH | —CH$_3$ | —O— | -(E) CH=CH— | —CH$_2$— | H | 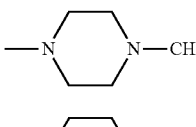 |
| 16. | -7-OH | -3-OH | —CH$_3$ | —O— | -(Z) CH=CH— | —CH$_2$— | H | 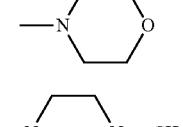 |
| 17. | -7-OH | -3-OH | —CH$_3$ | —O— | -(Z) CH=CH— | —CH$_2$— | H | 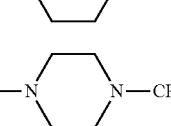 |
| 18. | -7-OH | -3-OH | —CH$_3$ | —O— | -(Z) CH=CH— | —CH$_2$— | H | 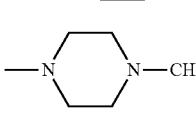 |
| 19. | -7-OC(=O)—tBu | -3-OC(=O)—t-Bu | —CH$_3$ | —O— | -(Z) CH=CH— | —CH$_2$— | H | 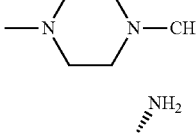 |

TABLE 1-continued

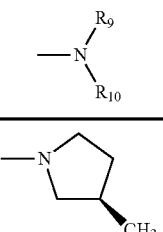

Formula I

| # | R$_1$ | R$_2$ | R$_4$ | X | —C(R$_7$)≡≡≡C(R$_8$)— | L | R$_{13}$ | —N(R$_9$)(R$_{10}$) |
|---|---|---|---|---|---|---|---|---|
| 20. | -7-OCH$_3$ | -3-OCH$_3$ | —CH$_3$ | —O— | -(Z) CH=CH— | —CH$_2$— | H | 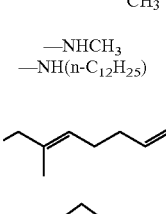 |
| 21. | -7-OH | -3-OH | —CH$_3$ | —O— | —C≡C— | —CH$_2$— | H | —NHCH$_3$ |
| 22. | -7-OH | -3-OH | —CH$_3$ | —O— | —C≡C— | —CH$_2$— | H | —NH(n-C$_{12}$H$_{25}$) |
| 23. | -7-OH | -3-OH | —CH$_3$ | —O— | —C≡C— | —CH$_2$— | H | 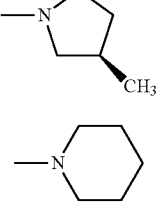 |
| 24. | -7-OH | -3-OH | —CH$_3$ | —O— | —C≡C— | —CH$_2$— | H | 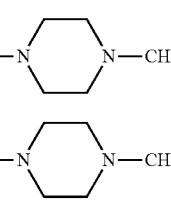 |
| 25. | -7-OH | -3-OH | —CH$_3$ | —O— | —C≡C— | —CH$_2$— | H | 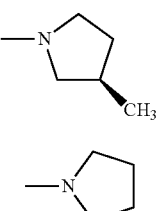 |
| 26. | -7-OH | -3-OH | —CH$_3$ | —O— | —C≡C— | —CH$_2$— | H | 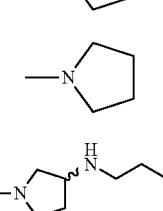 |
| 27. | -7-OH | -3-OH | —CH$_3$ | —O— | —C≡C— | —(CH$_2$)— | H | 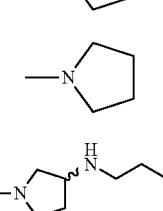 |
| 28. | -7-OH | -3-OCH$_3$ | —CH$_3$ | —O— | -(Z) CH=CH— | —CH$_2$— | H | 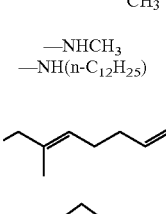 |
| 29. | -7-OH | -3-OH | —CH$_3$ | —O— | -(Z) CH=CH— | —CH$_2$— | H | 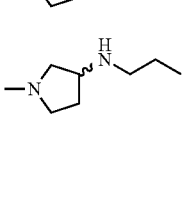 |
| 30. | -7-OH | -3-OH | —CH$_3$ | —O— | -(E) CH=CH— | —CH$_2$— | H | 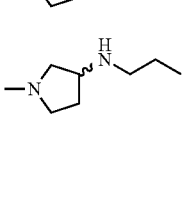 |
| 31. | -7-OH | -3-OH | —CH$_3$ | —O— | -(Z) CH=CH— | —CH$_2$— | H |  |
| 32. | -7-OH | -3-OH | —CH$_3$ | —O— | -(E) CH=CH— | —CH$_2$— | H |  |

TABLE 1-continued

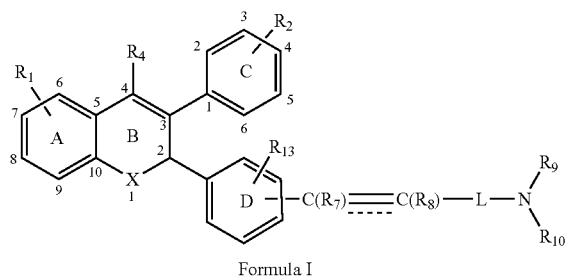

Formula I

| # | R₁ | R₂ | R₄ | X | —C(R₇)≡≡≡C(R₈)— | L | R₁₃ | —N(R₉)(R₁₀) |
|---|---|---|---|---|---|---|---|---|
| 33. | -7-OH | -3-OH | —CH₃ | —O— | -(E) CH=CH— | —CH₂— | H | N-thiomorpholinyl (N-methylthiomorpholine) |
| 34. | -7-OH | -3-OH | —CH₃ | —O— | -(Z) CH=CH— | —CH₂— | H | 4-methylpiperidin-1-yl |
| 35. | -7-OH | -3-OH | —CH₃ | —O— | -(E) CH=CH— | —CH₂— | H | —NH(n-C₉H₁₉) |
| 36. | -7-OH | -3-OH | —CH₃ | —O— | -(E) CH=CH— | —CH₂— | H | 4-methylpiperidin-1-yl |
| 37. | -7-OH | -3-OH | —CH₃ | —O— | -(Z) CH=CH— | —CH₂— | H | —NH(n-C₉H₁₉) |
| 38. | -7-OH | -3-OH | —CH₃ | —O— | -(Z) CH=CH— | —CH₂— | H | —NH(CH₂)₈CH₂F |
| 39. | -7-OH | -3-OH | —CH₃ | —O— | -(E) CH=CH— | —CH₂— | H | —NH(CH₂)₈CH₂F |
| 40. | -7-OH | -3-OH | —CH₃ | —O— | -(Z) CH=CH— | —CH(CH3)— | H | pyrrolidin-1-yl |
| 41. | -7-OH | -3-OH | —CH₃ | —O— | -(E) CH=CH— | —CH₂— | H | —NH(CH₂)₉CH₂F |
| 42. | -7-OH | -3-OH | —CH₃ | —O— | —C≡C— | —CH₂— | H | —NH(CH₂)₈CH₂F |
| 43. | -7-OH | -3-OH | —CH₃ | —O— | -(Z) CH=CH— | —CH₂— | H | —NH(CH₂)₉CH₂F |
| 44. | -7-OH | -3-OH | —CH₃ | —O— | -(E) CH=CH— | —CH₂— | H | —NH(CH₂)₈CHF₂ |
| 45. | -7-OH | -3-OH | —CH₃ | —O— | -(E) CH=CH— | —CH₂— | H | —N(CH₃)(CH₂)₈CH₂F |
| 46. | -7-OH | -3-OH | —CH₃ | —O— | -(Z) CH=CH— | —CH₂— | H | —NH(CH₂)₈CHF₂ |
| 47. | -7-OH | -3-OCH₃ | —CH₃ | —O— | -(E) CH=CH— | —CH₂— | H | —NH(CH₂)₈CH₂F |
| 48. | -7-OH | -3-OH | —CH₃ | —O— | -(Z) CH=CH— | —CH₂— | H | —N(CH₃)(CH₂)₈CH₂F |
| 49. | -7-OH | -3-OH | —CH₃ | —O— | -(E) CH=CH— | —CH₂— | H | —NH(CH₂)₇CH₂F |
| 50. | -7-OH | -3-OH | —CH₃ | —O— | -(Z) CH=CH— | —CH₂— | H | —NH(CH₂)₇CH₂F |
| 51. | -7-OH | -3-OH | —CH₃ | —O— | —C≡C— | —CH₂— | H | —NH(CH₂)₇CH₂F |
| 52. | -7-OH | -3-OH | —CH₃ | —O— | —C≡C— | —CH₂— | H | —NH(CH₂)₉CH₂F |
| 53. | -7-OH | -3-OH | —CH₃ | —O— | —C≡C— | —CH₂— | H | —NCH₃(CH₂)₉F |
| 54. | -7-OH | -3-OH | —CH₃ | —O— | —C≡C— | —CH₂— | H | —NH(CH₂)₈CHF₂ |
| 55. | -7-OH | -3-OH | —CH₃ | —O— | -(Z) CH=CH— | —CH₂— | H | (3-(iodomethyl)pyrrolidin-1-yl, N-methyl) |
| 56. | -7-OH | -3-OH | —CH₃ | —O— | —C≡C— | —CH₂— | H | 3,3-difluoropyrrolidin-1-yl (N-methyl) |
| 57. | -7-OH | -3-OH | —CH₃ | —O— | -(Z) CH=CH— | —CH₂— | H | 3,3-difluoropyrrolidin-1-yl (N-methyl) |

TABLE 1-continued

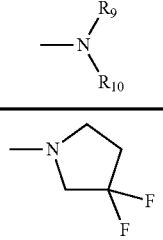

Formula I

| # | $R_1$ | $R_2$ | $R_4$ | X | —C($R_7$)≡≡C($R_8$)— | L | $R_{13}$ | —N($R_9$)($R_{10}$) |
|---|---|---|---|---|---|---|---|---|
| 58. | -7-OH | -3-OH | —CH$_3$ | —O— | -(E) CH=CH— | —CH$_2$— | H | 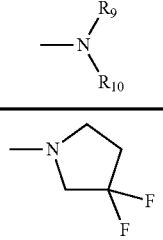 |
| 59. | -7-OH | -3-OH | —CH$_3$ | —O— | -(E) CH=CH— | —CH$_2$— | H | 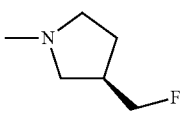 |
| 60. | -7-OH | -3-OH | —CH$_3$ | —O— | -(E) CH=CH— | —CH$_2$— | H | 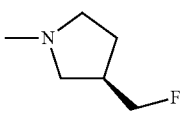 |
| 61. | -7-OH | -3-OH | —CH$_3$ | —O— | —C≡C— | —CH$_2$— | H | 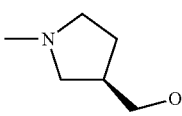 |
| 62. | -7-OH | -3-OH | —CH$_3$ | —O— | -(Z) CH=CH— | —CH$_2$— | H | 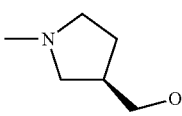 |
| 63. | -7-OH | -3-OH | —CH$_3$ | —O— | -(E) CH=CH— | —CH$_2$— | H | 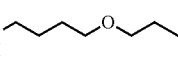 |
| 64. | -7-OH | -3-OH | —CH$_3$ | —O— | —C≡C— | —CH$_2$— | H | 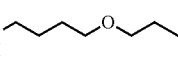 |
| 65. | -7-OH | -3-OH | —CH$_3$ | —O— | -(E) CH=CH— | —CH$_2$— | H | 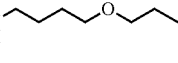 |
| 66. | -7-OH | -3-OH | —CH$_3$ | —O— | -(Z) CH=CH— | —CH$_2$— | H | 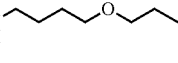 |
| 67. | -7-OH | -3-OH | —CH$_3$ | —O— | -(Z) CH=CH— | —CH$_2$— | H | 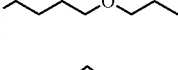 |
| 68. | -7-OC(=O)—t-Bu | -3-OC(=O)—t-Bu | —CH$_3$ | —O— | -(E) CH=CH— | —CH$_2$— | H | —NH(CH2)$_{10}$F |
| 69. | -7-OH | -3-OH | —CH$_3$ | —O— | —C≡C— | —CH$_2$— | H | —N(CH$_3$)(CH$_2$)$_9$CHF$_2$ |

TABLE 1-continued

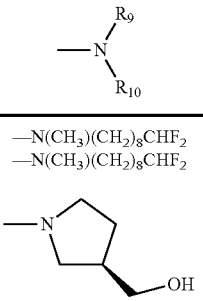

Formula I

| # | R₁ | R₂ | R₄ | X | —C(R₇)=C(R₈)— | L | R₁₃ | —N(R₉)(R₁₀) |
|---|---|---|---|---|---|---|---|---|
| 70. | -7-OH | -3-OH | —CH₃ | —O— | -(E) CH=CH— | —CH₂— | H | —N(CH₃)(CH₂)₈CHF₂ |
| 71. | -7-OH | -3-OH | —CH₃ | —O— | -(Z) CH=CH— | —CH₂— | H | —N(CH₃)(CH₂)₈CHF₂ |
| 72. | -7-OH | -3-OH | —CH₃ | —O— | -(Z) CH=CH— | —CH₂— | H | 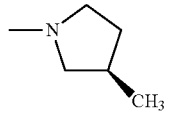 |
| 73. | -7-C(=O)CH₃ | -3-OC(=O)CH₃ | —CH₃ | —O— | -(Z) CH=CH— | —CH₂— | H | 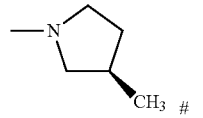 |
| 74. | -7-OC(=O)CH₃ | -3-OC(=O)CH₃ | —CH₃ | —O— | -(E) CH=CH— | —CH₂— | H | —NH(CH₂)₉F |
| 75. | -7-OH | -3-OH | —CH₃ | —O— | -(Z) CH=CH— | —CH₂— | H | 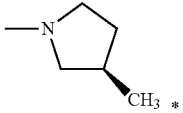 # |
| 76. | -7-OH | -3-OH | —CH₃ | —O— | -(Z) CH=CH— | —CH₂— | H | 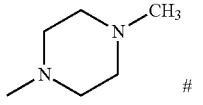 * |
| 77. | -7-OH | -3-OH | —CH₃ | —O— | -(Z) CH=CH— | —CH₂— | H | 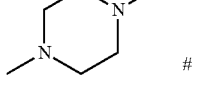 # |
| 78. | -7-OH | -3-OH | —CH₃ | —O— | -(Z) CH=CH— | —CH₂— | H | 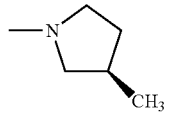 # |
| 79. | -7-OH | -3-OH | —CH₃ | —O— | -(E) CH=CH— | —CH₂— | H | —NH(CH₂)₈CH₂F # |
| 80. | -7-OH | -3-OH | —CH₃ | —O— | -(E) CH=CH— | —CH₂— | H | —NH(CH₂)₈CH₂F * |
| 81. | -7-OH | -3-OH,-5-F | —CH₃ | —O— | -(Z) CH=CH— | —CH₂— | H | 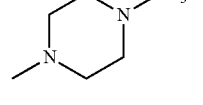 |
| 82. | -7-OH | -3-OH,-5-F | —CH₃ | —O— | -(Z) CH=CH— | —CH₂— | H | (1-methylpiperazine with N-CH₃) |

TABLE 1-continued

[Structure of Formula I: bicyclic A-B system with X at position 1, positions labeled 1-10 on A/B rings; R₁ at position 7, R₄ at position 4, phenyl ring C at position 3 with R₂; at position 2, substituent D (phenyl with R₁₃) — C(R₇)=C(R₈) — L — N(R₉)(R₁₀)]

Formula I

| # | R₁ | R₂ | R₄ | X | —C(R₇)=C(R₈)— | L | R₁₃ | —N(R₉)(R₁₀) |
|---|---|---|---|---|---|---|---|---|
| 83. | -7-OH | -3-F,-5-F | —CH₃ | —O— | -(Z) CH=CH— | —CH₂— | H | 4-methylpiperazin-1-yl-N-methyl (1,4-dimethylpiperazine via N) |
| 84. | -7-OH | -3-OH | —CH₃ | —O— | -(E) CH=CH— | —CH₂— | H | 4-methylpiperazinyl-CH₂CH₂-O-CH₂CH₂-O-CH₂CH₂-O-CH₃ |
| 85. | -7-OH | -3-OH | —CH₃ | —O— | -(Z) CH=CH— | —CH₂— | H | N(CH₃)-CH₂CH₂-O-CH₂CH₂-O-CH₂CH₂-O-CH₃ |
| 86. | -7-OH | -3-OH | —CH₃ | —O— | -(Z) CH=CH— | —CH₂— | 2-F | pyrrolidin-1-yl |
| 87. | -7-OH | -3-OH | —CH₃ | —O— | —C≡C— | —CH₂— | 2-F | pyrrolidin-1-yl |
| 88. | -7-OCH₂F | -3-OCH₂F | —CH₃ | —O— | —C≡C— | —CH₂— | H | pyrrolidin-1-yl |

* isomer A; # isomer B

The present invention is further illustrated in detail with reference to the following examples. It is desired that the examples are to be considered in all respects as illustrative and are not intended to limit the scope of the claimed invention.

EXAMPLES

General Method of Preparation

The compounds described herein, including compounds of Formula I can be prepared by reaction schemes depicted in Schemes 1, 2, 3 and 4. Furthermore, in the following examples, where specific acids, bases, reagents, coupling agents, solvents, etc. are mentioned, itis understood that other suitable acids, bases, reagents, coupling agents etc. may be used and are included within the scope of the present invention. Modifications to reaction conditions, for example, temperature, duration of the reaction or combinations thereof are envisioned as part of the present invention. The compounds obtained by using the general reaction scheme may be of insufficient purity. These compounds can be purified by any of the methods for purification of organic compounds known in the art, for example, crystallization or silica gel or alumina column chromatography using different solvents in suitable ratios. 2-(4-Iodophenyl)-4-methyl-6-(tetrahydropyran-2-yloxy)-3-[3-(tetrahydropyran-2-yloxy) phenyl]-2H-chromene is prepared in a manner similar to the process described in the US patent application publication 20140107095A 1.

Method-A

Preparation of 3-(3-hydroxyphenyl)-4-methyl-2-[4-(3-piperidin-1-yl-prop-1-ynyl)phenyl]-2H-chromen-6-ol (Compound No. 25)

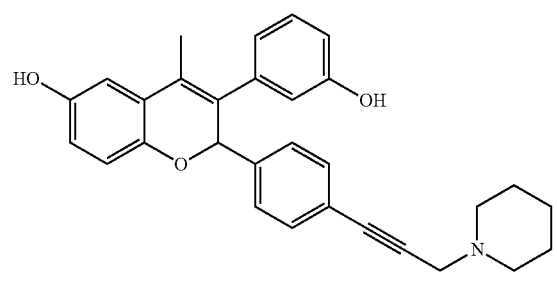 [SMILES: CC1=C(c2cccc(O)c2)C(c2ccc(C#CCN3CCCCC3)cc2)Oc2ccc(O)cc21]

Step I: 3-(4-{4-Methyl-6-(tetrahydropyran-2-yloxy)-3-[3-(tetrahydropyran-2-yloxy)phenyl]-2H-chromen-2-yl}phenyl)prop-2-yn-1-ol

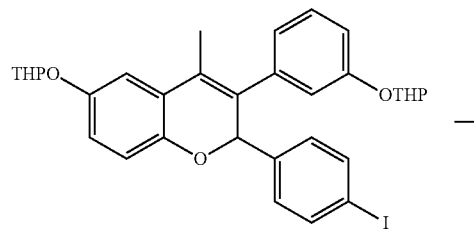

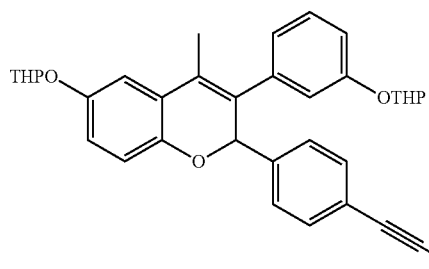

Bis(triphenylphosphine)palladium (II) dichloride (0.061 g, 0.081 mmol) was added to a stirred solution of 2-(4-iodophenyl)-4-methyl-6-(tetrahydropyran-2-yloxy)-3-[3-(tetrahydropyran-2-yloxy)phenyl]-2H-chromene (1.1 g, 1.76 mmol)(prepared as per the process provided in US 20140107095A1), propargyl alcohol (0.30 g, 5.28 mmol) and cuprous (I) iodide (0.027 g, 0.142 mmol) in a mixture of tetrahydrofuran:triethylamine (1:1, 35 mL). Stirring was continued at ambient temperature for 1 hour. It was then concentrated under reduced pressure to get a crude residue which was purified by column chromatography (silica gel, toluene:ethyl acetate 85:15) to yield 3-(4-{4-methyl-6-(tetrahydropyran-2-yloxy)-3-[3-(tetrahydropyran-2-yloxy)phenyl]-2H-chromen-2-yl}phenyl)prop-2-yn-1-ol.

Step II: 1-[3-(4-{4-Methyl-6-(tetrahydropyran-2-yloxy)-3-[3-(tetrahydropyran-2-yloxy)phenyl]-2H-chromen-2-yl}phenyl)prop-2-ynyl]piperidine

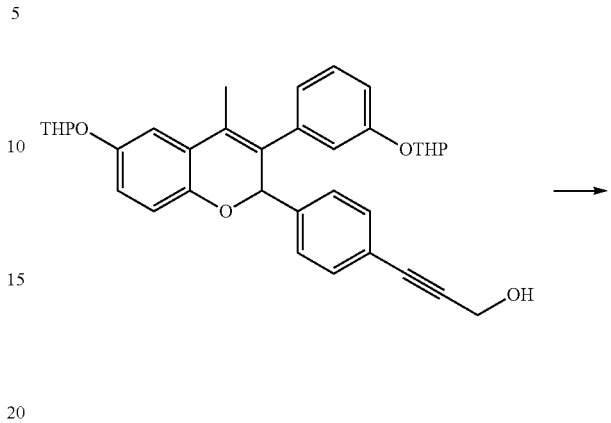

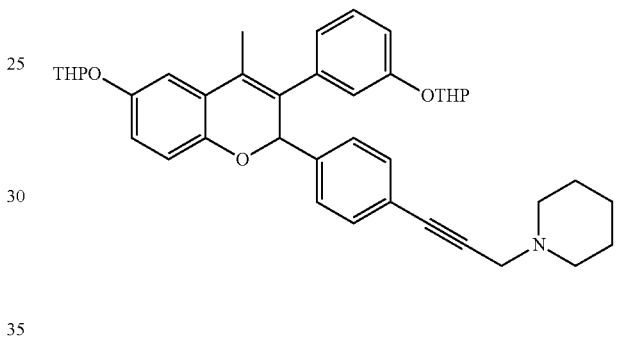

A solution of methanesulfonyl chloride (0.18 mL, 2.40 mmol) in dichloromethane (3 mL) was added to a solution of 3-(4-{4-methyl-6-(tetrahydropyran-2-yloxy)-3-[3-(tetrahydropyran-2-yloxy)phenyl]-2H-chromen-2-yl}phenyl)prop-2-yn-1-ol (1.1 g, 2.00 mmol) and triethyl amine (0.42 mL, 3.00 mmol) in dichloromethane (8 mL) at 0-5° C. The reaction mixture was stirred at 0-5° C. for 30 minutes. Water was added to the reaction mixture and the organic layer was separated. The aqueous layer was extracted with dichloromethane. Combined organic layer was dried over anhydrous sodium sulfate and concentrated under reduced pressure to get methanesulfonicacid-3-(4-{4-methyl-6-(tetrahydropyran-2-yloxy)-3-[3-(tetrahydropyran-2-yloxy)phenyl]-2H-chromen-2-yl}phenyl)prop-2-ynylester.

The solution of methanesulfonicacid-3-(4-{4-methyl-6-(tetrahydropyran-2-yloxy)-3-[3-(tetrahydropyran-2-yloxy)phenyl]-2H-chromen-2-yl}phenyl)prop-2-ynylester in acetonitrile (3 mL) was added to a slurry of piperidine (0.49 mL, 5.00 mmol) and potassium carbonate (0.714 g, 5.2 mmol) in acetonitrile (8 mL) at ambient temperature and stirred for 40 minutes. Water was added and was extracted with ethyl acetate. Combined organic layer was dried over anhydrous sodium sulfate and concentrated under reduced pressure to get crude which was purified by column chromatography (silica gel, dichloromethane:methanol 97:3) to get 1-[3-(4-{4-methyl-6-(tetrahydropyran-2-yloxy)-3-[3-(tetrahydropyran-2-yloxy)phenyl]-2H-chromen-2-yl}phenyl)prop-2-ynyl]piperidine.

Step III: 3-(3-Hydroxyphenyl)-4-methyl-2-[4-(3-piperidin-1-ylprop-1-ynyl)phenyl]-2H-chromen-6-ol

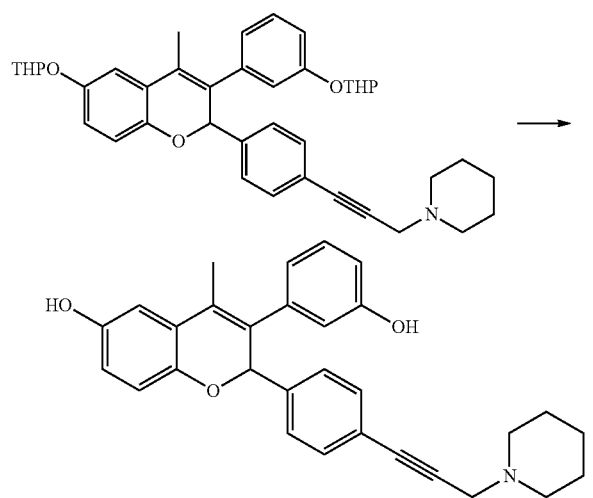

A solution of 1-[3-(4-{4-methyl-6-(tetrahydropyran-2-yloxy)-3-[3-(tetrahydropyran-2-yloxy)phenyl]-2H-chromen-2-yl}phenyl)prop-2-ynyl]piperidine (0.1 g, 0.16 mmol) in a mixture of sulfuric acid (0.05 mL) and methanol (5 mL) was stirred at ambient temperature for 10 minutes. The reaction mixture was made alkaline with saturated solution of sodium bicarbonate and extracted with ethyl acetate. Combined organic layer was dried over anhydrous sodium sulfate and concentrated under reduced pressure to get crude which was purified by column chromatography (silica gel, methanol:dichloromethane 12:88) to get 3-(3-hydroxyphenyl)-4-methyl-2-[4-(3-piperidin-1-ylprop-1-ynyl)phenyl]-2H-chromen-6-ol.

Method-B

Preparation of 3-(3-hydroxyphenyl)-4-methyl-2-[4-((Z)-3-piperidin-1-ylpropenyl) phenyl]-2H-chromen-6-ol (Compound No. 11)

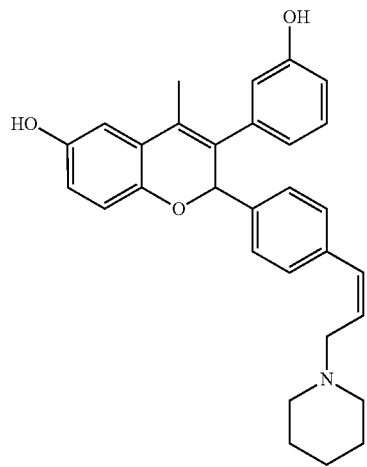 [SMILES: CC1=C(c2cccc(O)c2)C(c2ccc(/C=C\CN3CCCCC3)cc2)Oc2ccc(O)cc21]

Step I: 1-[(Z)-3-(4-{4-Methyl-6-(tetrahydropyran-2-yloxy)-3-[3-(tetrahydropyran-2-yloxy)phenyl]-2H-chromen-2-yl}phenyl)allyl]piperidine

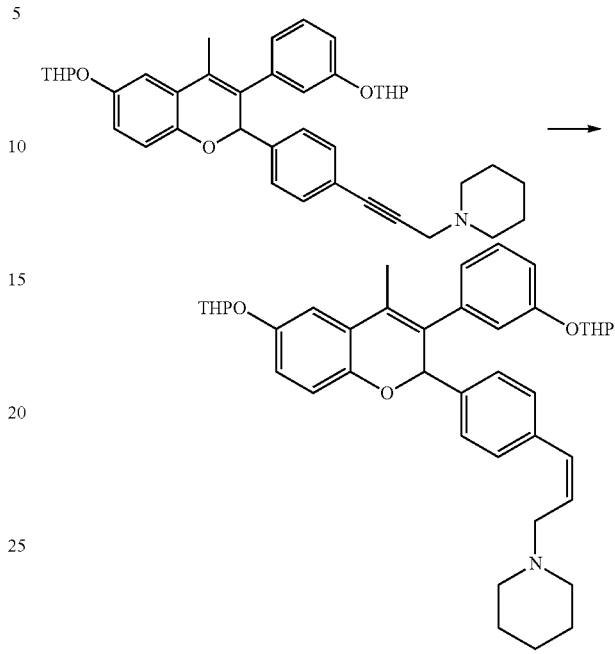

Lindlar catalyst (0.24 g) was added to a solution of 1-[3-(4-{4-methyl-6-(tetrahydropyran-2-yloxy)-3-[3-(tetrahydropyran-2-yloxy)phenyl]-2H-chromen-2-yl}phenyl)prop-2-ynyl]piperidine (0.80 g, 1.29 mmol) (prepared same as per method A step I, II) and quinoline (0.1 g, 12.5% w/w) in ethanol (30 mL). The reaction mixture was stirred under hydrogen atmosphere (70 psi) at ambient temperature for 5 hours. The reaction mixture was filtered and washed with ethanol (15 mL). Filtrate was concentrated under reduced pressure to get the crude which was purified by column chromatography (silica gel, dichloromethane:methanol 97:3) to yield 1-[(Z)-3-(4-{4-methyl-6-(tetrahydropyran-2-yloxy)-3-[3-(tetrahydropyran-2-yloxy)phenyl]-2H-chromen-2-yl}phenyl)allyl]piperidine.

Step II: 3-(3-Hydroxyphenyl)-4-methyl-2-[4-((Z)-3-piperidin-1-ylpropenyl)phenyl]-2H-chromen-6-ol

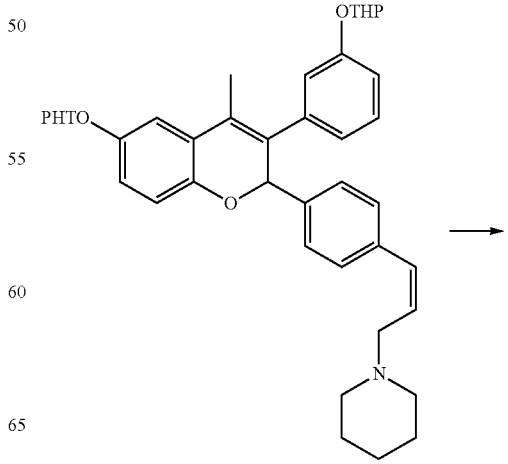

31

-continued

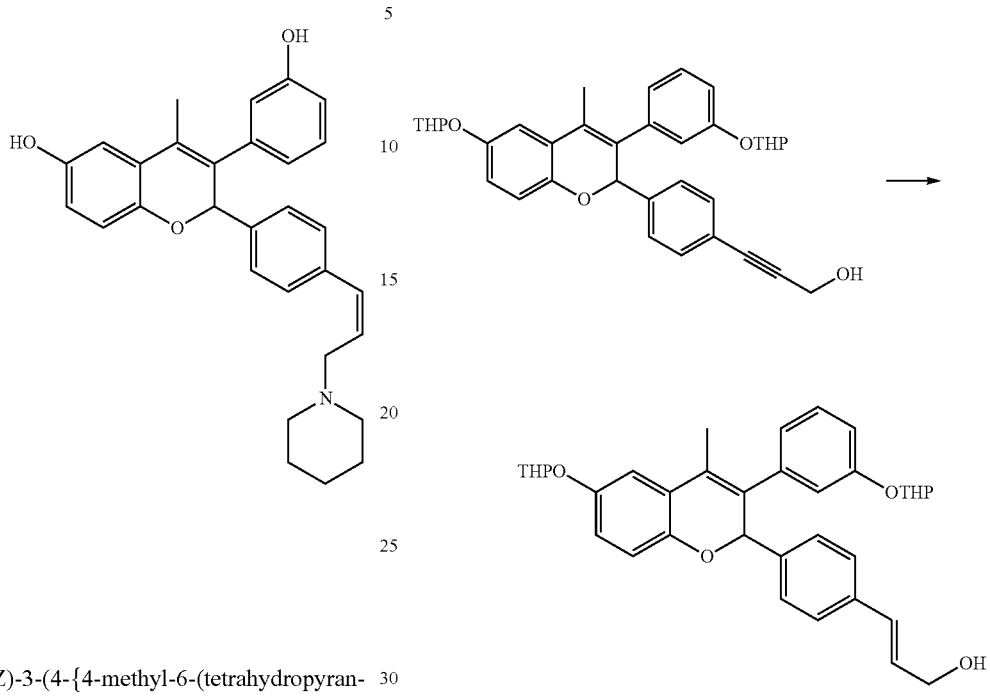

A solution of 1-[(Z)-3-(4-{4-methyl-6-(tetrahydropyran-2-yloxy)-3-[3-(tetrahydropyran-2-yloxy)phenyl]-2H-chromen-2-yl}phenyl)allyl]piperidine (0.28 g, 0.45 mmol) in a mixture of acetic acid (5.6 mL) and water (1.4 mL) was heated at 75° C. for 20 minutes. The reaction mixture was concentrated under reduced pressure and made alkaline with saturated solution of sodium bicarbonate and extracted with ethyl acetate. Combined organic layer was dried over anhydrous sodium sulfate and concentrated under reduced pressure to get residue which was purified by column chromatography (silica gel, methanol:dichloromethane 1:9) to get 3-(3-hydroxyphenyl)-4-methyl-2-[4-((Z)-3-piperidin-1-yl-propenyl)phenyl]-2H-chromen-6-ol.

Method-C

Preparation of 3-(3-hydroxyphenyl)-4-methyl-2-[4-((E)-3-piperidin-1-ylpropenyl) phenyl]-2H-chromen-6-ol (Compound No. 12)

32

Step I: (E)-3-(4-{4-Methyl-6-(tetrahydropyran-2-yloxy)-3-[3-(tetrahydropyran-2-yloxy)phenyl]-2H-chromen-2-yl}phenyl)prop-2-en-1-ol Lithium aluminium hydride (0.35 g, 10.30 mmol) was added to a stirred solution of 3-(4-{4-methyl-6-(tetrahydropyran-2-yloxy)-3-[3-(tetrahydropyran-2-yloxy)phenyl]-2H-chromen-2-yl}phenyl)prop-2-yn-1-ol (1.15 g, 2.08 mmol) (prepared same as method A step-I) in tetrahydrofuran (33 mL) at 0-5° C. and the stirring was continued at ambient temperature for 30 minutes. Reaction mixture was again cooled to 0-5° C., treated with ethyl acetate and aqueous sodium bicarbonate solution and was extracted with ethyl acetate. Combined organic layer was dried over anhydrous sodium sulfate and concentrated under reduced pressure to get crude which was purified by column chromatography (silica gel, ethyl acetate:toluene 17:83) to yield (E)-3-(4-{4-methyl-6-(tetrahydropyran-2-yloxy)-3-[3-(tetrahydropyran-2-yloxy)phenyl]-2H-chromen-2-yl}phenyl)prop-2-en-1-ol.

Step II: 1-[(E)-3-(4-{4-Methyl-6-(tetrahydropyran-2-yloxy)-3-[3-(tetrahydropyran-2-yloxy)phenyl]-2H-chromen-2-yl}phenyl)allyl]piperidine

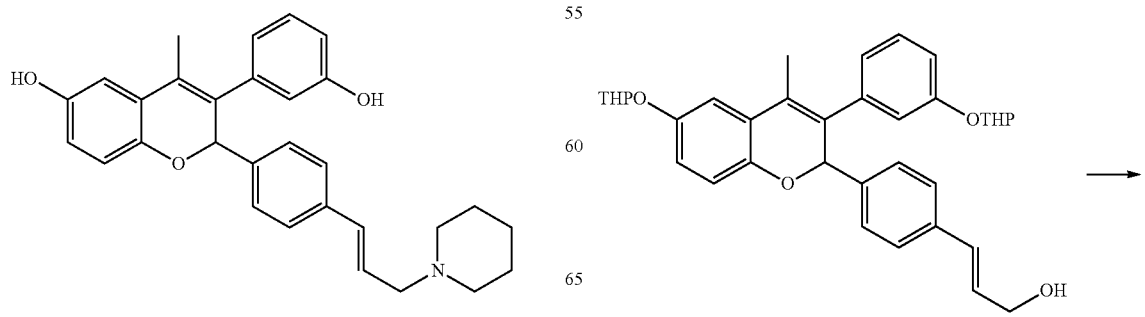

-continued

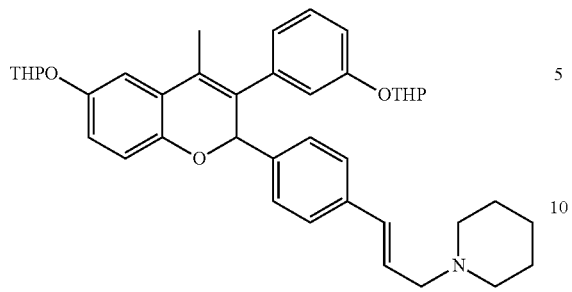

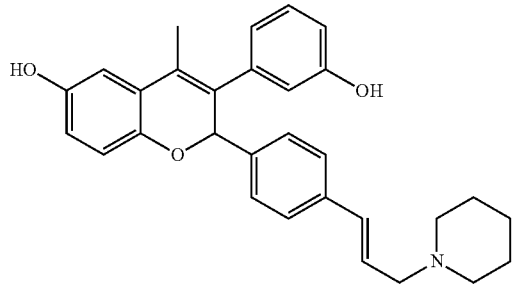 [SMILES: CC1=C(c2cccc(O)c2)C(c2ccc(/C=C/CN3CCCCC3)cc2)Oc2ccc(O)cc21]

A solution of methanesulfonyl chloride (0.098 mL, 1.26 mmol) in dichloromethane (1 mL) was added drop-wise to a stirred solution of (E)-3-(4-{4-methyl-6-(tetrahydropyran-2-yloxy)-3-[3-(tetrahydropyran-2-yloxy)-phenyl]-2H-chromen-2-yl}phenyl)prop-2-en-1-ol (0.58 g, 1.05 mmol) and triethylamine (0.25 mL, 1.80 mmol) in dichloromethane (17 mL) at 0-5° C. The reaction mixture was further stirred at 0-5° C. for 20 minutes. Water was added to the reaction mixture and organic layer was separated. The aqueous layer was extracted with dichloromethane. Combined organic layer was dried over anhydrous sodium sulfate and concentrated under reduced pressure to get methanesulfonic acid (E)-3-(4-{4-methyl-6-(tetrahydropyran-2-yloxy)-3-[3-(tetrahydropyran-2-yloxy)phenyl]-2H-chromen-2-yl}phenyl)allylester.

The solution of methanesulfonic acid (E)-3-(4-{4-methyl-6-(tetrahydropyran-2-yloxy)-3-[3-(tetrahydropyran-2-yloxy)phenyl]-2H-chromen-2-yl}phenyl)allylester in acetonitrile (6 mL) was added to a solution of potassium carbonate (0.432 g, 3.10 mmol) and piperidine (0.27 mL, 2.60 mmol) in acetonitrile (12 mL) at 0-5° C. The reaction mixture was stirred at room temperature for 1.5 hours. Water was added and the mixture was extracted with ethyl acetate. Combined organic layer was dried over anhydrous sodium sulfate and concentrated under reduced pressure to get residue which was purified by column chromatography (silica gel, methanol:dichloromethane 6:94) to yield 1-[(E)-3-(4-{4-methyl-6-(tetrahydropyran-2-yloxy)-3-[3-(tetrahydropyran-2-yloxy)phenyl]-2H-chromen-2-yl}phenyl)allyl]piperidine.

Step III: 3-(3-Hydroxyphenyl)-4-methyl-2-[4-((E)-3-piperidin-1-yl-propenyl)phenyl]-2H-chromen-6-ol

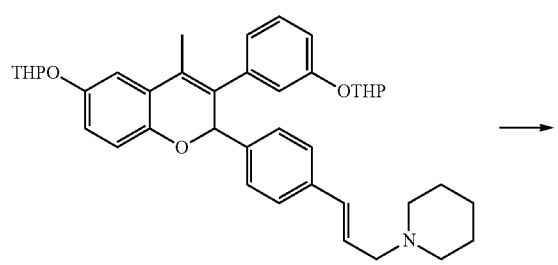

A solution of 1-[(E)-3-(4-{4-methyl-6-(tetrahydropyran-2-yloxy)-3-[3-(tetrahydropyran-2-yloxy)phenyl]-2H-chromen-2-yl}phenyl)allyl]piperidine (0.43 g, 0.70 mmol) in a mixture of sulfuric acid (0.05 mL) and methanol (5 mL) was stirred at ambient temperature for 10 minutes. The reaction mixture was made alkaline with saturated solution of sodium bicarbonate and extracted with ethyl acetate. The combined organic layer was dried over anhydrous sodium sulfate and concentrated under reduced pressure to get residue which was purified by column chromatography (silica gel, methanol:dichloromethane 14:86) to get 3-(3-hydroxyphenyl)-4-methyl-2-[4-((E)-3-piperidin-1-ylpropenyl)phenyl]-2H-chromen-6-ol.

Method-D

Preparation of 3-(3-hydroxyphenyl)-4-methyl-2-(4-{(Z)-3-[9-(4,4,5,5,5-pentafluoro pentylsulfanyl)nonylamino]propenyl}phenyl)-2H-chromen-6-ol (Compound No. 7)

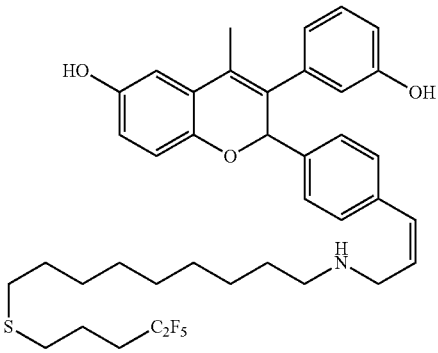

Step I: 2-[3-(4-{4-Methyl-6-(tetrahydropyran-2-yloxy)-3-[3-(tetrahydropyran-2-yloxy) phenyl]-2H-chromen-2-yl}phenyl)prop-2-ynyl]isoindole-1,3-dione

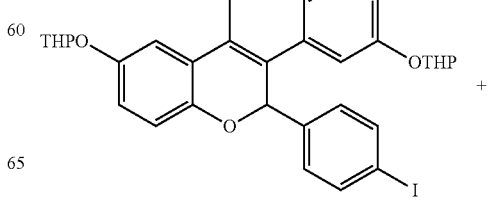

-continued

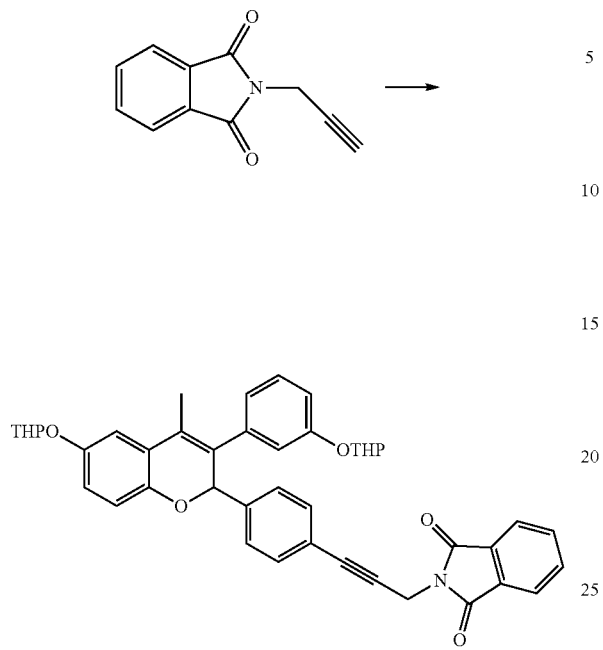

Bis(triphenylphosphine)palladium(II) dichloride (0.045 g, 0.064 mmol) was added to a stirred solution of 2-(4-iodophenyl)-4-methyl-6-(tetrahydropyran-2-yloxy)-3-[3-(tetrahydropyran-2-yloxy)phenyl]-2H-chromene (0.8 g, 1.28 mmol) (prepared as of given in US20140107095A1), 2-prop-2-ynylisoindole-1,3-dione (0.46 g, 2.50 mmol) and cuprous(I) iodide (0.02 g, 0.103 mmol) in a mixture of triethylamine:tetrahydrofuran (26 mL, 1:1) at ambient temperature. After stirring for 1 hour, 2-prop-2-ynyl-isoindole-1,3-dione (2×0.35 g) was added to the reaction mixture and stirring was continued for one more hour. Removal of solvent under reduced pressure yielded a viscous residue which was purified by column chromatography (silica gel, toluene:ethyl acetate 19:1) to get 2-[3-(4-{4-methyl-6-(tetrahydropyran-2-yloxy)-3-[3-(tetrahydropyran-2-yloxy)phenyl]-2H-chromen-2-yl}phenyl)prop-2-ynyl]isoindole-1,3-dione.

Step II: 2-[(Z)-3-(4-{4-Methyl-6-(tetrahydropyran-2-yloxy)-3-[3-(tetrahydropyran-2-yloxy)phenyl]-2H-chromen-2-yl}phenyl)allyl]isoindole-1,3-dione

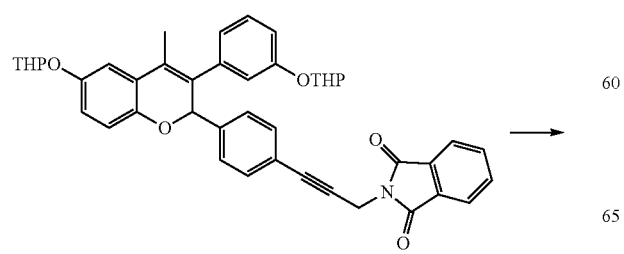

-continued

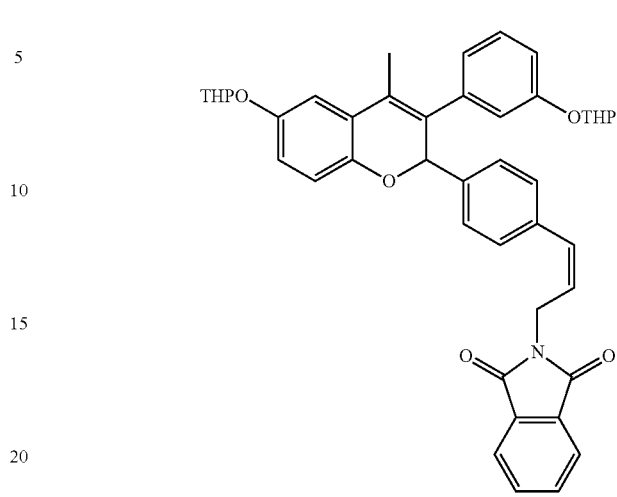

Lindlar catalyst (0.45 g) was added to a stirred solution of 2-[3-(4-{4-methyl-6-(tetrahydropyran-2-yloxy)-3-[3-(tetrahydropyran-2-yloxy)phenyl]-2H-chromen-2-yl}-phenyl) prop-2-ynyl]isoindole-1,3-dione (0.87 g, 1.28 mmol) and quinoline (0.087 g, 10% w/w) in a mixture of ethyl acetate: ethanol (1:1, 34 mL). The reaction mixture was stirred under hydrogen atmosphere (70 psi) at ambient temperature for 24 hours. It was then filtered through celite bed and washed with ethyl acetate. Combined filtrate was concentrated under reduced pressure to get residue which was purified by column chromatography (silica gel, toluene:ethyl acetate 24:1) to get 2-[(Z)-3-(4-{4-methyl-6-(tetrahydropyran-2-yloxy)-3-[3-(tetrahydropyran-2-yloxy)phenyl]-2H-chromen-2-yl}phenyl)allyl]isoindole-1,3-dione.

Step III: (Z)-3-(4-{4-Methyl-6-(tetrahydropyran-2-yloxy)-3-[3-(tetrahydropyran-2-yloxy)phenyl]-2H-chromen-2-yl}phenyl)allylamine

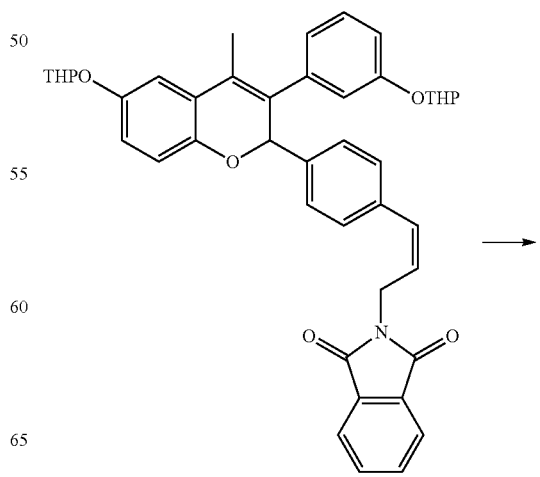

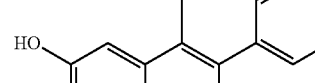

A solution of hydrazine hydrate (0.015 g, 0.31 mmol) in methanol (1 mL) was added to a stirred solution of 2-[(Z)-3-(4-{4-methyl-6-(tetrahydropyran-2-yloxy)-3-[3-(tetrahydropyran-2-yloxy)phenyl]-2H-chromen-2-yl)phenyl)allyl] isoindole-1,3-dione (0.084 g, 0.123 mmol) in tetrahydrofuran (10 mL). The reaction mixture was heated at 65-70° C. for 1.5 hours. Solvent was removed under reduced pressure to get crude which was suspended in diethyl ether and stirred for 10 minutes. It was then filtered and washed with diethyl ether (25 mL). Combined filtrate was concentrated under reduced pressure to get (Z)-3-(4-(4-methyl-6-(tetrahydropyran-2-yloxy)-3-[3-(tetrahydropyran-2-yloxy) phenyl]-2H-chromen-2-yl}-phenyl)allylamine Step IV: [(Z)-3-(4-{4-Methyl-6-(tetrahydropyran-2-yloxy)-3-[3-(tetrahydropyran-2-yloxy)phenyl]-2H-chromen-2-yl}phenyl)allyl]-[9-(4,4,5,5,5-pentafluoropentylsulfanyl)nonyl]amine

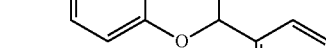

1-Bromo-9-(4,4,5,5,5-pentafluoropentylsulfanyl)nonane (0.036 g, 0.09 mmol) was added to a stirred solution of (Z)-3-(4-{4-methyl-6-(tetrahydropyran-2-yloxy)-3-[3-(tet-rahydropyran-2-yloxy)phenyl]-2H-chromen-2-yl}phenyl) allylamine (0.05 g, 0.09 mmol) and potassium carbonate (0.033 g, 0.243 mmol) in N,N-dimethyl formamide (0.5 mL). The reaction mixture was heated at 85-90° C. for 1.5 hours. Solvent was removed under reduced pressure to get residue which was suspended in ethyl acetate and stirred for 30 minutes. It was then filtered and washed with ethyl acetate. Filtrate was concentrated under reduced pressure to get a crude which was purified by column chromatography (silica gel, methanol:dichloromethane 24:1) to get [(Z)-3-(4-{4-methyl-6-(tetrahydropyran-2-yloxy)-3-[3-(tetrahydropyran-2-yloxy)phenyl]-2H-chromen-2-yl}phenyl)allyl]-[9-(4,4,5,5,5-pentafluoropentylsulfanyl)nonyl]amine.

Step V: 3-(3-Hydroxyphenyl)-4-methyl-2-(4-{(Z)-3-[9-(4,4,5,5,5-pentafluoropentyl sulfanyl)nonylamino]propenyl}phenyl)-2H-chromen-6-ol

A solution of [(Z)-3-(4-{4-methyl-6-(tetrahydropyran-2-yloxy)-3-[3-(tetrahydropyran-2-yloxy)phenyl]-2H-chromen-2-yl}phenyl)allyl]-[9-(4,4,5,5,5-pentafluoropentylsulfanyl) nonyl]amine (0.2 g, 0.23 mmol) in a mixture of sulfuric acid (0.035 mL) and methanol (5 mL) was stirred at room temperature for 10 minutes. The reaction mixture was made alkaline with saturated solution of sodium bicarbonate and extracted with ethyl acetate. Combined organic layer was dried over anhydrous sodium sulfate and concentrated under reduced pressure to get residue which was purified by column chromatography (silica gel, methanol:dichloromethane 8:92) to get 3-(3-hydroxyphenyl)-4-methyl-2-(4-{(Z)-3-[9-(4,4,5,5,5-pentafluoropentylsulfanyl)nonylamino] propenyl}phenyl)-2H-chromen-6-ol

39
Method-E

Preparation of 2,2-Dimethylpropionic Acid 3-[3-(2,2-dimethylpropionyloxy)phenyl]-4-methyl-2-{4-[(Z)-3-((R)-3-methylpyrrolidin-1-yl)propenyl]phenyl}-2H-chromen-6-yl ester (Compound No. 19)

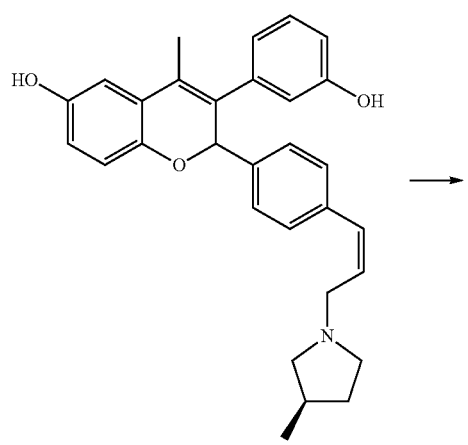

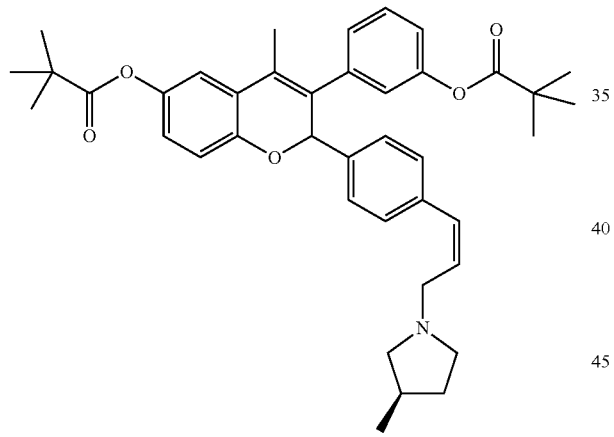

Pivoloyl chloride (0.054 mL, 0.44 mmol) was added to a stirred solution of 3-(3-hydroxyphenyl)-4-methyl-2-{4-[(Z)-3-((R)-3-methylpyrrolidin-1-yl)propenyl]phenyl}-2H-chromen-6-ol (0.09 g, 0.2 mmol) (prepared same as method B) and triethylamine (0.069 mL, 0.50 mmol) in dichloromethane (6 mL) at 0° C. under nitrogen atmosphere. The reaction mixture was stirred at ambient temperature for 2.5 hours. It was then treated with saturated sodium bicarbonate and organic layer was separated. The aqueous solution was extracted with dichloromethane. The combined organic layer was dried over sodium sulfate and concentrated under reduced pressure to get residue which was purified by column chromatography (silica gel, dichloromethane:methanol 19:1) to yield 2,2-dimethylpropionicacid-3-[3-(2,2-dimethyl propionyloxy)phenyl]-4-methyl-2-{4-[(Z)-3-((R)-3-methylpyrrolidin-1-yl)propenyl]phenyl}-2H-chromen-6-ylester.

40
Method-F

Preparation of (R)-1-((Z)-3-{4-[6-methoxy-3-(3-methoxyphenyl)-4-methyl-2H-chromen-2-yl]phenyl}allyl)-3-methylpyrrolidine (Compound No. 20)

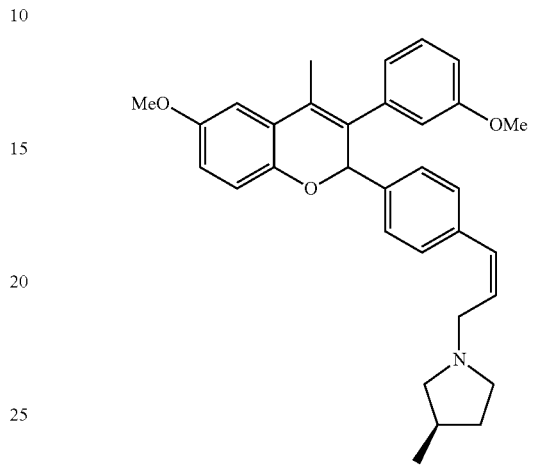

Step I: 3-(3-Hydroxyphenyl)-2-(4-iodophenyl)-4-methyl-2H-chromen-6-ol

A solution of 2-(4-iodophenyl)-4-methyl-6-tetrahydropyran-2-yloxy)-3-[3-(tetrahydropyran-2-yloxy)phenyl]-2H-chromene (1.0 g, 1.60 mmol) (prepared same as method A) in sulfuric acid (0.1 ml) and methanol (10 ml) was stirred for 20 minutes at ambient temperature. Aqueous solution of sodium bicarbonate was added and extracted with ethyl acetate. Combined organic layer was washed with water and dried over anhydrous sodium sulfate. It was then concentrated under reduced pressure to get residue which was purified by column chromatography (silica gel, n-hexane:ethyl acetate 50:50) to yield 3-(3-hydroxyphenyl)-2-(4-iodophenyl)-4-methyl-2H-chromen-6-ol.

Step II: 2-(4-Iodophenyl)-6-methoxy-3-(3-methoxyphenyl)-4-methyl-2H-chromene

Step IV: (R)-1-((Z)-2-{4-[6-Methoxy-3-(3-methoxyphenyl)-4-methyl-2H-chromen-2-yl]phenyl}vinyl)-3-methylpyrrolidine

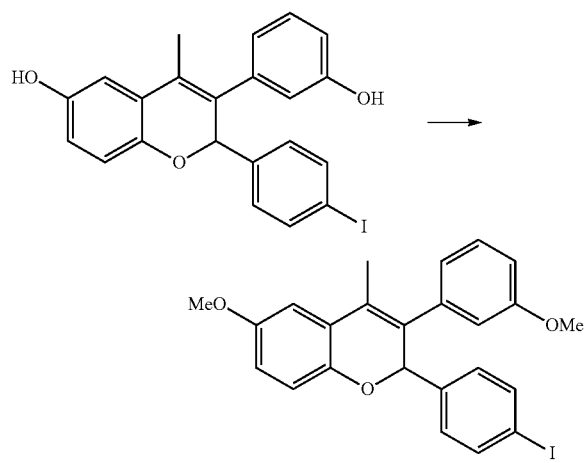

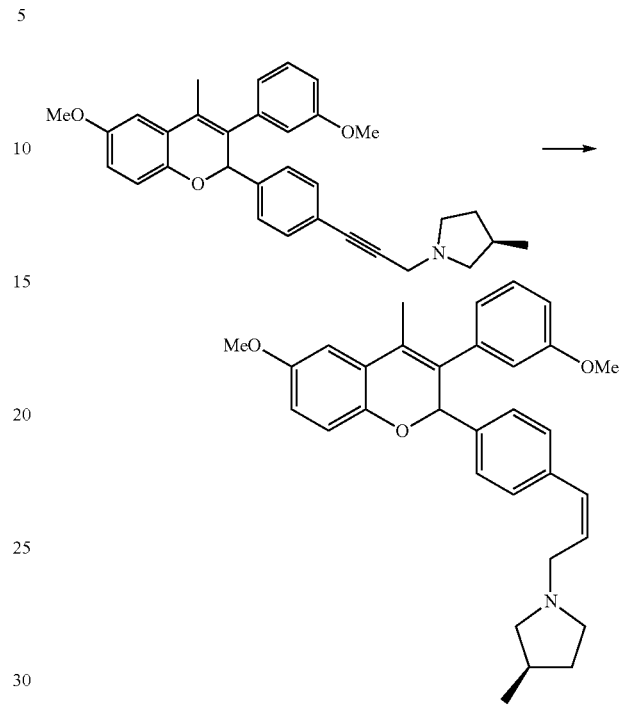

Methyl iodide (0.82 mL, 13.1 mmol) was added to a stirred solution of 3-(3-hydroxyphenyl)-2-(4-iodophenyl)-4-methyl-2H-chromen-6-ol (0.6 g, 1.31 mmol) and potassium carbonate (0.54 g, 3.94 mmol) in N,N-dimethylformamide (6.0 mL) at 5-10° C. The reaction mixture was stirred at ambient temperature for 4 hours. Water was added and extracted with ethyl acetate. Combined organic layer was washed with water and dried over anhydrous sodium sulfate. It was then concentrated under reduced pressure to get crude which was purified by column chromatography (silica gel, n-hexane:ethyl acetate 8:2) to give 2-(4-iodophenyl)-6-methoxy-3-(3-methoxyphenyl)-4-methyl-2H-chromene.

Step III: (R)-1-(3-{4-[6-Methoxy-3-(3-methoxyphenyl)-4-methyl-2H-chromen-2-yl]phenyl}prop-2-ynyl)-3-methylpyrrolidine (R)-1-((Z)-2-{4-[6-methoxy-3-(3-methoxyphenyl)-4-methyl-2H-chromen-2-yl]phenyl}vinyl)-3-methylpyrrolidine prepared same as that of step-I of method B using (R)-1-(3-{4-[6-Methoxy-3-(3-methoxyphenyl)-4-methyl-2H-chromen-2-yl]phenyl}prop-2-ynyl)-3-methylpyrrolidine.

Method-G

Preparation of 3-(3-Methoxy phenyl)-4-methyl-2-{4-[(Z)-3-((R)-3-methyl pyrrolidin-1-yl)propenyl]phenyl}-2H-chromen-6-ol (Compound No. 28)

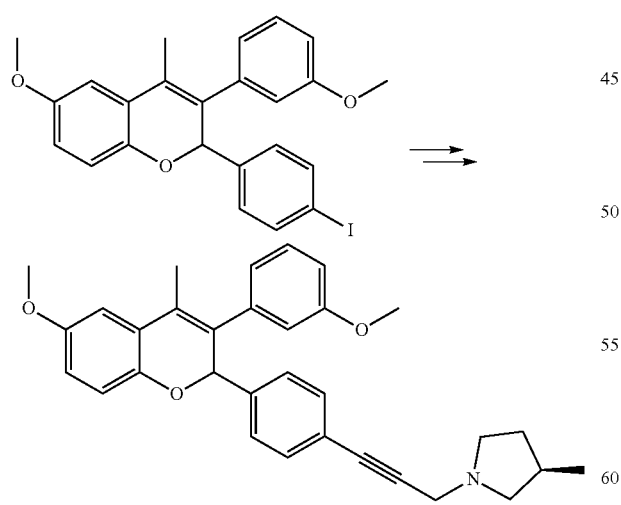

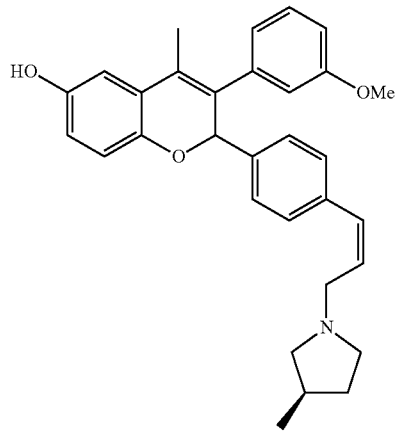 [SMILES: COc1cccc(C2=C(C)c3cc(O)ccc3OC2c2ccc(/C=C\CN3CC[C@@H](C)C3)cc2)c1]

(R)-1-(3-{4-[6-Methoxy-3-(3-methoxyphenyl)-4-methyl-2H-chromen-2-yl]phenyl}prop-2-ynyl)-3-methylpyrrolidine prepared same as that of step-I,II of method A using 2-(4-iodophenyl)-6-methoxy-3-(3-methoxyphenyl)-4-methyl-2H-chromene

Step I: 2-Hydroxy-4-(tetrahydropyran-2-yloxy)benzoic Acid

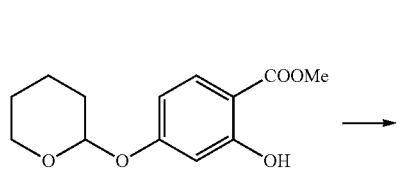

Aqueous sodium hydroxide (3.5 mL, 10%) was added to the stirred solution of 2-hydroxy-4-(tetrahydropyran-2-yloxy)-benzoic acid methyl ester (0.5 g, 1.98 mmol) in methanol (10 mL) at ambient temperature and heated to 50° C. for 4 hours. Solvent was removed under reduced pressure. Water was added to it and extracted with (ethyl acetate: n-hexane, 2:8). Aqueous layer was made acidic with acetic acid at 0-5° C. and extracted with ethyl acetate. Combined organic layer was dried over anhydrous sodium sulfate and concentrated under reduced pressure to get 2-hydroxy-4-(tetrahydropyran-2-yloxy)benzoic acid.

Step II: 2-Hydroxy-N-methoxy-N-methyl-4-(tetrahydropyran-2-yloxy)benzamide

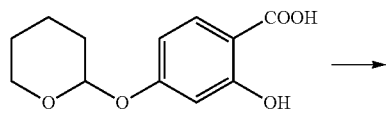

Aqueous alkaline solution of N,O-dimethyl hydroxylamine hydrochloride (0.12 g, 1.3 mmol) in tetrahydrofuran (2 mL) was added to a stirred solution of 1-Hydroxy benzotriazole (0.17 g, 1.3 mmol), 1-ethyl-3-(3-dimethylaminopropyl)carbodiimide hydrochloride (0.24 g. 1.3 mmol) and 2-hydroxy-4-(tetrahydropyran-2-yloxy)benzoic acid (0.2 g, 0.8 mmol) in tetrahydrofuran (3 mL) at room temperature and stirred for 2 hours. Water (10 mL) was added to the reaction mixture and extracted with ethyl acetate. Combined organic layer was dried over anhydrous sodium sulfate and concentrated under reduced pressure to get crude which was purified by column chromatography (silica gel n-hexane: ethyl acetate 8:2) to get 2-hydroxy-N-methoxy-N-methyl-4-(tetrahydropyran-2-yloxy)benzamide.

Step III: 1-[2-Hydroxy-4-(tetrahydropyran-2-yloxy)phenyl]-2-(3-methoxyphenyl) ethanone

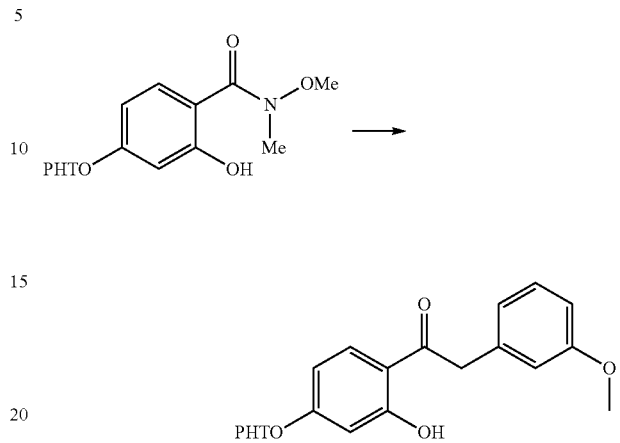

A solution of 3-methoxybenzyl chloride (1.10 g, 7.12 mmol) in diethyl ether (7.5 mL) was added to a stirred mixture of magnesium (0.216 g, 8.90 mmol), iodine (crystals) and 1,2-dibromoethane (0.1 mL) in diethyl ether (7.5 mL) as dropwise manner at 45-50° C. The reaction mixture was refluxed for 1 hour. A solution of 2-hydroxy-N-methoxy-N-methyl-4-(tetrahydropyran-2-yloxy)benzamide (0.5 g, 1.78 mmol) in tetrahydrofuran (5 mL) was added dropwise to the reaction mixture at 0° C. followed by 1 hour room temperature stirring. Saturated ammonium chloride was added to the reaction mixture at 0-5° C. and extracted with ethyl acetate. Combined organic layer was dried over anhydrous sodium sulfate and concentrated under reduced pressure to get crude which was purified by column chromatography (silica gel, ethyl acetate:n-hexane 2:8) to get 1-[2-hydroxy-4-(tetrahydropyran-2-yloxy)phenyl]-2-(3-methoxyphenyl)ethanone.

Step IV: 2-(4-Iodophenyl)-3-(3-methoxyphenyl)-4-methyl-7-(tetrahydropyran-2-yloxy)-2H-chromene

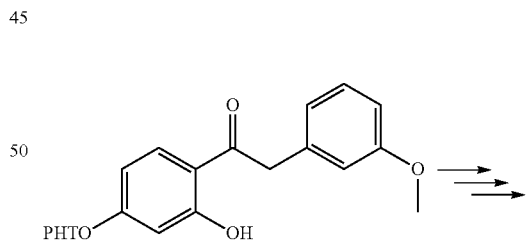

2-(4-Iodophenyl)-3-(3-methoxyphenyl)-4-methyl-7-(tetrahydropyran-2-yloxy)-2H-chromene prepared as per the process given in US20140107095A1 using 1-[2-hydroxy-4-(tetrahydropyran-2-yloxy)phenyl]-2-(3-methoxyphenyl)ethanone.

Step V: 3-{4-[3-(3-Methoxyphenyl)-4-methyl-7-(tetrahydropyran-2-yloxy)-2H-chromen-2-yl]phenyl}prop-2-yn-1-ol

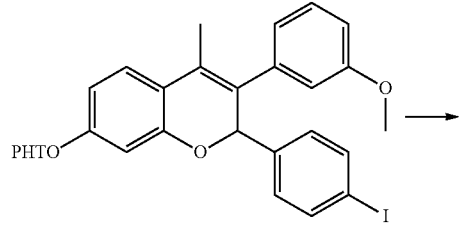

3-{4-[3-(3-Methoxyphenyl)-4-methyl-7-(tetrahydropyran-2-yloxy)-2H-chromen-2-yl]phenyl}prop-2-yn-1-ol was prepared same as that of step-I of method A using 2-(4-Iodophenyl)-3-(3-methoxyphenyl)-4-methyl-7-(tetrahydropyran-2-yloxy)-2H-chromene.

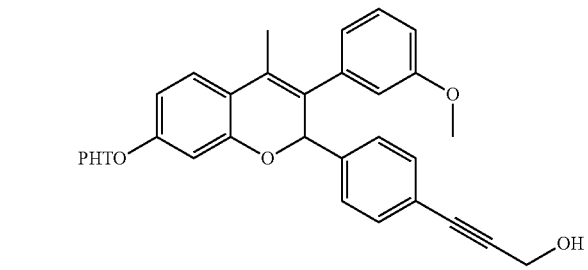

Step VI: 3-(3-Methoxyphenyl)-4-methyl-2-{4-[(Z)-3-((R)-3-methylpyrrolidin-1-yl)propenyl]phenyl}-2H-chromen-7-ol

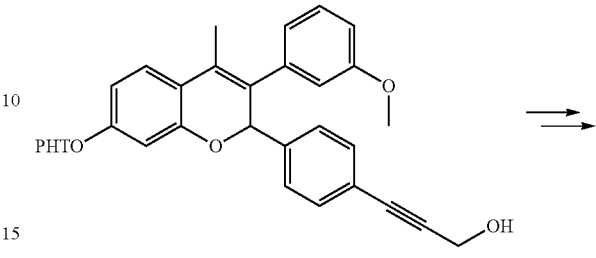

3-(3-Methoxyphenyl)-4-methyl-2-{4-[(Z)-3-((R)-3-methylpyrrolidin-1-yl)propenyl]phenyl}-2H-chromen-7-ol was prepared same as that of method B using 3-{4-[3-(3-Methoxyphenyl)-4-methyl-7-(tetrahydropyran-2-yloxy)-2H-chromen-2-yl]phenyl}prop-2-yn-1-o Method-J Preparation of Acetic Acid 3-(6-acetoxy-2-{4-[(E)-3-(9-fluorononylamino)propenyl]phenyl}-4-methyl-2H-chromen-3-yl)phenyl Ester (Compound No. 74)

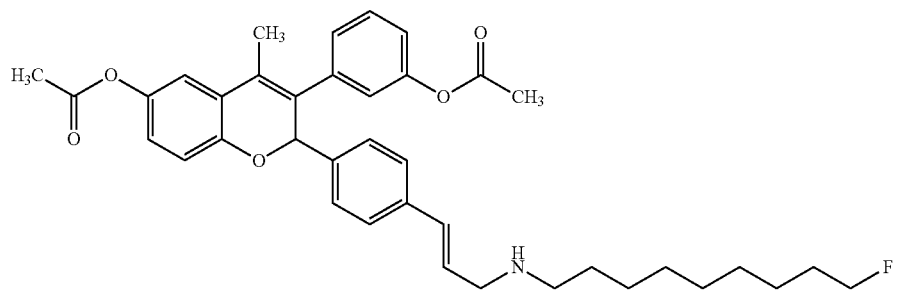 [SMILES: CC(=O)Oc1cccc(C2=C(C)c3cc(OC(C)=O)ccc3OC2c2ccc(/C=C/CNCCCCCCCCCF)cc2)c1]

Step I: (9-Fluorononyl)-((E)-3-{4-[6-hydroxy-3-(3-hydroxyphenyl)-4-methyl-2H-chromen-2-yl]phenyl}allyl)carbamic Acid Tert-Butyl Ester

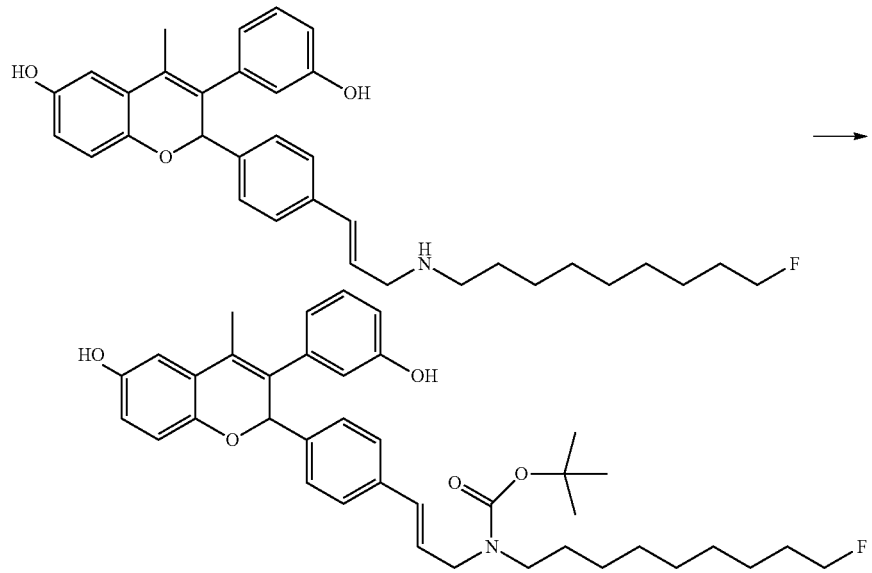

Di-tert-butyl dicarbonate (0.19 g, 0.85 mmol) was added to a stirred solution of 2-{4-[(E)-3-(9-fluorononylamino)propenyl]phenyl}-3-(3-hydroxyphenyl)-4-methyl-2H-chromen-6-ol (0.41 g, 0.77 mmol) and triethylamine (0.09 g, 0.93 mmol) in dichloromethane (15 mL) at ambient temperature and was allowed to stirred at same temperature for 40 minutes. Solvent was removed under reduced pressure to get crude which was purified by column chromatography (silica gel, n-hexane:ethyl acetate, 6:4) to get (9-fluorononyl)-((E)-3-{4-[6-hydroxy-3-(3-hydroxyphenyl)-4-methyl-2H-chromen-2-yl]phenyl}allyl)carbamic acid tert-butyl ester.

Step II: Acetic Acid 3-[6-acetoxy-2-(4-{(E)-3-[tert-butoxycarbonyl-(9-fluorononyl)amino]propenyl}phenyl)-4-methyl-2H-chromen-3-yl]phenyl Ester

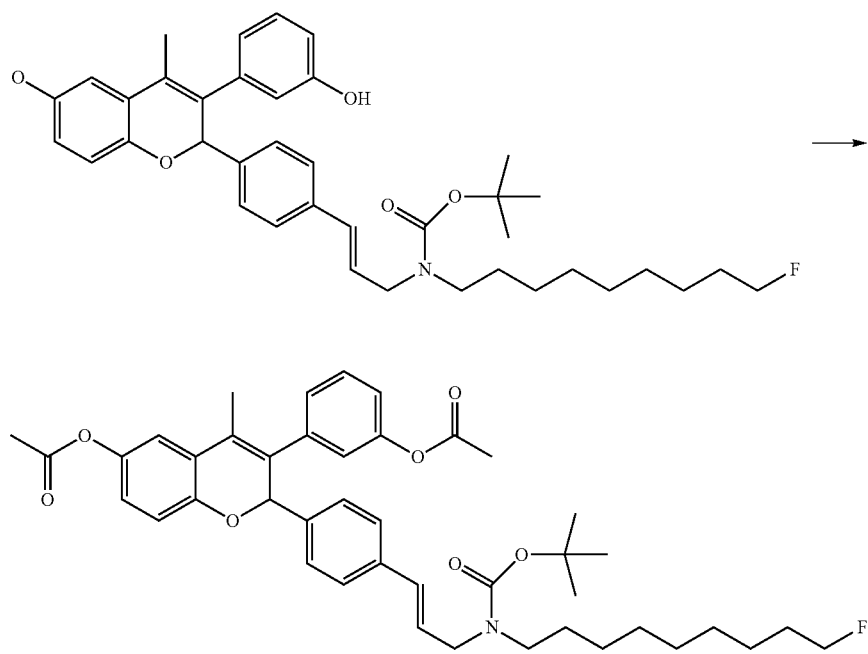

Acetyl chloride (0.04 g, 0.52 mmol) was added to a stirred solution of (9-fluorononyl)-((E)-3-(4-[6-hydroxy-3-(3-hydroxyphenyl)-4-methyl-2H-chromen-2-yl]phenyl)allyl)carbamic acid tert-butyl ester (0.11 g, 0.17 mmol) and triethylamine (0.07 g, 0.70 mmol) in dichloromethane (5 mL) at 0-5° C. and was stirred at ambient temperature for 1 hour. Saturated sodium bicarbonate solution was added to the reaction mixture and was extracted with dichloromethane. Combined organic layer was dried over anhydrous sodium sulfate and concentrated under reduced pressure to get crude which was purified by column chromatography (silica gel n-hexane:ethyl acetate 8:2) to yield acetic acid 3-[6-acetoxy-2-(4-{(E)-3-[tert-butoxycarbonyl-(9-fluorononyl)amino]propenyl}phenyl)-4-methyl-2H-chromen-3-yl]phenyl ester.

Step III: Acetic acid 3-(6-acetoxy-2-{4-[(E)-3-(9-fluorononylamino)propenyl]phenyl}-4-methyl-2H-chromen-3-yl)phenyl Ester

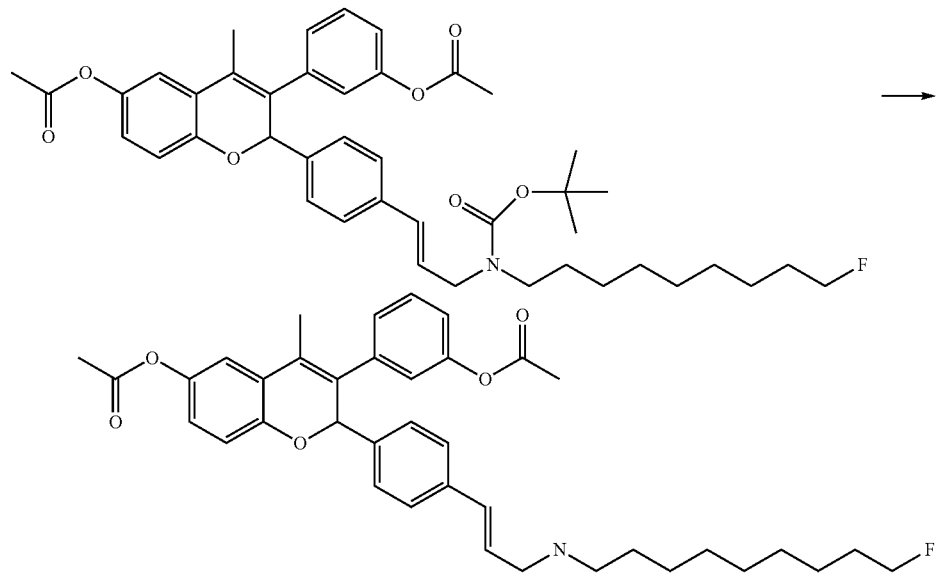

Zinc bromide (0.15 g, 0.67 mmol) was added to a stirred solution of acetic acid 3-[6-acetoxy-2-(4-{(E)-3-[tert-butoxycarbonyl-(9-fluorononyl)amino]propenyl}phenyl)-4-methyl-2H-chromen-3-yl]phenyl ester (0.12 g, 0.17 mmol) in dichloromethane (3 mL) at ambient temperature and was allowed to stirred at same temperature for 4 hours. Water was added to reaction mixture and extracted with dichloromethane. Combined organic layer was dried over anhydrous sodium sulfate and concentrated under reduced pressure to get crude which was purified by column chromatography (silica gel, dichloromethane:methanol, 8:2) to yield acetic acid 3-(6-acetoxy-2-{4-[(E)-3-(9-fluorononylamino)propenyl]phenyl}-4-methyl-2H-chromen-3-yl) phenyl ester.

Table 2 provides some of the representative compounds prepared as per the general process.

TABLE 2

| Comp # | Chemical name | NMR |
|---|---|---|
| 1 | 3-(3-Hydroxyphenyl)-4-methyl-2-[4-((Z)-3-methylamino propenyl)phenyl]-2H-chromen-6-ol | ($d_6$-DMSO, 400 MHz); 2.10 (s, 3H); 2.33 (s, 3H); 3.34-3.46 (m, 3H); 5.72 (dt, $J_1$ = 11.88 Hz, $J_2$ = 6.32 Hz, 1H); 5.98 (s, 1H); 6.45 (d, J = 11.92 Hz, 1H); 6.53-6.60 (m, 2H); 6.69-6.74 (m, 2H); 6.77 (d, J = 7.72 Hz, 1H); 6.80 (d, J = 2.12 Hz, 1H); 7.17-7.24 (m, 3H); 7.33 (d, J = 8.24 Hz, 2H); 9.04 (s, 1H); 9.52 (s, 1H) |
| 2 | 2-[4-((Z)-3-Dimethylamino propenyl)phenyl]-3-(3-hydroxyphenyl)-4-methyl-2H-chromen-6-ol | ($d_6$-DMSO, 400 MHz); 2.04 (s, 3H); 2.19 (s, 6H); 3.16-3.25 (m, 2H); 5.69 (dt, $J_1$ = 11.95 Hz, $J_2$ = 6.30 Hz, 1H); 5.93 (s, 1H); 6.44 (d, J = 12.00 Hz, 1H); 6.48-6.55 (m, 2H); 6.62-6.70 (m, 2H); 6.70-6.79 (m, 2H); 7.10-7.21 (m, 3H); 7.28 (d, J = 8.20 Hz, 2H); 8.98 (s, 1H); 9.46 (s, 1H) |

TABLE 2-continued

| Comp # | Chemical name | NMR |
|---|---|---|
| 3 | 2-[4-((Z)-3-Dodecylamino propenyl)phenyl]-3-(3-hydroxyphenyl)-4-methyl-2H-chromen-6-ol | ($d_6$-DMSO, 400 MHz); 0.91 (t, J = 7.00 Hz, 3H); 1.22-1.35 (br m, 18H); 1.40-1.50 (br m, 2H); 2.10 (s, 3H); 2.64 (t, J = 7.36 Hz, 2H); 3.56 (d, J = 5.00 Hz, 2H); 5.74 (dt, $J_1$ = 12.32 Hz; 1H); 5.98 (s, 1H); 6.50 (d, J = 11.92 Hz, 1H); 6.53-6.61 (m, 2H); 6.68-6.75 (m, 2H); 6.77 (d, J = 7.64 Hz, 1H); 6.81 (d, J = 1.84 Hz, 1H); 7.16-7.25 (m, 3H); 7.34 (d, J = 8.20 Hz, 2H); 8.98-9.10 (br s, 1H); 9.46-9.62 (br s, 1H); one exchangeable proton |
| 4 | 2-[4-((E)-3-Dodecylamino propenyl)phenyl]-3-(3-hydroxyphenyl)-4-methyl-2H-chromen-6-ol | ($d_6$-DMSO, 400 MHz); 0.90 (t, J = 6.52 Hz, 3H); 1.23-1.38 (br m, 18H); 1.53-1.62 (br m, 2H); 2.09 (s, 3H); 2.83 (t, J = 7.45 Hz 2H); 3.61-3.67 (m, 2H); 5.97 (s, 1H); 6.26 (dt, $J_1$ = 15.89 Hz, $J_2$ = 6.92 Hz, 1H); 6.54-6.60 (m, 2H); 6.66-6.79 (m, 4H); 6.81 (br s, 1H); 7.19 (t, J = 7.80 Hz, 1H); 7.32 (d, J = 8.28 Hz, 2H); 7.38 (d, J = 8.40 Hz, 2H); 9.05 (s, 1H); 9.53 (s, 1H); one exchangeable proton |
| 5 | 2-{4-[(Z)-34(E)-2,7-Dimethylocta-2,6-dienylamino)propenyl]phenyl}-3-(3-hydroxyphenyl)-4-methyl-2H-chromen-6-ol | ($d_6$-DMSO, 400 MHz); 1.59 (s, 6H); 1.66 (s, 3H); 1.92-2.01 (m, 2H); 2.01-2.07 (m, 2H); 2.09 (s, 3H); 3.47 (d, J = 7.08 Hz, 2H); 3.73 (d, J = 5.80 Hz, 2H); 5.02-5.10 (br t, 1H); 5.13-5.21 (br t, 1H); 5.70-5.77 (m, 1H); 5.99 (s, 1H); 6.52-6.57 (m, 2H); 6.61-6.64 (br d, 1H); 6.68-6.80 (m, 4H); 7.19 (t, J = 7.72 Hz, 1H); 7.21 (d, J = 8.16 Hz, 2H); 7.34 (d, J = 8.12 Hz, 2H); 9.05 (s, 1H); 9.54 (s, 1H); one exchangeable proton |
| 6 | 2-{4-[(Z)-3-(2-Dimethyl aminoethylamino)propenyl] phenyl}-3-(3-hydroxy phenyl)-4-methyl-2H-chromen-6-ol | ($d_6$-DMSO, 400 MHz); 2.09 (s, 3H); 2.14 (s, 6H); 2.31 (t, J = 6.30 Hz, 2H); 2.58-2.63 (in, 2H); 3.41-3.46 (m, 2H); 5.73 (dt, $J_1$ = 11.85 Hz, $J_2$ = 6.30 Hz, 2H); 5.97 (s, 1H); 6.42 (d, J = 11.85 Hz, 1H); 6.52-6.59 (m, 2H); 6.68-6.73 (m, 2H); 6.77 (d, J = 7.55 Hz, 1H); 6.80 (d, J = 2.25 Hz, 1H); 7.18-7.23 (m, 3H); 7.32 (d, J = 8.05 Hz, 2H); 9.02 (s, 1H); 9.51 (s, 1H); one exchangeable proton |
| 7 | 3-(3-Hydroxyphenyl)-4-methyl-2-(4-{(Z)-3-[9-(4,4,5,5,5-pentafluoropentylsulfanyl)nonylamino]propenyl}phenyl)-2H-chromen-6-ol | ($d_6$-DMSO, 400 MHz); 1.23-1.34 (br s, 8H); 1.33-1.43 (br m, 2H); 1.47-1.61 (br m, 4H); 1.81 (quintet, J = 6.32 Hz, 2H); 2.10 (s, 3H); 2.27-2.45 (br m, 2H); 2.64 (t, J = 7.12 Hz, 2H); 2.79 (t, J = 7.76 Hz 2H); 3.74 (d, J = 5.24 Hz, 2H); 5.75 (dt, $J_1$ = 11.84 Hz; $J_2$ = 6.32 Hz, 1H); 6.00 (s, 1H); 6.54-6.58 (m, 2H); 6.62 (d, J = 12.08 Hz, 1H); 6.70-6.84 (m, 4H); 7.20 t, J = 7.80 Hz, 1H); 7.24 (d, J = 8.20 Hz, 2H); 7.36 (d, J = 8.20 Hz, 2H); 9.05 (s, 1H); 9.54 (s, 1H); two protons are merged between 2.50-2.60, one exchangeable proton |
| 8 | 3-(3-Hydroxyphenyl)-4-methyl-2-(4-{(E)-3-[9-(4,4,5,5,5-pentafluoro pentylsulfanyl)nonylamino] propenyl}phenyl)-2H-chromen-6-ol | ($d_6$-DMSO, 400 MHz); 1.24-1.34 (br s, 8H); 1.34-1.43 (br m, 2H); 1.55 (quintet, J = 7.25 Hz, 4H); 1.81 (quintet, J = 7.70 Hz, 2H); 2.09 (s, 3H); 2.28-2.44 (br m, 2H); 2.64 (t, J = 7.15 Hz, 2H); 2.77 (t, J = 7.35 Hz 2H); 3.57 (d, J = 6.50 Hz, 2H); 5.96 (s, 1H); 6.28 (dt, $J_1$ = 15.85 Hz; $J_2$ = 6.70 Hz; 1H); 6.52-6.58 (m, 2H); 6.66 (d, J = 15.95 Hz, 1H); 6.68-6.77 (m, 3H); 6.81 (s, 1H); 7.19 (t, J = 7.85 Hz, 1H); 7.32 (d, J = 8.25 Hz, 2H); 7.36 (d, J = 8.30 Hz, 2H); 9.05 (s, 1H); 9.52 (s, 1H); two protons are merged between 2.50-2.60, one exchangeable proton |
| 9 | 3-(3-Hydroxyphenyl)-4-methyl-2-{4-[(Z)-3-((R)-3-methylpyrrolidin-1-yl)propenyl]phenyl}-2H-chromen-6-ol | ($d_6$-DMSO, 400 MHz); 1.0 (d, J = 6.76 Hz, 3H); 1.23-1.33 (m, 3H); 1.91-2.02 (m, 1H); 2.09 (s, 3H); 2.14-2.25 (m, 1H); 2.59-2.68 (br m, 1H); 2.74-2.83 (br t, 1H); 3.3-3.37 (br d, 2H); 5.74-5.82 (m, 1H); 5.97 (s, 1H); 6.41-6.47 (br d, 1H); 6.55-6.58 (m, 2H); 6.69-6.75 (m, 2H); 6.76-6.82(m, 2H); 7.17-7.25 (m, 3H); 7.33 (d, J = 8.24 Hz, 2H); 9.03 (s, 1H); 9.52 (s, 1H) |
| 10 | 3-(3-Hydroxyphenyl)-4-methyl-2-{4-[(E)-3-((R)-3-methylpyrrolidin-1-yl) propenyl]phenyl}-2H-chromen-6-ol | ($d_6$-DMSO, 400 MHz); 1.01 (d, J = 6.72 Hz, 3H); 1.27-1.33 (m, 3H); 1.93-2.03 (m, 1H); 2.09 (s, 3H); 2.15-2.25 (m, 1H); 2.60-2.68 (br m, 1H); 2.74-2.83 (br t, 1H); 3.23 (d, J = 5.16 Hz, 2H); 5.94 (s, 1H); 6.26-6.36 (m, 1H); 6.50 (d, J = 16.05 Hz, 1H); 6.55 (s, 2H); 6.67-6.83 (m, 4H); 7.19 (t, J = 7.80 Hz, 1H); 7.28 (d, J = 8.28 Hz, 2H); 7.35 (d, J = 8.28 Hz, 2H); 9.02 (s, 1H); 9.51 (s, 1H) |
| 11 | 3-(3-Hydroxyphenyl)-4-methyl-2-[4-((Z)-3-piperidin-1-ylpropenyl) phenyl]-2H-chromen-6-ol | ($d_6$-DMSO, 400 MHz); 1.32-1.46 (br m, 2H); 1.46-1.59 (m, 4H); 2.10 (s, 3H); 2.26-2.46 (br m, 4H); 3.17 (dd, $J_1$ = 6.24 Hz, $J_2$ = 1.76 Hz, 2H); 5.75 (dt, $J_1$ = 12.21 Hz, $J_2$ = 6.25 Hz, 1H); 6.46 (d, J = 12.04 Hz, 1H); 6.53-6.62 (m, 1H); 6.69-6.75 (m, 2H); 6.78 (d, J = 7.68 Hz, 2H); 6.80 (d, J = 2.28 Hz, 2H); 7.17-7.26 (m, 3H); 7.33 (d, J = 8.24 Hz, 2H); 8.90-9.20 (br s, 1H); 9.38-9.70 (br s, 1H) |
| 12 | 3-(3-Hydroxyphenyl)-4-methyl-2-[4-((E)-3-piperidin-1-yl propenyl}phenyl]-2H-chromen-6-ol | ($d_6$-DMSO, 400 MHz); 1.37-1.47 (br s, 2H); 1.50-1.62 (br s, 4H); 2.09 (s, 3H); 2.34-2.53 (br m, 4H); 3.05-3.22 (br s, 2H); 5.95 (s, 1H); 6.28 (dt, $J_1$ = 15.89 Hz, $J_2$ = 6.68 Hz, 1H); 6.51 (d, J = 16.40 Hz, 1H); 6.54-6.58 (m, 2H); 6.67-6.83 (m, 4H); 7.19 (t, J = 7.80 Hz, 1H); 7.28 (d, J = 8.20 Hz, 2H); 7.36 (d, J = 8.20 Hz, 2H); 9.03 (s, 1H); 9.51 (s, 1H) |
| 13 | 3-(3-Hydroxyphenyl)-4-methyl-2-[4((Z)-3-morpholin-4-ylpropenyl) phenyl]-2H-chromen-6-ol | ($d_6$-DMSO, 400 MHz); 2.10 (s, 3H); 2.34-2.44 (br s, 4H); 3.18-3.26 (m, 2H); 3.59 (t, J = 4.44 Hz, 4H); 5.76 (dt, $J_1$ = 12.20 Hz, $J_2$ = 6.24 Hz, 1H); 5.98 (s, 1H); 6.49 (d, J = 12.08 Hz, 1H); 6.53-6.61 (m, 2H); 6.67-6.84 (m, 4H); 7.15-7.27 (m, 3H); 7.33 (d, J = 8.24 Hz, 2H); 9.03 (s, 1H); 9.51 (s, 1H) |
| 14 | 3-(3-Hydroxyphenyl)-4-methyl-2-{4-[(Z)-3-(4-methylpiperazin-1-yl) propenyl]phenyl}-2H-chromen-6-ol | ($d_6$-DMSO, 400 MHz); 2.09 (s, 3H); 2.25 (s, 3H); 2.30-2.52 (br s, 8H); 3.21 (d, J = 5.24 Hz, 2H); 5.74 (quintet, J = 6.16 Hz, 1H); 5.98 (s, 1H); 6.47 (d, J = 12.08 Hz, 1H); 6.55-6.59 (m, 2H); 6.70-6.82 (br m, 4H); 7.20 (t, J = 7.96 Hz, 1H); 7.22 (d, J = 8.20 Hz, 2H); 7.33 (d, J = 8.12 Hz, 2H); 9.04 (s, 1H); 9.52 (s, 1H) |
| 15 | 3-(3-Hydroxyphenyl)-4-methyl-2-{4-[(E)-3-(4-methylpiperazin-1-yl) propenyl]phenyl}-2H-chromen-6-ol | ($d_6$-DMSO, 400 MHz); 2.09 (s, 3H); 2.23 (s, 3H); 2.28-2.52 (br s, 8H); 3.10 (s, 2H); 5.94 (s, 1H); 6.20-6.33 (m, 1H); 6.49 (d, J = 15.80 Hz, 1H); 6.55 (s, 2H); 6.66-6.83 (m, 4H); 7.19 (t, J = 7.70 Hz, 1H); 7.27 (d, J = 7.75 Hz, 2H); 7.35 (d, J = 7.90 Hz, 2H); 9.03 (s, 1H); 9.51 (s, 1H) |

TABLE 2-continued

| Comp # | Chemical name | NMR |
|---|---|---|
| 16 | 2-{4-[(Z)-3-((R)-3-Amino piperidin-1-yl) propenyl]phenyl}-3-(3-hydroxyphenyl)-4-methyl-2H-chromen-6-ol | (d$_6$-DMSO, 400 MHz); 0.96-1.08 (br m, 1H); 1.40-1.52 (br m, 1H); 1.58-1.68 (br m, 1H); 1.68-1.78 (br m, 2H); 1.86-1.98 (br m, 1H); 2.10 (s, 3H); 2.59-2.68 (br m, 1H); 2.68-2.80 (br m, 2H); 3.15-3.20 (m, 2H); 5.74 (dt, J$_1$ = 12.20 Hz, J$_2$ = 6.24 Hz, 1H); 5.98 (s, 1H); 6.47 (d, J = 12.12 Hz, 1H); 6.53-6.60 (m, 2H); 6.69-6.74 (m, 2H); 6.77 (d, J = 7.72 Hz, 1H); 6.80 (d, J = 2.28 Hz, 1H); 7.16-7.24 (m, 3H); 7.32 (d, J = 7.24 Hz, 2H); four exchangeable protons |
| 17 | 2-(4-{(Z)-3-[4-(2-Hydroxy ethyl)piperazin-1-yl]-propenyl}phenyl)-3-(3-hydroxyphenyl)-4-methyl-2H-chromen-6-ol | (d$_6$-DMSO, 400 MHz); 2.09 (s, 3H); 2.20-2.50 (br m, 10H); 3.16-3.24 (br s, 2H); 3.51-3.60 (br s, 2H); 5.74 (dt, J$_1$ = 11.95 Hz, J$_2$ = 6.25 Hz, 1H); 5.97 (s, 1H); 6.47 (d, J = 11.90 Hz, 1H); 6.52-6.59 (m, 2H); 6.68-6.75 (s merged with d, 2H); 6.77 (d, J = 7.60 Hz, 1H); 6.80 (d, J = 2.40 Hz, 1H); 7.20 (t, J = 7.80 Hz, 1H); 7.22 (d, J = 8.15 Hz, 2H); 7.33 (d, J = 8.15 Hz, 2H); 9.04 (s, 1H); 9.52 (s, 1H); one exchangeable proton |
| 18 | 3-(3-Hydroxyphenyl)-4-methyl-2-(4-{(Z)-3-+4-(4,4,5,5,5-pentafluoropentyl)piperazin-1-yl}propenyl}phenyl)-2H-chromen-6-ol | (d$_6$-DMSO, 400 MHz); 1.68 (quintet, J = 7.00 Hz, 2H); 2.09 (s, 3H); 2.13-2.32 (m, 3H); 2.32-2.50 (m, 8H); 3.19 (d, J = 4.72 Hz, 2H); 5.74 (dt, J$_1$ = 12.16 Hz, J$_2$ = 6.16 Hz, 1H); 5.97 (s, 1H); 6.47 (d, J = 12.08 Hz, 1H); 6.52-6.61 (m, 2H); 6.68-6.75 (m, 2H); 6.77 (d, J = 7.64 Hz, 1H); 6.80 (d, J = 2.32 Hz, 1H); 7.16-7.26 (m, 3H); 7.33 (d, J = 8.24 Hz, 2H); 9.03 (s, 1H); 9.51 (s, 1H); one proton is merged between 2.50-2.60 |
| 19 | 2,2-Dimethylpropionic acid 3-[3-(2,2-dimethyl propionyloxy)-phenyl]-4-methyl-2-{4-[(Z)-3-((R)-3-methyl pyrrolidin-1-yl)propenyl]-phenyl}-2H-chromen-6-yl ester | (d$_6$-DMSO, 400 MHz); 0.96 (d, J = 6.72 Hz, 3H); 1.20-1.34 (br s, 19H); 1.34-1.46 (m, 1H); 1.93-2.04 (m, 1H); 2.07 (s, 3H); 2.18-2.30 (br m, 1H); 2.90-3.10 (br m, 2H); 3.10-3.22 (br m, 1H); 3.74-3.89 (br s, 2H); 5.75 (dt, J$_1$ = 12.20 Hz, J$_2$ = 6.24 Hz, 1H); 6.20 (s, 1H); 6.57 (d, J = 11.92 Hz, 1H); 6.74 (d, J = 8.64 Hz, 1H); 6.83 (dd, J$_1$ = 8.64 Hz, J$_2$ = 2.68 Hz, 1H); 7.01 (dd, J$_1$ = 8.12 Hz, J$_2$ = 1.52 Hz, 1H); 7.06 (d, J = 2.64 Hz, 1H); 7.12-7.16 (br m, 1H); 7.16-7.25 (m, 3H); 7.32 (d, J = 8.20 Hz, 2H); 7.39 (d, J = 7.88 Hz, 1H) |
| 20 | (R)-1-((Z)-3-{4-[6-Methoxy-3-(3-methoxy phenyl)-4-methyl-2H-chromen-2-yl]phenyl} allyl)-3-methyl pyrrolidine hydrochloride. | (d$_6$-DMSO, 400 MHz); 1.06 (dd, J$_1$ = 11.20 Hz, J$_2$ = 6.65 Hz, 3H); 1.45-1.65 (m, 1H); 2.02-2.12 (m, 1H); 2.16 (s, 3H); 2.25-2.50 (m, 1H); 2.94-3.20 (m, 2H); 3.47-3.67 (m, 2H); 3.78 (s, 3H); 3.79 (s, 3H); 4.10 (d, J = 5.95 Hz, 2H); 5.82-5.90 (m, 1H); 6.17 (s, 1H); 6.68-6.78 (m, 3H); 6.90-6.97 (m, 4H); 7.24 (d, J = 8.20 Hz, 2H); 7.34 (t, J = 8.15 Hz, 1H); 7.39 (d, J = 7.45 Hz, 2H) |
| 21 | 3-(3-Hydroxy phenyl)-4-methyl-2-[4-(3-methyl aminoprop-1-ynyl)phenyl]-2H-chromen-6-ol | (d$_6$-DMSO, 400 MHz); 2.08 (s, 3H); 2.35 (s, 3H); 3.51 (s, 2H); 5.98 (s, 1H); 6.54-6.60 (m, 2H); 6.66-6.69 (br s, 1H); 6.71-6.77 (m, 2H); 6.80 (d, J = 2.30 Hz, 1H); 7.19 (t, J = 7.85 Hz, 1H); 7.30-7.36 (m, 4H); 9.04 (s, 1H); 9.51 (s, 1H); one exchangeable proton |
| 22 | 2-[4-(3-Dodecylamino-prop-1-ynyl)-phenyl]-3-(3-hydroxy-phenyl)-4-methyl-2H-chromen-6-ol | (d$_6$-DMSO, 400 MHz); 0.90 (t, J = 6.64 Hz, 3H); 1.21-1.36 (m, 18H); 1.38-1.50 (m, 2H); 2.08 (s, 3H); 2.61 (t, J = 7.08 Hz, 2H); 3.56 (s, 2H); 5.98 (s, 1H); 6.54-6.61 (m, 2H); 6.66-6.69 (br s, 1H); 6.70-6.77 (m, 2H); 6.80 (d, J = 1.60 Hz, 1H); 7.19 (t, J = 7.88 Hz, 1H); 7.29-7.35 (br s, 4H); 9.04 (s, 1H); 9.50 (s, 1H); one exchangeable proton |
| 23 | 2-{4-[3-((E)-3,7-Dimethyl octa-2,6-dienylamino)-prop-1-ynyl]-phenyl}-3-(3-hydroxyphenyl)-4-methyl-2H-chromen-6-ol | (d$_6$-DMSO, 400 MHz); 1.60 (s, 3H); 1.67 (s, 3H); 1.69 (s, 3H); 2.00-2.07 (m, 2H); 2.07-2.14 (m, 5H); 3.33 (d, J = 6.80 Hz, 2H); 3.40 (s, 2H); 5.08-5.14 (br t, 1H); 5.16-5.23 (br t, 1H); 6.00 (s, 1H); 6.54-6.60 (m, 2H); 6.67-6.82 (m, 4H); 7.20 (t, J = 7.84 Hz, 1H); 7.32-7.38 (m, 4H); 9.06 (s, 1H); 9.52 (s, 1H); one exchangeable proton |
| 24 | 3-(3-Hydroxyphenyl)-4-methyl-2-{4-[3-((R)-3-methylpyrrolidin-1-yl) prop-1-ynyl]phenyl}-2H-chromen-6-ol | (d6-DMSO, 400 MHz); 1.02 (d, J = 6.50 Hz, 3H); 1.27-1.37 (br m, 1H); 1.94-2.05 (br m, 1H); 2.09 (s, 3H); 2.16-2.27 (m, 2H); 2.62-2.72 (m, 2H); 2.80-2.91 (br t, 1H); 3.60 (s, 2H); 5.99 (s, 1H); 6.54-6.60 (m, 2H); 6.68 (d, J = 1.75 Hz, 1H); 6.72 (dd, J$_1$ = 8.10 Hz, J$_2$ = 1.65 Hz, 1H); 6.76 (d, J = 7.70 Hz, 1H); 6.80 (d, J = 2.00 Hz, 1H); 7.20 (t, J = 7.85 Hz, 1H); 7.32 (d, J = 8.35 Hz, 2H), 7.35 (d, J = 8.35 Hz, 2H); 9.04 (s, 1H); 9.51 (s, 1H) |
| 25 | 3-(3-Hydroxyphenyl)-4-methyl-2-[4-(3-piperidin-1-yl-prop-1-ynyl)phenyl]-2H-chromen-6-ol | (d$_6$-DMSO, 400 MHz); 1.35-1.43 (m, 2H); 1.50-1.59 (m, 4H); 2.09 (s, 3H); 2.43-2.52 (m, 4H); 3.47 (s, 2H); 5.99 (s, 1H); 6.54-6.60 (m, 2H); 6.66-6.69 (br s, 1H); 6.70-6.78 (m, 2H); 6.80 (d, J = 1.64 Hz, 1H); 7.19 (t, J = 7.84 Hz, 1H); 7.31 (d, J = 8.36 Hz, 2H); 7.35 (d, J = 8.40 Hz, 2H); 9.05 (s, 1H); 9.52 (s, 1H) |
| 26 | 3-(3-Hydroxyphenyl)-4-methyl-2-{4-[3-(4-methyl piperazin-1-yl)prop-1-ynyl]phenyl}-2H-chromen-6-ol | (d$_6$-DMSO, 400 MHz); 2.08 (s, 3H); 2.21 (s, 3H); 2.31-2.50 (br s, 3H); 3.50 (s, 2H); 5.98 (s, 1H); 6.52-6.61 (m, 2H); 6.68 (d, J = 1.60 Hz, 1H); 6.72 (dd, J$_1$ = 8.10 Hz, J$_2$ = 1.95 Hz, 1H); 6.74 (d, J = 7.70 Hz, 1H); 6.80 (d, J = 2.10 Hz, 1H); 7.19 (t, J = 7.90 Hz, 1H); 7.32 (d, J = 8.30 Hz, 2H); 7.35 (d, J = 8.25 Hz, 2H); 9.04 (s, 1H); 9.51 (s, 1H); five protons are merged between 2.50-2.61 |
| 27 | 3-(3-Hydroxyphenyl)-4-methyl-2-{4-[4-(4-methyl piperazin-1-yl)-but-1-ynyl]phenyl}-2H-chromen-6-ol | (d$_6$-DMSO, 400 MHz); 2.08 (s, 3H); 2.26 (s, 3H); 2.37-2.53 (br m, 7H); 2.58-2.61 (br m, 5H); 5.97 (s, 1H); 6.54-6.59 (m, 2H); 6.66-6.68 (br m, 1H); 6.70-6.77 (m, 2H); 6.78-6.82 (br m, 1H); 7.19 (t, J = 7.84 Hz, 1H); 7.30 (s, 4H); 9.06 (s, 1H); 9.52 (s, 1H) |
| 28 | 3-(3-Methoxyphenyl)-4-methyl-2-{4-[(Z)-3-((R)-3-methylpyrrolidin-1-yl)propenyl]phenyl}-2H-chromen-6-ol. | (d$_6$-DMSO, 400 MHz); 1.04 (d, J = 6.72 Hz, 3H); 1.41-1.56 (br m, 1H); 2.01-2.10 (br m, 1H); 2.11 (s, 3H); 2.23-2.39 (br m, 1H); 2.90-3.33 (br m, 4H); 3.79 (s, 3H); 3.82-4.02 (br s, 2H); 5.82 (q, J = 5.36 Hz, 1H); 6.10 (s, 1H); 6.58 (d, J = 2.52 Hz, 1H); 6.59 (s, 1H); 6.62-6.68 (br d, 1H); 6.82 (d, J = 2.28 Hz, 1H); 6.88-6.96 (m, 3H); 7.23 (d, J = 8.24 Hz, 2H); 7.33 (t, J = 7.88 Hz, 1H); 7.37 (d, J = 8.20 Hz, 2H); 9.07 (s, 1H) |

TABLE 2-continued

| Comp # | Chemical name | NMR |
|---|---|---|
| 29 | 3-(4-Hydroxyphenyl)-4-methyl-2-[4-((Z)-3-pyrrolidin-1-ylpropenyl)phenyl]-2H-chromen-6-ol | (d$_6$-DMSO, 400 MHz); 1.71-1.84 (br s, 4H); 2.10 (s, 3H); 2.63-2.81 (br s, 4H); 3.50-3.65 (br s, 2H); 5.82 (dt, J$_1$ = 10.12 Hz, J$_2$ = 6.28 Hz, 1H); 5.99 (s, 1H); 6.48-6.62 (d merged in in, 3H); 6.68-6.86 (m, 4H); 7.17-7.28 (d merged in t, 3H); 7.34 (d, J = 8.16 Hz, 2H); 9.05 (s, 1H); 9.53 (s, 1H) |
| 30 | 3-(4-Hydroxyphenyl)-4-methyl-2-[4-((E)-3-pyrrolidin-1-ylpropenyl)phenyl]-2H-chromen-6-ol | (d$_6$-DMSO, 400 MHz); 1.71-1.84 (br s, 4H); 2.09 (s, 3H); 2.60-2.74 (br s, 4H); 3.28-3.50 (br d, 2H); 5.95 (s, 1H); 6.33 (dt, J$_1$ = 13.28 Hz, J$_2$ = 6.59 Hz, 1H); 6.52-6.61 (m, 3H); 6.67-6.74 (m, 2H); 6.76 (d, J = 7.72 Hz, 1H); 6.81 (s, 1H); 7.19 (t, J = 7.83 Hz, 1H); 7.29 (d, J = 8.23 Hz, 2H); 7.36 (d, J = 8.23 Hz, 2H); 9.05 (s, 1H); 9.53 (s, 1H) |
| 31 | 2-{4-[(Z)-3-(3-Butylamino pyrrolidin-1-yl)propenyl]phenyl}-3-(3-hydroxyphenyl)-4-methyl-2H-chromen-6-ol | (d$_5$-Pyridine, 400 MHz); 0.79 (t, J = 7.32 Hz, 3H); 1.22-1.31 (m, 2H); 1.36-1.44 (m, 2H); 1.47-1.61 (br m, 1H); 1.90-2.01 (m, 1H); 2.13 (s, 3H); 2.33-2.42 (m, 2H); 2.42-2.58 (m, 3H); 2.63-2.70 (m, 1H); 3.18-3.34 (m, 3H); 5.84 (dt, J$_1$ = 12.39 Hz, J$_2$ = 5.99 Hz, 1H); 6.29 (s, 1H); 6.38 (d, J = 12.01 Hz, 1H); 6.86-6.96 (m, 3H); 7.04 (dd, J$_1$ = 7.88 Hz, J$_2$ = 1.93 Hz, 1H); 7.18-7.30 (m, 5H); 7.60 (d, J = 8.14 Hz, 2H); 10.99-11.45 (br s, 1H); 11.45-11.90 (br s, 1H) one exchangeable proton |
| 32 | 2-{4-[(E)-3-(3-Butylamino pyrrolidin-1-yl)-propenyl]phenyl}-3-(3-hydroxyphenyl)-4-methyl-2H-chromen-6-ol | (d$_5$-Pyridine, 400 MHz); 0.74-0.81 (m, 3H); 1.21-1.32 (m, 2H); 1.36-1.46 (m, 2H); 1.53-1.64 (br m, 1H); 1.96-2.08 (m, 1H); 2.13 (s, 3H); 2.37-2.62 (br m, 5H); 2.70-2.77 (m, 1-1); 3.08-3.16 (m, 2H); 3.21-3.32 (br m, 1H); 4.80-5.10 (br s, 1H); 6.23 (s, 1H); 6.25-6.48 (m, 1H); 6.48 (d, J = 15.93 Hz, 1H); 6.88-6.97 (m, 2H); 7.02-7.39 (m, 7H); 7.52-7.56 (m, 2H); 10.97-11.18 (br s, 1H); 11.55-11.80 (br s, 1H) |
| 33 | 3-(3-Hydroxyphenyl)-4-methyl-2-[4-((E)-3-thiomorpholin-4-ylpropenyl)phenyl]-2H-chromen-6-ol | (d$_6$-DMSO, 400 MHz); 2.09 (s, 3H); 2.60-2.71 (m, 8H); 3.11 (d, J = 6.40 Hz, 2H); 5.94 (s, 1H); 6.26 (dt, J$_1$ = 16.56 Hz, J$_2$ = 6.48 Hz, 1H); 6.48 (d, J = 15.96 Hz, 1H); 6.55 (s, 2H); (d, J = 8.24 Hz, 2H); 9.04 (s, 1H); 9.52 (s, 1H); 7.27 (d, J = 8.24 Hz, 2H); 7.36 (d, J = 8.24 Hz, 2H); 9.04 (s, 1H); 9.52 (s, 1H) |
| 34 | 3-(3-Hydroxyphenyl)-4-methyl-2-{4-[(Z)-3-(4-methylpiperidin-1-yl)propenyl]phenyl}-2H-chromen-6-ol | (d$_6$-DMSO + Acetic acid, 400 MHz); 0.92 (d, J = 6.55 Hz, 3H); 1.20-1.31 (br m, 2H); 1.37-1.50 (br s, 1H); 1.63-1.72 (br d, 2H); 2.10 (s, 3H); 2.25-2.36 (br t, 2H); 3.05 (d, J = 11.35 Hz, 2H); 3.52 (d, J = 5.55 Hz, 2H); 5.80 (dt, J$_1$ = 11.90 Hz, J$_2$ = 6.40 Hz, 1H); 5.99 (s, 1H); 6.54-6.62 (m, 3H); 6.68-6.75 (m, 2H); 6.77-6.83 (m, 2H); 7.16-7.25 (m, 3H); 7.34 (d, J = 8.10 Hz, 2H); two exchangeable protons |
| 35 | 3-(3-Hydroxyphenyl)-4-methyl-2-[4-((E)-3-nonylamino propenyl)phenyl]-2H-chromen-6-ol | (d$_6$-DMSO, 400 MHz); 0.90 (t, J = 6.96 Hz, 3H); 1.25-1.37 (br s, 12H); 1.48-1.57 (br m, 2H); 2.09 (s, 3H); 2.72 ( t, J = 7.56 Hz, 2H); 3.52 (d, J = 6.44 Hz, 2H); 5.96 (s, 1H); 6.28 (dt, J$_1$ = 15.88 Hz, J$_2$ = 6.56 Hz, 1H); 6.56 (s, 2H); 6.62 (d, J = 15.84 Hz, 1H); 6.68-6.85 (m, 4H); 7.20 (t, J = 7.84 Hz, 1H); 7.31 (d, J = 8.28 Hz, 2H); 7.36 (d, J = 8.32 Hz, 2H); 9.05 (s, 1H); 9.53 (s, 1H); one exchangeable proton |
| 36 | 3-(3-Hydroxyphenyl)-4-methyl-2-{4-[(E)-3-(4-methylpiperidin-1-yl)-propenyl]phenyl}-2H-chromen-6-ol | (d$_6$-DMSO, 400 MHz); 0.94 (d, J = 6.50 Hz, 3H); 1.31-1.40 (br m, 2H); 1.52-1.64 (br s, 1H); 1.73-1.82 (br d, 2H); 2.09 (s, 3H); 2.73 (t, J = 11.90 Hz, 2H); 3.28 (d, J = 12.25 Hz, 2H); 3.68 (d, J = 7.10 Hz, 2H); 6.32 (dt, J$_1$ = 12.25 Hz, J$_2$ = 7.25 Hz, 1H); 6.54-6.58 (m, 2H); 6.68-6.74 (m, 3H); 6.77 (d, J = 7.70 Hz, 1H); 6.79-6.82 (br t, 1H); 7.19 (t, J = 7.80 Hz, 1H); 7.33 (d, J = 8.25 Hz, 2H); 7.41 (d, J = 8.30 Hz, 2H); two exchangeable protons |
| 37 | 3-(3-Hydroxyphenyl)-4-methyl-2-[4-((Z)-3-nonylamino propenyl)phenyl]-2H-chromen-6-ol | (d$_6$-DMSO, 400 MHz); 0.91 (t, J = 6.60 Hz, 3H); 1.23-1.36 (br s, 12H); 1.50-1.62 (br m, 2H); 2.10 (s, 3H); 2.88 (t, J = 7.48 Hz, 2H); 3.83 (d, J = 5.04 Hz, 2H); 5.76 (d, J$_1$ = 12.36 Hz, J$_2$ = 6.36 Hz, 1H); 6.01 (s, 1H); 6.55-6.59 (m, 2H); 6.68 (d, J = 12.40 Hz, 1H); 6.71-6.83 (m, 4H); 7.20 (t, J = 7.72 Hz, 1H); 7.24 (d, J = 8.24 Hz, 2H); 7.37 (d, J = 8.28 Hz, 2H); 9.07 (s, 1H); 9.56 (s, 1H); one exchangeable proton |
| 38 | 2-{4-[(Z)-3-(9-Fluorononyl amino)propenyl]phenyl}-3-(3-hydroxyphenyl)-4-methyl-2H-chromen-6-ol | (d$_6$-DMSO, 400 MHz); 1.26-1.42 (m, 10H); 1.50-1.59 (m, 2H); 1.62-1.73 (m, 2H); 2.10 (s, 3H); 2.82 (t, J = 7.55 Hz, 2H); 3.73-3.80 (m, 2H); 4.48 (dt, J$_1$ = 47.56 Hz, J$_2$ = 6.10 Hz, 2H); 5.76 (dt, J$_1$ = 11.90 Hz, J$_2$ = 6.25 Hz, 1H); 6.00 (s, 1H); 6.53-6.67 (m, 3H); 6.70-6.82 (m, 4H); 7.20 (t, J = 7.90 Hz, 1H); 7.24 (d, J = 8.30 Hz, 2H); 7.36 (d, J = 8.20 Hz, 2H); 9.05 (s, 1H); 9.53 (s, 1H); one exchangeable proton |
| 39 | 2-{4-[(E)-3-(9-Fluoro nonylamino)propenyl]phenyl}-3-(3-hydroxy phenyl)-4-methyl-2H-chromen-6-ol | (d$_6$-DMSO, 400 MHz); 1.26-1.40 (m, 10H); 1.54-1.61 (m, 2H); 1.61-1.72 (m, 2H); 2.09 (s, 3H); 2.83 (t, J = 7.75 Hz, 2H); 3.64 (d, J = 6.75 Hz, 2H); 4.47 (dt, J$_1$ = 47.56 Hz, J$_2$ = 6.10 Hz, 2H); 5.97 (s, 1H); 6.27 (dt, J$_1$ = 15.90 Hz, J$_2$ = 6.70 Hz, 1H); 6.53-6.59 (br s, 2H); 6.67-6.83 (m, 5H); 7.19 (t, J = 7.85 Hz, 1H); 7.33 (d, J = 8.30 Hz, 2H); 7.38 (d, J = 8.45 Hz, 2H); 9.07 (s, 1H); 9.54 (s, 1H); one exchangeable proton |
| 40 | 3-(3-Hydroxy phenyl)-4-methyl-2-[4-((Z)-3-pyrrolidin-1-ylbut-1-enyl)phenyl]-2H-chromen-6-ol. | (d$_6$-DMSO + Acetic acid, 400 MHz); 1.33-1.41 (m, 3H); 1.74-1.86 (br m, 4H); 2.10 (s, 3H); 2.80-2.98 (m, 4H); 3.88-3.98 (m, 1H); 5.74 (m, 1H); 6.01 (s, 1H); 6.53-6.62 (m, 3H); 6.70-6.75 (m, 2H); 6.77-6.83 (m, 2H); 7.16-7.26 (in, 3H); 7.33-7.41 (m, 2H). two exchangeable protons |
| 41 | 2-{4-[(E)-3-(10-Fluoro decylamino)propenyl]phenyl}-3-(3-hydroxy phenyl)-4-methyl-2H-chromen-6-ol | (d$_6$-DMSO + Acetic acid, 400 MHz); 1.30 (s, 12H); 1.53-1.60 (br m, 2H); 1.61-1.72 (br m, 2H); 2.09 (s, 3H); 2.80 (t, J = 7.65 Hz, 2H); 3.61 (d, J = 6.70 Hz, 2H); 4.46 (t, J = 47.56 Hz, J$_2$ = 6.10 Hz, 2H); 5.97 (s, 1H); 6.27 (dt, J = 15.90 Hz, J$_2$ = 6.90 Hz, 1H); 6.56 (s, 2H); 6.65-6.79 (m, 4H); 6.81 (s, 1H); 7.19 (t, J = 7.85 Hz, 2H); 7.32 (d, J = 8.35 Hz, 2H); 7.37 (d, J = 8.35 Hz, 2H); two exchangeable protons |

TABLE 2-continued

| Comp # | Chemical name | NMR |
|---|---|---|
| 42 | 2-{4-[3-(9-Fluoro nonylamino)prop-1-ynyl]phenyl}-3-(3hydroxy phenyl)-4-methyl-2H-chromen-6-ol | (d$_6$-DMSO + Acetic acid); 1.24-1.41 (br m, 10H); 1.52-1.72 (m, 4H); 2.08 (s, 3H); 2.93 (t, J = 7.75 Hz, 2H); 4.04 (s, 2H); 4.45 (dt, J$_1$ = 47.56 Hz, J$_2$ = 6.15 Hz, 2H); 6.01 (s, 1H); 6.54-6.61 (m, 2H); 6.66-6.83 (m, 4H); 7.19 (t, J = 7.85 Hz, 1H); 7.36 (d, J = 8.35 Hz, 2H); 7.40 (d, J = 8.40 Hz, 2H); three exchangeable protons |
| 43 | 2-{4-[(Z)-3-(10-Fluoro decylamino)propenyl]phenyl}-3-(3-hydroxy phenyl)-4-methyl-2H-chromen-6-ol | (d$_6$-DMSO + Acetic acid, 400 MHz); 1.30 (s, 12H); 1.53-1.60 (br m, 2H); 1.61-1.72 (br m, 2H); 2.09 (s, 3H); 2.80 (t, J = 7.65 Hz, 2H); 3.61 (d, J = 6.70 Hz, 2H); 4.46 (t, J = 47.56 Hz, J$_2$ = 6.10 Hz, 2H); 5.97 (s, 1H); 6.27 (dt, J$_1$ = 15.90 Hz, J$_2$ = 6.90 Hz, 1H); 6.56 (s, 2H); 6.65-6.79 (m, 4H); 6.81 (s, 1H); 7.19 (t, J = 7.85 Hz, 1H); 7.32 (d, J = 8.35 Hz, 2H); 7.37 (d, J = 8.35 Hz, 2H); two exchangeable protons |
| 44 | 2-{4-[(E)-3-(9,9-Difluoro nonylamino)propenyl]phenyl}-3-(3-hydroxy phenyl)-4-methyl-2H-chromen-6-ol | (d$_6$-DMSO + Acetic acid, 400 MHz); 1.24-1.47 (br m, 10H); 1.51-1.63 (m, 2H); 1.73-1.92 (m, 2H); 2.09 (s, 3H); 2.80 (t, J = 7.60 Hz, 2H); 3.61 (d, J = 6.56 Hz, 2H); 5.97 (s, 1H); 6.09 (tt, J$_1$ = 56.90 Hz, J$_2$ = 4.44 Hz, 1H); 6.27 (dt, J$_1$ = 15.89 Hz, J$_2$ = 6.76 Hz, 1H); 6.54-6.60 (m, 2H); 6.64-6.84 (m, 5H); 7.19 (t, J = 7.80 Hz, 1H); 7.32 (d, J = 8.36 Hz, 2H); 7.37 (d, J = 8.36 Hz, 2H); three exchangeable protons |
| 45 | 2-(4-{(E)-3-[(9-Fluoro nonyl)methylamino]-propenyl}phenyl)-3-(3-hydroxypheny)-4-methyl-2H-chromen-6-ol | (d$_6$-DMSO + Acetic acid, 400 MHz); 1.26-1.41 (br m, 10H); 1.45-1.56 (br m, 2H); 1.58-1.73 (m, 2H); 2.10 (s, 3H); 2.31 (s, 3H); 2.46-2.53 (m, 2H); 3.29 (d, J = 6.40 Hz, 2H); 4.46 (dt, J$_1$ = 47.54 Hz, J$_2$ = 6.12 Hz, 2H); 5.96 (s, 1H); 6.29 (dt, J$_1$ = 15.85 Hz, J$_2$ = 6.80 Hz, 1H); 6.53-6.59 (m, 3H); 6.68-6.83 (m, 4H); 7.20 (t, J = 7.84 Hz, 1H); 7.29 (d, J = 8.28 Hz, 2H); 7.37 (d, J = 8.32 Hz, 2H); two exchangeable protons |
| 46 | 2-{4-[(Z)-3-(9,9-Difluoro nonylamino)propenyl]phenyl}-3-(3-hydroxy phenyl)-4-methyl-2H-chromen-6-ol | (d$_6$-DMSO + Acetic acid, 400 MHz); 1.18-1.42 (br m, 10H); 1.44-1.55 (m, 2H); 1.69-1.87 (m, 2H); 2.05 (s, 3H); 2.81 (t, J = 7.84 Hz, 2H); 3.76 (d, J = 4.76 Hz, 2H); 5.70 (dt, J$_1$ = 11.84 Hz, J$_2$ = 6.40 Hz, 1H); 5.95 (s, 1H); 6.04 (tt, J$_1$ = 56.94 Hz, J$_2$ = 4.48 Hz, 1H); 6.48-6.55 (m, 2H); 6.58-6.78 (m, 5H); 7.12-7.21 (m, 3H); 7.3 (d, J = 8.24 Hz, 2H); three exchangeable protons |
| 47 | 2-{4-[(E)-3-(9-Fluoro nonylamino)propenyl]phenyl}-3-(3-methoxyphenyl)-4-methyl-2H-chromen-6-ol | (d$_6$-DMSO + Acetic acid, 400 MHz); 1.24-1.42 (br m, 10H); 1.53-1.75 (m, 4H); 2.05 (s, 3H); 2.83 (t, J = 7.88 Hz, 2H); 3.65 (d, J = 7.36 Hz, 2H); 3.73 (s, 3H); 4.41 (dt, J$_1$ = 47.54 Hz, J$_2$ = 6.12 Hz, 2H); 6.01 (s, 1H); 6.20 (d, J$_1$ = 15.93 Hz, J$_2$ = 6.96 Hz, 1H); 6.55-6.59 (m, 2H); 6.68 (d, J = 15.93 Hz, 1H); 6.80-6.85 (m, 1H); 6.87-6.94 (m, 3H); 7.28-7.42 (m, 5H); two exchangeable protons |
| 48 | 2-(4-{(Z)-3-[(9-Fluorononyl)methyl amino]propenyl}phenyl)-3-(3-hydroxyphenyl)-4-methyl-2H-chromen-6-ol | (d$_6$-DMSO + Acetic acid, 400 MHz); 1.25-1.40 (br m, 10H); 1.40-1.48 (br m, 2H); 1.61-1.73 (m, 2H); 2.09 (s, 3H); 2.23 (s, 3H); 2.38-2.45 (m, 2H); 3.33 (d, J = 4.98 Hz, 2H); 4.47 (dt, J$_1$ = 47.56 Hz, J$_2$ = 6.12 Hz, 2H); 5.75 (dt, J$_1$ = 11.95 Hz, J$_2$ = 6.15 Hz, 1H); 5.98 (s, 1H); 6.51 (d, J = 11.98 Hz, 1H); 6.54-6.59 (m, 2H); 6.70-6.82 (m, 4H); 7.20 (t, J = 7.78 Hz, 1H); 7.22 (d, J = 8032 Hz, 2H); 7.33 (d, J = 8.22 Hz, 2H); two exchangeable protons |
| 49 | 2-{4-[(E)-3-(8-Fluoro octylamino)-propenyl]phenyl}-3-(3-hydroxyphenyl)-4-methyl-2H-chromen-6-ol | (d$_6$-DMSO + Acetic acid, 400 MHz); 1.26-1.43 (m, 8H); 1.54-1.75 (m, 4H); 2.09 (s, 3H); 2.88 (t, J = 7.60 Hz, 2H); 3.70 (d, J = 6.76 Hz, 2H); 4.46 (dt, J = 47.54 Hz, J$_2$ = 6.08 Hz, 2H); 5.98 (s, 1H); 6.26 (dt, J$_1$ = 15.93 Hz, J$_2$ = 6.88 Hz, 1H); 6.54-6.59 (br s, 2H); 6.68-6.84 (m, 5H); 7.19 (t, J = 7.80 Hz, 1H); 7.33 (d, J = 8.32 Hz, 2H); 7.38 (d, J = 8.48 Hz 2H); three exchangeable protons |
| 50 | 2-{4-[(Z)-3-(8-Fluoro octylamino)propenyl]phenyl}-3-(3-hydroxyphenyl)-4-methyl-2H-chromen-6-ol | (d$_6$-DMSO + Acetic acid, 400 MHz); 1.23-1.42 (m, 8H); 1.48-1.58 (m, 2H); 1.60-1.73 (m, 2H); 2.10 (s, 3H); 2.84 (t, J = 7.60 Hz, 2H); 3.80 (dd J$_1$ = 6.50 Hz, J$_2$ = 1.75 Hz, 2H); 4.47 (dt, J$_1$ = 47.51 Hz, J$_2$ = 6.15 Hz, 2H); 5.74 (dt, J$_1$ = 11.85 Hz, J$_2$ = 6.35 Hz, 1H); 6.00 (s, 1H); 6.54-6.61 (m, 2H); 6.65 (d, J = 12.00 Hz, 1H); 6.69-6.75 (m, 2H); 6.78 (d, J = 7.65 Hz, 1H); 6.81 (d, J = 2.40 Hz, 1H); 7.20 (t, J = 7.85 Hz, 1H); 7.23 D, J = 8.25 Hz, 2H); 7.36 (d, J = 8.20 Hz, 2H); three exchangeable protons |
| 51 | 2-{4-[3-(8-Fluoro octylamino)prop-1-ynyl]phenyl}-3-(3 Hydroxy phenyl)-4-methyl-2H-chromen-6-ol | (d$_6$-DMSO + Acetic acid, 400 MHz); 1.28-1.40 (br m, 8H); 1.40-1.50 (br m, 2H); 1.58-1.75 (m, 2H); 2.02 (s, 3H); 2.60-2.69 (br m, 2H); 3.54-3.63 (br m, 2H); 4.40 (dt, J$_1$ = 47.58 Hz, J$_2$ = 6.12 Hz, 2H); 5.93 (s, 1H); 6.55-6.59 (m, 2H); 6.66-6.82 (m, 4H); 7.14 (t, J = 7.88 Hz, 1H); 7.31-7.37 (m, 4H); three exchangeable proton |
| 52 | 2-{4-[3-(10-Fluoro decylamino)prop-1-ynyl]phenyl}-3-(3-hydroxyphenyl)-4-methyl-2H-chromen-6-ol | (d$_6$-DMSO + Acetic acid, 400 MHz); 1.27-1.42 (br m, 12H); 1.46-1.55 (m, 2H); 1.61-1.73 (m, 2H); 2.08 (s, 3H); 2.75 (t, J = 7.25 Hz, 2H); 3.78 (s, 2H); 4.46 (dt, J$_1$ = 47.36 Hz, J$_2$ = 6.25 Hz, 2H); 6.00 (s, 1H); 6.54-6.60 (m, 2H); 6.67-6.82 (m, 4H); 7.19 (t, J = 7.95 Hz, 1H); 7.33 (d, J = 8.35 Hz, 2H); 7.36 (d, J = 8.50 Hz, 2H); three exchangeable protons |
| 53 | 2-(4-{3-[(9-Fluorononyl)methyl amino]prop-1-ynyl}phenyl)-3-(3-hydroxyphenyl)-4-methyl-2H-chromen-6-ol | (d$_6$-DMSO+30Acetic acid, 400 MHz); 1.31 (s, 10H); 1.40-1.49 (br m, 2H); 1.60-1.71 (br m, 2H); 2.08 (s, 3H); ); 2.28 (s, 3H); 2.43 (t, J = 7.50 Hz, 2H); 3.56 (s, 3H); 4.45 (dt, J$_1$ = 47.71 Hz, J$_2$ = 6.10 Hz, 2H); 5.98 (s, 1H); 6.56 (s, 2H); 6.68 ( t, J = 1.80 Hz, 1H); 6.72-6.78 (m, 2H); 6.80 (d, J = 1.60 Hz, 2H); 7.20 (t, J = 7.75 Hz, 1H); 7.34 (q, J = 8.32 Hz, 2H); two exchangeable protons |
| 54 | 2-{4-[3-(9,9-Difluoro nonylamino)prop-1-ynyl]phenyl}-3-(3-hydroxyphenyl)-4-methyl-2H-chromen-6-ol. | (d$_6$-DMSO + Acetic acid, 400 MHz); 1.25-1.44 (m, 10H); 1.46-1.56 (m, 2H); 1.76-1.90 (m, 2H); 2.08 (s, 3H); 2.74 (t, J = 7.55 Hz, 2H); 3.76 (s, 2H); 6.00 (s, 1H); 6.08 (tt, J$_1$ = 56.86 Hz, J$_2$ = 4.55 Hz, 1H); 6.54-6.60 (m, 2H); 6.66-6.78 (m, 3H); 6.81 (d, J = 2.30 Hz, 1H); 7.20 (t, J = 7.90 Hz, 1H); 7.33 (d, J = 8.55 Hz, 2H); 7.36 (d, J = 8.50 Hz, 2H); three exchangeable protons |

TABLE 2-continued

| Comp # | Chemical name | NMR |
|---|---|---|
| 55 | 2-{4-[(Z)-3-((R)-3-Fluoromethyl pyrrolidin-1-yl)-propenyl]phenyl}-3-(3-hydroxyphenyl)-4-methyl-2H-chromen-6-ol | (d$_6$-DMSO + Acetic acid, 400 MHz); 1.41-1.52 (m, 1H); 1.85-1.96 (m, 1H); 2.10 (s, 3H); 2.60-2.79 (m, 4H); 3.43-3.50 (m, 2H); 4.24-4.34 (m, 1H); 4.36-4.46 (m, 1H); 5.79 (dt, J$_1$ = 11.88 Hz, J$_2$ = 6.32 Hz, 1H); 5.98 (s, 1H); 6.48 (d, J = 12.00 Hz, 1H); 6.53-6.60 (m, 2H); 6.70-6.83 (m, 4H); 7.17-7.25 (m, 3H); 7.34 (d, J = 8.20 Hz, 2H); one proton is merged between 2.45-2.55; two exchangeable protons |
| 56 | 2-{4-[3-(3,3-Difluoro pyrrolidin-1-yl)prop-1-ynyl]phenyl}-3-(3-hydroxyphenyl)-4-methyl-2H-chromen-6-ol | (d$_6$-DMSO + Acetic acid, 400 MHz); 2.09 (s, 3H); 2.23-2.37 (m, 2H); 2.84 (t, J = 7.00 Hz, 2H); 3.02 (t, J = 13.36 Hz, 2H); 3.69 (s, 2H); 5.99 (s, 1H); 6.53-6.60 (br s, 2H); 6.67-6.82 (m, 4H); 7.20 (t, J = 7.80 Hz, 1H); 7.33 (d, J = 8.32 Hz, 2H); 7.38 (d, J = 8.36 Hz, 2H); two exchangeable protons |
| 57 | 2-{4-[(Z)-3-(3,3-Difluoro pyrrolidin-1-yl)propenyl]phenyl}-3-(3-hydroxyphenyl)-4-methyl-2H-chromen-6-ol | (d$_6$-DMSO + Acetic acid, 400 MHz); 2.09 (s, 3H); 2.19-2.32 (m, 2H); 2.73 (t, J = 6.92 Hz, 2H); 2.91 (t, J = 13.32 Hz, 2H); 3.37 (d, J = 4.72 Hz, 2H); 5.76 (dt, J$_1$ = 11.96 Hz, J$_2$ = 6.40 Hz, 1H); 5.98 (s, 1H); 6.47 (d, J = 12.00 Hz, 1H); 6.55-6.59 (m, 2H); 6.69-6.83 (m, 4H); 7.18 (d, J = 7.96 Hz, 1H); 7.21 (d, J = 8.24 Hz, 2H); 7.33 (d, J = 8.20 Hz, 2H); two exchangeable protons |
| 58 | 2-{4-[(E)-3-(3,3-Difluoro pyrrolidin-1-yl)propenyl]phenyl}-3-(3-hydroxyphenyl)-4-methyl-2H-chromen-6-ol | (d$_6$-DMSO + Acetic acid, 400 MHz); 2.09 (s, 3H); 2.20-2.34 (m, 2H); 2.74 (t, J = 7.00 Hz, 2H); 2.92 (t, J = 13.28 Hz, 2H); 3.24 (d, J = 7.00 Hz, 2H); 5.94 (s, 1H); 6.30 (dt, J$_1$ = 15.93 Hz, J$_2$ = 6.48 Hz, 1H); 6.54 (s, 1H); 6.55 (s, 2H); 6.67-6.82 (m, 4H); 7.19 (t, J = 7.88 Hz, 1H); 7.28 (d, J = 8.24 Hz, 2H); 7.36 (d, J = 8.28 Hz, 2H); two exchangeable protons |
| 59 | 2-{4-[(E)-3-((R)-3-Fluoromethyl pyrrolidin-1-yl)propenyl]phenyl}-3-(3-hydroxyphenyl)-4-methyl-2H-chromen-6-ol | (d$_6$-DMSO + Acetic acid, 400 MHz); 1.48-1.57 (m, 1H); 1.94-2.00 (m, 1H); 2.09 (s, 3H); 2.48-2.52 (m, 3H); 2.71-2.88 (m, 2H); 3.40 (d, J+326.50 Hz, 2H); 4.30-4.45 (m, 2H); 5.95 (s, 1H); 6.32 (dt, J$_1$ = 15.80 Hz, J$_2$ = 6.80 Hz, 1H); 6.53-6.61 (m, 3H); 6.68-6.83 (m, 4H); 7.20 (t, J = 7.85 Hz, 1H); 7.29 (d, J = 8.20 Hz, 2H); 7.37 (d, J = 8.20 Hz, 2H); two exchangeable proton |
| 60 | 2-{4-[(E)-3-((R)-3-Hydroxymethyl pyrrolidin-1-yl)propenyl]phenyl}-3-(3-hydroxyphenyl)-4-methyl-2H-chromen-6-ol | (d$_6$-DMSO + Acetic acid, 400 MHz); 1.55-1.67 (m, 1H); 1.94-2.02 (m, 1H); 2.09 (s, 3H); 2.32-2.46 (m, 1H); 2.71-2.82 (m, 1H); 2.95-3.04 (m, 2H); 3.04-3.13 (m, 2H); 3.32-3.45 (m, 2H); 3.63 (d, J = 6.80 Hz, 2H); 5.97 (s, 1H); 6.31 (dt, J$_1$ = 15.89 Hz, J$_2$ = 6.84 Hz, 1H); 6.53-6.59 (br s, 2H); 6.65-6.83 (m, 5H); 7.20 (t, J = 7.80 Hz, 1H); 7.32 (d, J = 8.20 Hz, 2H); 7.39 (d, J = 8.24 Hz, 2H); three exchangeable protons |
| 61 | 2-(4-{3-[4-(4-Fluorobutoxy)butylamino]prop-1-ynyl}phenyl)-3-(3-hydroxyphenyl)-4-methyl-2H-chromen-6-ol | (d$_6$-DMSO + Acetic acid, 400 MHz); 1.53-1.62 (br m, 2H); 1.62-1.76 (m, 2H); 2.08 (s, 3H); 2.80-2.88 (br s, 2H); 3.37-3.45 (m, 4H); 3.84-3.92 (br s, 2H); 4.46 (dt, J$_1$ = 47.48 Hz, J$_2$ = 6.10 Hz, 2H); 6.01 (s, 1H); 6.54-6.61 (m, 2H); 6.67-6.71 (m, 1H); 6.71-6.78 (m, 2H); 6.80 (d, J = 1.97 Hz, 1H); 7.20 (t, J = 7.86 Hz, 1H); 7.35 (d, J = 8.41 Hz, 2H); 7.38 (d, J = 8.31 Hz, 2H); three exchangeable protons |
| 62 | 2-{4-{(Z)-3-[4-(4-Fluorobutoxy)butylamino]propenyl}phenyl)-3-(3-hydroxyphenyl)-4-methyl-2H-chromen-6-ol | (d$_6$-DMSO + Acetic acid, 400 MHz); 1.50-1.80 (br m, 8H); 2.10 (s, 3H); 2.93 (t, J = 7.20 Hz, 2H); 3.34-3.45 (m, 4H); 3.84-3.90 (br m, 2H); 4.49 (dt, J$_1$ = 47.46 Hz, J$_2$ = 6.04 Hz, 2H); 5.74 (dt, J$_1$ = 11.84 Hz, J$_2$ = 6.32 Hz, 1H); 6.02 (s, 1H); 6.53-6.61 (m, 2H); 6.66-6.77 (m, 3H); 6.78-6.84 (m, 2H); 7.20 (t, J = 8.44 Hz, 1H); 7.24 (d, J = 8.24 Hz, 2H); 7.37 (d, J = 8.24 Hz, 2H); three exchangeable protons |
| 63 | 2-{4-{(E)-3-[4-(4-Fluorobutoxy)butylamino]propenyl}phenyl)-3-(3-hydroxyphenyl)-4-methyl-2H-chromen-6-ol | (d$_6$-DMSO + Acetic acid, 400 MHz); 1.52-1.78 (m, 8H); 2.09 (s, 3H); 2.94 (t, J = 7.55 Hz, 2H); 3.33-3.47 (m, 4H); 3.73 (d, J = 6.75 Hz, 2H); 4.47 (dt, J$_1$ = 47.46 Hz, J$_2$ = 6.10 Hz, 2H); 5.98 (s, 1H); 6.25 (dt, J$_1$ = 15.90 Hz, J$_2$ = 7.00 Hz, 1H); 6.53-6.59 (m, 2H); 6.68-6.84 (m, 5H); 7.19 (t, J = 7.85 Hz, 1H); 7.34 (d, J = 8.30 Hz, 2H); 7.39 (d, J = 8.30 Hz, 2H); three exchangeable protons |
| 64 | 2-{4-[3-((R)-3-Fluoromethyl pyrrolidin-1-yl)-prop-1-ynyl]phenyl}-3-(3-hydroxyphenyl)-4-methyl-2H-chromen-6-ol | (CDCl$_3$ + CD$_3$OD, 400 MHz); 1.41-1.52 (m, 1H); 1.86-1.94 (m, 1H); 2.09 (s, 3H); 2.60-2.80 (m, 5H); 3.65 (s, 2H); 4.26-4.32 (m, 1H); 4.39-4.45 (m, 1H); 5.99 (s, 1H); 6.54-6.61 (m, 2H); 6.67-6.82 (m, 4H); 7.20 (t, J = 7.84 Hz, 2H); 7.32 (d, J = 8.48 Hz, 2H); 7.36 (d, J = 8.44 Hz, 2H); two exchangeable proton |
| 65 | 3-(3-Hydroxyphenyl)-4-methyl-2-{4-[(E)-3-(3-trifluoromethyl pyrrolidin-1-yl)propenyl]phenyl}-2H-chromen-6-ol | (CDCl$_3$ + CD$_3$OD, 400 MHz); 1.83-1.93 (m, 1H); 1.95-2.01 (m, 1H); 2.03 (s, 3H); 2.40-2.50 (m, 2H); 2.80-2.92 (m, 2H); 3.12-3.24 (m, 2H); 3.35 (s, 1H); 5.79 (s, 1H); 6.15 (dt, J$_1$ = 15.80 Hz, J$_2$ = 6.75 Hz, 1H); 6.41 (d, J = 15.85 Hz, 1H); 6.50-6.58 (m, 2H); 6.61 (s, 1H); 6.66 (t, J = 8.10 Hz, 2H); 6.76 (s, 1H); 7.10 (t, J = 7.85 Hz, 1H); 7.16 (d, J = 8.00 Hz, 2H); 7.20 (d, J = 8.00 Hz, 2H); two exchangeable protons |
| 66 | 3-(3-Hydroxyphenyl)-4-methyl-2-{4-[(Z)-3-(3-trifluoromethyl pyrrolidin-1-yl)propenyl]phenyl}-2H-chromen-6-ol | (CDCl$_3$ + CD$_3$OD, 400 MHz); 1.82-1.90 (m, 1H); 1.95-2.03 (m, 1H); 2.04 (s, 3H); 2.38-2.48 (m, 2H); 2.67-2.75 (m, 1H); 2.78-2.90 (m, 2H); 3.28-3.40 (m, 2H); 5.68 (dt, J$_1$ = 11.85 Hz, J$_2$ = 6.34 Hz, 1H); 5.82 (s, 1H); 6.41 (d, J = 11.84 Hz, 1H); 6.52-6.62 (m, 3H); 6.65-6.69 (m, 2H); 6.77 (d, J = 2.72 Hz, 1H); 7.02 (d, J = 8.09 Hz, 2H); 7.11 (t, J = 7.98 Hz, 1H); 7.23 (d, J = 8.12 Hz, 2H); two exchangeable protons |
| 67 | 2-{4-[(Z)-3-(3,3-Bis-fluoromethyl pyrrolidin-1-yl)propenyl]phenyl}-3-(3-hydroxyphenyl)-4-methyl-2H-chromen-6-ol | (CDCl$_3$ + CD$_3$OD, 400 MHz); 1.55-1.64 (br t, 2H); 2.05 (s, 3H); 2.40 (s, 2H); 2.53-2.62 (br t, 2H); 3.25-3.32 (m, 2H); 4.18-4.28 (m, 2H); 4.31-4.42 (m, 2H); 5.68 (dt, J$_1$ = 11.88 Hz, J$_2$ = 6.48 Hz, 1H); 5.83 (s, 1H); 6.40 (d, J = 11.72 Hz, 1H); 6.53-6.64 (m, 3H); 6.65-6.70 (m, 2H); 6.77 (d, J = 2.68 Hz, 1H); 7.03 (d, J = 8.12 Hz, 2H); 7.12 (t, J = 7.84 Hz, 1H); 7.23 (d, J = 8.20 Hz, 2H); two exchangeable protons |

TABLE 2-continued

| Comp # | Chemical name | NMR |
|---|---|---|
| 68 | 2,2-Dimethylpropionic acid-3-(6-(2,2-dimethylpropionyloxy)-2-{4-[(E)-3-(10-fluorodecylamino)propenyl]phenyl}-4-methyl-2H-chromen-3-yl)phenyl ester. | (d$_6$-DMSO, 400 MHz); 1.25-1.42 (m, 30H); 1.53-1.74 (br m, 4H); 2.13 (s, 3H); 2.86 (t, J = 7.08 Hz, 2H); 3.67 (d, J = 6.88 Hz, 2H); 4.43 (dt, J$_1$ = 47.54 Hz, J$_2$ = 6.12 Hz, 2H); 6.22-6.31 (m, 2H); 6.73 (d, J = 16.05 Hz, 1H); 6.80 (d, J = 8.64 Hz, 1H); 6.90 (dd, J$_1$ = 8.64 Hz, J$_2$ = 2.68 Hz, 1H); 7.06-7.28 (m, 4H); 7.37 (d, J = 8.28 Hz, 2H); 7.41 (d, J = 8.40 Hz, 2H); 7.46 (t, J = 7.96 Hz, 1H); one exchangeable proton |
| 69 | 2-(4-{3-[(10,10-Difluoro decyl)methyl amino]propl-ynyl}phenyl)-3-(3-hydroxyphenyl)-4-methyl-2H-chromen-6-ol | (d$_6$-DMSO + Acetic acid, 400 MHz); 1.26-1.34 (br s, 10H); 1.34-1.50 (m, 4H); 1.74-1.92 (m, 2H); 2.08 (s, 3H); 2.31 (s, 3H); 2.46 (t, J = 7.28 Hz, 2H); 3.60 (s, 2H); 5.98 (s, 1H); 6.08 (tt, J$_1$ = 56.94 Hz, J$_2$ = 4.52 Hz, 1H); 6.54-6.60 (br s, 2H); 6.67-6.83 (m, 4H); 7.20 (t, J = 7.88 Hz, 1H); 7.32 (d, J = 8.48 Hz, 2H); 7.36 (d, J = 8.40 Hz, 2H); two exchangeable protons |
| 70 | 2-(4-{(E)-3-[(9,9-Difluorononyl)methy lamino]propenyl}phenyl)-3-(3-hydroxyphenyl)-4-methyl-2H-chromen-6-ol | (d$_6$-DMSO + Acetic acid, 400 MHz); 1.22-1.47 (m, 10H); 1.52-1.63 (m, 2H); 1.73-1.90 (br m, 2H); 2.09 (s, 3H); 2.79 (t, J = 7.24 Hz, 2H); 3.60 (d, J = 7.44 Hz, 2H); 5.97 (s, 1H); 6.08 (tt, J$_1$ = 56.94 Hz, J$_2$ = 4.44 Hz, 1H); 6.31 (dt, J$_1$ = 15.85 Hz, J$_2$ = 7.04 Hz, 1H); 6.56 (s, 2H); 6.65-6.83 (m, 5H); 7.19 (t, J = 7.72 Hz, 1H); 7.32 (d, J = 8.28 Hz, 2H); 7.41 (d, J = 8.28 Hz, 2H); three protons are merged between 2.50-2.70, two exchangeable protons |
| 71 | 2-(4-{(Z)-3[(9,9-Difluorononyl)methylamino]propenyl}phenyl)-3-(3-hydroxyphenyl)-4-methyl-2H-chromen-6-ol | (d$_6$-DMSO + Acetic acid, 400 MHz); 1.20-1.45 (m, 10H); 1.45-1.56 (m, 2H); 1.75-1.90 (br m, 2H); 2.09 (s, 3H); 2.47 (s, 3H); 2.70 (t, J = 7.72 Hz, 2H); 3.66 (d, J = 5.72 Hz, 2H); 5.78 (dt, J$_1$ = 11.92 Hz, J$_2$ = 6.12 Hz, 1H); 6.00 (s, 1H); 6.08 (tt, J$_1$ = 56.94 Hz, J$_2$ = 4.36 Hz, 1H); 6.54-6.60 (m, 2H); 6.64 (d, J = 11.84 Hz, 1H); 6.70-6.83 (m, 4H); 7.18 (d, J = 7.72 Hz, 1H); 7.22 (d, J = 8.04 Hz, 2H); 7.35 (d, J = 8.12 Hz, 2H); two exchangeable protons |
| 72 | 2-{4-[(Z)-3-((R)-3-Hydroxymethyl pyrrolidin-1-yl)propenyl]phenyl}-3-(3-hydroxyphenyl)-4-methyl-2H-chromen-6-ol | (d$_6$-DMSO + Acetic acid, 400 MHz); 1.58-1.69 (m, 1H); 1.95-2.05 (m, 1H); 2.10 (s, 3H); 2.38-2.47 (m, 1H); 2.84-2.92 (m, 1H); 3.07-3.16 (m, 2H); 3.32-3.46 (m, 2H); 3.88-3.97 (m, 2H); 5.80 (dt, J$_1$ = 11.68 Hz, J$_2$ = 6.60 Hz, 1H); 6.01 (s, 1H); 6.54-6.61 (m, 2H); 6.64 (d, J = 12.24 Hz, 1H); 6.70-6.77 (m, 2H); 6.77-6.83 (m, 2H); 7.17-7.27 (m, 3H); 7.36 (d, J = 8.16 Hz, 2H); one proton is merged between 3.16-3.25; three exchangeable protons |
| 73 | Acetic acid 3-(6-acetoxy-4-methyl-2-{4-[(Z)-3-((R)-3-methyl pyrrolidin-1-yl)-propenyl]phenyl}-2H-chromen-3-yl)phenyl ester | (d$_6$-DMSO + Acetic acid, 400 MHz); 1.03 (d, J = 6.60 Hz, 3H); 1.27-1.32 (br s, 1H); 1.42-1.53 (m, 1H); 2.13 (s, 3H); 2.30 (s, 3H); 2.31 (s, 3H); 2.63-2.69 (m, 1H); 3.15-3.21 (m, 2H); 3.75-4.10 (m, 2H); 5.79 (dt, J$_1$ = 12.00 Hz, J$_2$ = 5.92 Hz, 1H); 6.28 (s, 1H); 6.60-6.70 (m, 1H); 6.81 (d, J = 8.56 Hz, 1H); 6.92-6.96 (m, 1H); 7.10-7.15 (m, 1H); 7.18-7.21 (m, 1H); 7.21-7.28 (m, 3H); 7.29-7.34 (m, 1H); 7.38-7.50 (m, 3H); two protons are merged between 2.50-2.60 |
| 74 | Acetic acid-3-(6-acetoxy-2-{4-[(E)-3-(9-fluorononyl amino)propenyl]phenyl}-4-methyl-2H-chromen-3-yl)phenyl ester | (d$_6$-DMSO + Acetic acid, 400 MHz); 1.23-1.37 (m, 10H); 1.54-1.74 (m, 4H); 2.12 (s, 3H); 2.30 (s, 3H); 2.31 (s, 3H); 2.91 (t, J = 7.72 Hz, 2H); 3.72 (d, J = 6.80 Hz, 2H); 4.47 (dt, J$_1$ = 47.54 Hz, J$_2$ = 6.08 Hz, 2H); 6.20-6.30 (m, 2H); 6.76 (d, J = 16.01 Hz, 1H); 6.80 (d, J = 8.60 Hz, 1H); 6.93 (dd, J$_1$ = 8.64 Hz, J$_2$ = 2.64 Hz, 1H); 7.11 (dd, J$_1$ = 7.76 Hz, J$_2$ = 1.56 Hz, 1H); 7.17-7.21 (br m, 2H); 7.28 (d, J = 7.88 Hz, 1H); 7.37 (d, J = 8.32 Hz, 2H); 7.41 (d, J = 8.40 Hz, 2H); 7.45 (t, J = 7.88 Hz, 1H); one exchangeable proton |
| 75 | 3-(3-Hydroxyphenyl)-4-methyl-2-{4-[(Z)-3-((R)-3-methylpyrrolidin-l-yl)propenyl]phenyl}-2H-chromen-6-ol Isomer B | (d$_6$-DMSO, 400 MHz); 0.96 (d, J = 6.60 Hz, 3H); 1.25-1.37 (br s, 1H); 1.89-2.00 (br s, 1H); 2.04 (s, 3H); 2.13-2.34 (br s, 2H); 2.60-2.85 (br d, 2H); 2.85-3.02 (br s, 1H); 3.45-3.65 (br s, 2H); 5.73 (dt, J$_1$ = 12.25 Hz, J$_2$ = 6.30 Hz, 1H); 5.93 (s, 1H); 6.40-6.55 (m, 3H); 6.63-6.70 (s merged with d, 2H); 6.72 (d, J = 7.70 Hz, 1H); 6.75 (d, J = 2.35 Hz, 1H); 7.13 (t, J = 7.80 Hz, 1H); 7.16 (d, J = 8.30 Hz, 2H); 7.29 (d, J = 8.15 Hz, 2H); 8.98 (s, 1H); 9.47 (s, 1H) |
| 76 | 3-(3-Hydroxyphenyl)-4-methyl-2-{4-[(Z)-3-((R)-3-methylpyrrolidin-l-yl)propenyl]phenyl}-2H-chromen-6-ol Isomer A | (d$_6$-DMSO, 400 MHz); 0.98 (d, J = 6.70 Hz, 3H); 1.35-1.47 (br s, 1H); 1.93-2.01 (br s, 1H); 2.04 (s, 3H); 2.20-2.30 (br s, 1H); 2.45-2.55 (br s, 1H); 2.80-3.10 (br s, 2H); 3.10-3.25 (br s, 1H); 3.71-3.91 (br s, 2H); 5.77 (dt, J$_1$ = 12.20 Hz, J$_2$ = 6.25 Hz, 1H); 5.95 (s, 1H); 6.49-6.60 (m, 3H); 6.65-6.69 (s merged with d, 2H); 6.73 (d, J = 7.70 Hz, 1H); 6.75 (d, J = 2.40 Hz, 1H); 7.15 (t, J = 7.65 Hz, 1H); 7.18 (d, J = 8.20 Hz, 2H); 7.30 (d, J = 8.20 Hz, 2H); 9.00 (s, 1H); 9.49 (s, 1H) |
| 77 | 3-(3-Hydroxyphenyl)-4-methyl-2-{4-[(Z)-3-(4-methylpiperazin-1-yl)-propenyl]thenyl]-2H-chromen-6-ol Isomer B | (d$_6$-DMSO + Acetic acid, 400 MHz); 2.09 (s, 3H); 2.43 (s, 3H); 2.46-2.54 (br m, 4H); 2.65-2.78 (br m, 4H); 3.24-3.29 (br d, 2H); 5.73 (dt, J$_1$ = 11.94 Hz, J$_2$ = 6.26 Hz, 1H); 5.98 (s, 1H); 6.49 (d, J = 11.99 Hz, 1H); 6.52-6.60 (m, 2H); 6.66-6.83 (m, 4H); 7.15-7.24 (m, 3H); 7.33 (d, J = 8.17 Hz, 2H); two exchangeable protons |
| 78 | 3-(3-Hydroxyphenyl)-4-methyl-2-{4-[(Z)-3-(4-methylpiperazin-1-yl)propenyl]phenyl}-2H-chromen-6-ol Isomer A | (d$_6$-DMSO + Acetic acid, 400 MHz); 2.09 (s, 3H); 2.49 (s, 3H); 2.74-2.88 (br m, 4H); 3.24-3.32 (m, 2H); 5.73 (dt, J$_1$ = 12.08 Hz, J$_2$ = 5.96 Hz, 1H); 6.04 (s, 1H); 6.50 (d, J = 11.84 Hz, 1H); 6.55-6.59 (m, 2H); 6.70-6.83 (m, 2H); 7.11-7.26 (m, 5H); 7.30-7.37 (m, 2H); four protons are merged between 2.46-2.54; two exchangeable protons, |

TABLE 2-continued

| Comp # | Chemical name | NMR |
|---|---|---|
| 79 | 2-{4-[(E)-3-(9-Fluorononylamino)propenyl]phenyl}-3-(3-hydroxyphenyl)-4-methyl-2H-chromen-6-ol Isomer B | (d$_6$-DMSO + Acetic acid, 400 MHz); 1.31 (s, 10H); 1.56-1.65 (br m, 3H); 1.66-1.73 (br m, 1H); 2.09 (s, 3H); 2.88 (t, J = 7.56 Hz, 2H); 3.70 (d, J = 6.80 Hz, 2H); 4.46 (t, J$_1$ = 47.53 Hz, J$_2$ = 6.12 Hz, 2H); 5.98 (s, 1H); 6.26 (dt, J$_1$ = 15.92 Hz, J$_2$ = 6.96 Hz, 1H); 6.56 (s, 2H); 6.67-6.83 (m, 5H); 7.19 (t, J = 7.84 Hz, 1H); 7.33 (d, J = 8.32 Hz, 2H); 7.39 (d, J = 8.40 Hz, 2H); three exchangeable protons |
| 80 | 2-{4-[(E)-3-(9-Fluorononylamino)propenyl]phenyl}-3-(3-hydroxyphenyl)-4-methyl-2H-chromen-6-ol Isomer A | (d$_6$-DMSO + Acetic acid, 400 MHz); 1.31 (s, 10H); 1.56-1.65 (br m, 3H); 1.66-1.73 (br m, 1H); 2.09 (s, 3H); 2.88 (t, J = 7.56 Hz, 2H); 3.70 (d, J = 6.80 Hz, 2H); 4.46 (t, J$_1$ = 47.53 Hz, J$_2$ = 6.12 Hz, 2H); 5.98 (s, 1H); 6.26 (dt, J$_1$ = 15.92 Hz, J$_2$ = 6.96 Hz, 1H); 6.56 (s, 2H); 6.67-6.83 (m, 5H); 7.19 (t, J = 7.84 Hz, 1H); 7.33 (d, J = 8.32 Hz, 2H); 7.39 (d, J = 8.40 Hz, 2H); three exchangeable protons |
| 81 | 3-(3-Fluoro-5-hydroxyphenyl)-4-methyl-2-{4-[(Z)-3-((R)-3-methylpyrrolidin-1-yl)propenyl]phenyl}-2H-chromen-6-ol | (d$_6$-DMSO + Acetic acid, 400 MHz); 1.02 (d, J = 6.68 Hz, 3H); 1.38-1.49 (m, 1H); 1.98-2.09 (m, 1H); 2.11 (s, 3H); 2.23-2.34 (m, 1H); 2.41-2.51 (m, 1H); 2.89-3.04 (m, 2H); 3.09-3.17 (m, 1H); 3.51-3.59 (m, 2H); 5.77-5.84 (m, 1H); 6.02 (s, 1H); 6.51-6.67 (m, 6H); 6.82 (s, 1H); 7.23 (d, J = 8.20 Hz, 2H); 7.35 (d, J = 8.16 Hz, 2H); two exchangeable protons |
| 82 | 3-(3-Fluoro-5-hydroxyphenyl)-4-methyl-2-4-[(Z)-3-(4-methylpiperazin-1-yl)propenyl]phenyl}-2H-chromen-6-ol | (d$_6$-DMSO + Acetic acid, 400 MHz) 2.10 (s, 3H); 2.31 (s, 3H); 3.20-3.26 (br m, 2H); 5.74 (dt, J$_1$ = 11.96 Hz, J$_2$ = 6.16 Hz, 1H); 5.99 (s, 1H); 6.44-6.66 (m, 6H); 6.79-6.84 (m, 1H); 7.22 (d, J = 8.20 Hz, 2H); 7.33 (d, J = 8.20 Hz, 2H); eight protons are merged between 2.40-2.70, two exchangeable protons |
| 83 | 3-(3,5-Difluorophenyl)-4-methyl-2-{4-[(Z)-3-(4-methylpiperazin-1-yl)propenyl]phenyl}-2H-chromen-6-ol | (d$_6$-DMSO + Acetic acid, 400 MHz) 1.99 (s, 3H); 2.19-2.23 (m, 5H); 2.30-2.60 (br m, 6H); 3.17 (d, J = 6.56 Hz, 2H); 5.64 (dt, J$_1$ = 11.88 Hz, J$_2$ = 6.44 Hz, 1H); 5.78 (s, 1H); 6.44-6.53 (m, 3H); 6.68-6.80 (m, 4H); 7.04 (d, J = 8.16 Hz, 2H); 7.18 (d, J = 8.16 Hz, 2H); one exchangeable proton |
| 84 | 3-(3-Hydroxyphenyl)-2-{4-[(E)-3-(4-{2-[2-(2-methoxyethoxy)ethoxy]ethyl}piperazin-1-yl)propenyl]phenyl}-4-methyl-2H-chromen-6-ol | (d$_6$-DMSO + Acetic acid, 400 MHz) 2.09 (s, 3H); 2.57-2.70 (m, 4H); 3.12-3.22 (br m, 2H); 3.26 (s, 3H); 3.43-3.49 (m, 4H); 3.52-3.62 (m, 8H); 5.94 (s, 1H); 6.27 (dt, J$_1$ = 15.81 Hz, J$_2$ = 6.72 Hz, 1H); 6.48-6.52 (m, 1H); 6.52-6.58 (m, 2H); 6.67-6.78 (m, 3H); 6.79-6.82 (m, 1H); 7.19 (d, J = 7.84 Hz, 1H); 7.28 (d, J = 8.12 Hz, 2H); 7.36 (d, J = 8.28 Hz, 2H); six protons are merged between 2.50-2.57; two exchangeable protons |
| 85 | 3-(3-Hydroxyphenyl)-2-{4-[(Z)-3-({2-[2-(2-methoxyethoxy)ethoxy]ethyl}-methylamino)propenyl]phenyl}-4-methyl-2H-chromen-6-ol | (d$_6$-DMSO + Acetic acid, 400 MHz) 2.08-2.19 (m, 3H); 2.49 (s, 3H); 3.29 (s, 3H); 3.43-3.68 (m, 6H); 3.68-3.3.83 (m, 4H); 4.05-4.18 (m, 2H); 5.70-5.80 (m, 1H); 6.02-6.14 (br s, 1H); 6.53-7.03 (m, 8H); 7.16-7.29 (in, 2H); 7.29-7.44 (m, 2H); two protons are merged between 3.30-3.43 two exchangeable protons |
| 86 | 2-[2-Fluoro-4-((Z)-3-pyrrolidin-1-ylpropenyl)phenyl]-3-(3-hydroxyphenyl)-4-methyl-2H-chromen-6-ol | (d$_6$-DMSO + Acetic acid, 400 MHz) 1.82-1.90 (br m, 4H); 2.12 (s, 3H); 2.97-3.06 (br m, 4H); 3.88 (d, J = 6.04 Hz, 2H); 5.87 (dt, J$_1$ = 12.00 Hz, J$_2$ = 6.24 Hz, 1H); 6.26 (s, 1H); 6.54-6.59 (m, 2H); 6.60 (d, J = 12.08 Hz, 1H); 6.69-6.87 (in, 4H); 7.02-7.08 (in, 1H); 7.14-7.24 (m, 2H); 7.34 (t, J = 7.88 Hz, 1H); two exchangeable protons. |
| 87 | 2-[2-Fluoro-4-(3-pyrrolidin-1-ylprop-1-ynyl)phenyl]-3-(3-hydroxyphenyl)-4-methyl-2H-chromen-6-ol | (d$_6$-DMSO + Acetic acid, 400 MHz)1.71-1.84 (br m, 4H); 2.11 (s, 3H); 2.64-2.78 (br m, 4H); 3.72 (s, 2H); 6.23 (s, 1H); 6.54-6.59 (m, 2H); 6.66-6.79 (m, 3H); 6.82-6.86 (m, 1H); 7.15-7.23 (m, 2H); 7.27-7.35 (m, 2H); two exchangeable protons. |
| 88 | 1-(3-{4-[6-Fluoromethoxy-3-(3-fluoromethoxyphenyl)-4-methyl-2H-chromen-2-yl]phenyl}prop-2-ynyl)pyrrolidine | (d$_6$-DMSO + Acetic acid, 400 MHz) 1.72-1.79 (m, 4H); 2.14 (s, 3H); 2.59-2.66 (m, 4H); 3.64 (s, 2H); 5.79-5.82 (m, 1H); 5.86 (dd, J$_1$ = 12.15 Hz, J$_2$ = 3.35 Hz, 1H); 5.90-5.93 (m, 1H); 5.96 (dd, J$_1$ = 12.30 Hz, J$_2$ = 3.35 Hz, 1H); 6.21 (s, 1H); 6.78 (d, J = 8.70 Hz, 1H) 6.95 (dd J$_1$ = 8.65 Hz, J$_2$ = 2.85 Hz, 1H); 7.07-7.12 (m, 3H); 7.15 (d, J = 2.85 Hz, 1H); 7.35 (d, J = 6.35 Hz, 2H); 7.37 (d, J = 6.35 Hz, 2H); 7.42 (t, J = 8.10 Hz, 1H). |

In-Vitro Cell Line Assay

MCF-7 Cell Growth Inhibition Assay

MCF-7 cells were plated in 96 well plate in the presence of estradiol (1 nM) and incubated overnight. After 24 hours test compound was added at various concentrations and incubated for five days. On the fifth day, cell viability was evaluated using Presto Blue Cell Viability Reagent. Percentage growth inhibition was calculated as follows: 100−[(O.D. of sample)*100/O.D. of vehicle control] wherein O.D. is optical density.

Compounds of Formula I mostly showed growth inhibition more than 50% at 3 micromolar concentrations.

Table 3 provides % inhibition at 1 µM in MCF-7 cell growth inhibition assay for some of the representative compounds.

TABLE 3

% Inhibition at 1 µM in MCF-7 cell growth inhibition assay

| Comp # | % inhibition |
|---|---|
| 1 | 64.1 |
| 2 | 62.2 |
| 3 | 68.5 |
| 4 | 56.2 |
| 5 | 47.7 |
| 6 | 55.5 |

TABLE 3-continued

% Inhibition at 1 μM in MCF-7 cell growth inhibition assay

| Comp # | % inhibition |
|---|---|
| 7 | 85.3 |
| 8 | 59.1 |
| 9 | 79.8 |
| 10 | 52.3 |
| 11 | 65.1 |
| 12 | 57.6 |
| 13 | 5.5 |
| 14 | 79.1 |
| 15 | 52.2 |
| 16 | 56.7 |
| 17 | 43.4 |
| 18 | 51.3 |
| 19 | 29.4 |
| 20 | 15.4 |
| 21 | 60.1 |
| 22 | 29 |
| 23 | 36.8 |
| 24 | 62.5 |
| 25 | 42.5 |
| 26 | 55.2 |
| 27 | 28.8 |
| 28 | 55.9 |
| 29 | 12.97 |
| 30 | 19.1 |
| 31 | 19.9 |
| 32 | 27.4 |
| 33 | 22.8 |
| 34 | 35 |
| 35 | 68.6 |
| 36 | 38.8 |
| 37 | 57.2 |
| 38 | 49.9 |
| 39 | 89.7 |
| 40 | 29.3 |
| 41 | 77.6 |
| 42 | 62 |
| 43 | 47.9 |
| 44 | 67.2 |
| 45 | 71.4 |
| 46 | 88.6 |
| 47 | 67.4 |
| 48 | 58.9 |
| 49 | 67.3 |
| 50 | 57.3 |
| 51 | 61.1 |
| 52 | 74.3 |
| 53 | 38.6 |
| 54 | 67.5 |
| 55 | 67.1 |
| 56 | 44.9 |
| 57 | 24.3 |
| 58 | 37.9 |
| 59 | 73.5 |
| 60 | 55 |
| 61 | 39.3 |
| 62 | 53.1 |
| 63 | 41.8 |
| 64 | 47.2 |
| 65 | 55.4 |
| 66 | 12.9 |
| 67 | 30.1 |
| 69 | 19.8 |
| 70 | 16.9 |
| 71 | 56.8 |
| 72 | 31.9 |
| 75 | 74.4 |
| 76 | 67.5 |
| 77 | 46 |
| 79 | 64.8 |
| 80 | 53 |
| 81 | 77.4 |
| 82 | 46.8 |
| 83 | 12.9 |

The invention claimed is:

1. A method of inhibiting the action of endogenous estrogen in estrogen receptor positive breast cancer comprising administering a compound of Formula I to a human:

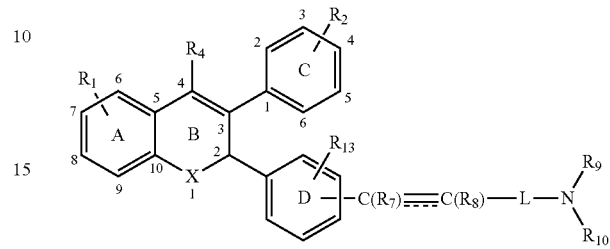

Formula I or salts or stereoisomers thereof wherein, $R_1$ is mono or di-substitution on ring A and is selected from a group consisting of, —$OR_3$, halogen, —$C_{1-6}$ haloalkyl, —$OC_{1-6}$ haloalkyl, —CN, —$N(R_3)_2$, —$NR_3SO_2R_3$, —$NR_3CHO$, —$NR_3COR_3$, —$OC(O)R_3$, —$OC(O)N(R_3)_2$, —$OP(O)(OH)_2$ and —$OC(O)OR_3$ wherein $R_3$ at each occurrence is selected from hydrogen, $C_{1-6}$ linear, branched or cyclic alkyl and $C_{1-6}$ linear, branched or cyclic haloalkyl;

$R_2$ is mono or di-substitution and is a halogen;

$R_4$ is selected from hydrogen and —$C_{1-5}$ alkyl;

L is selected from $C_{1-7}$ linear or branched alkyl;

$R_7$ and $R_8$ are absent or independently selected from hydrogen and $C_{1-5}$ alkyl;

$R_9$ and $R_{10}$ together with the nitrogen atom to which they are attached forms a 4 to 5 membered ring optionally containing 1 to 2 additional heteroatoms selected from oxygen, nitrogen or sulfur and the ring is optionally substituted with one or more group selected from halogen, —$OR_6$, —$N(R_6)_2$ and $R_6$ wherein $R_6$, at each occurrence is selected from a group comprising hydrogen, $C_{1-20}$ linear, branched or cyclic alkyl optionally interrupted with one or more radicals independently selected from —O—, —$NR_5$—, —S—, —SO—, —$S(O)_2$—, —$CR_5$=$CR_5$—, —C≡C—, —$NR_5CO$—, —$CONR_5$—, —$NR_5CONR_5$—, $NR_5C(O)O$— and —OC(O)O—;

optionally, $R_6$ is further substituted with one or more groups selected from a group comprising halogen, —$OR_{12}$, —$N(R_{12})_2$, and —$COOR_{12}$, —$CON(R_{12})_2$ or —$CON(R_{12})OH$; wherein $R_{12}$ at each occurrence is selected from hydrogen or $C_{1-6}$ linear, branched or cyclic alkyl;

═ is a double or a triple bond;

$R_{13}$ is selected from a group comprising —$R_{14}$, —$OR_{14}$, halogen, —$C_{1-6}$ haloalkyl, —$OC_{1-6}$ haloalkyl, —CN, —$N(R_{14})_2$, —$NR_{14}SO_2R_{14}$, —$NR_{14}CHO$, —$NR_{14}COR_{14}$, —$OC(O)R_{14}$, —$OC(O)N(R_{14})_2$, —$OP(O)(OH)_2$ and —$OC(O)OR_{14}$ wherein $R_{14}$ at each occurrence is selected from hydrogen, and $C_{1-6}$ linear, branched or cyclic alkyl; and X is oxygen.

2. The method of claim 1 wherein the human has breast cancer.

3. The method of claim 1, wherein $R_1$ is a mono-substitution and is —OH;

$R_2$ is di-substitution;

$R_7$ and $R_8$ are hydrogen;

$R_{13}$ is $R_{14}$, and $R_{14}$ is hydrogen;

$R_4$ is methyl;

L is $C_{1-3}$ linear alkyl; and $R_9$ and $R_{10}$ together with the nitrogen atom to which they are attached forms a 4-5 membered ring wherein the ring is substituted with $R_6$; wherein $R_6$ is selected from $C_{1-3}$ linear alkyl and wherein $R_6$ is further substituted with halogen; and = is a double bond.

4. The method of claim 3, wherein $R_2$ is fluoro.

5. A method of treating breast cancer comprising administering a compound of Formula I to a human having the disease:

Formula I

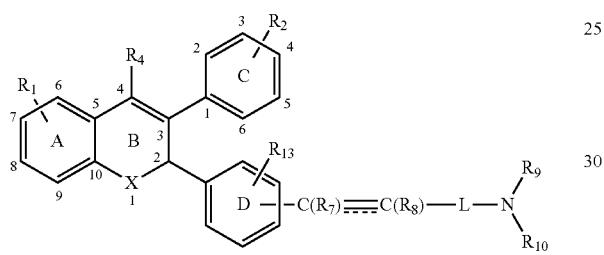

or salts or stereoisomers thereof wherein, $R_1$ is mono or di-substitution on ring A and is selected from a group consisting of, —$OR_3$, halogen, —$C_{1-6}$ haloalkyl, —$OC_{1-6}$ haloalkyl, —CN, —$N(R_3)_2$, —$NR_3SO_2R_3$, —$NR_3CHO$, —$NR_3COR_3$, —OC(O)$R_3$, —OC(O)N($R_3$)$_2$, —OP(O)(OH)$_2$ and —OC(O)OR$_3$ wherein $R_3$ at each occurrence is selected from hydrogen, $C_{1-6}$ linear, branched or cyclic alkyl and $C_{1-6}$ linear, branched or cyclic haloalkyl;

$R_2$ is mono or di-substitution and is a halogen;

$R_4$ is selected from hydrogen and —$C_{1-5}$ alkyl;

L is selected from $C_{1-7}$ linear or branched alkyl;

$R_7$ and $R_8$ are absent or independently selected from hydrogen and $C_{1-5}$ alkyl;

$R_9$ and $R_{10}$ together with the nitrogen atom to which they are attached forms a 4 to 5 membered ring optionally containing 1 to 2 additional heteroatoms selected from oxygen, nitrogen or sulfur; and the ring is optionally substituted with one or more group selected from halogen, —$OR_6$, —$N(R_6)_2$ and $R_6$ wherein $R_6$, at each occurrence is selected from a group comprising hydrogen, $C_{1-20}$ linear, branched or cyclic alkyl optionally interrupted with one or more radicals independently selected from —O—, —$NR_5$—, —S—, —SO—, —S(O)$_2$—, —$CR_5$=$CR_5$—, —C≡C—, —$NR_5CO$—, —$CONR_5$—, —$NR_5CONR_5$—, $NR_5C(O)O$— and —OC(O)O—;

optionally, $R_6$ is further substituted with one or more groups selected from a group comprising halogen, —$OR_{12}$, —$N(R_{12})_2$, and —$COOR_{12}$, —$CON(R_{12})_2$ or —$CON(R_{12})OH$; wherein $R_{12}$ at each occurrence is selected from hydrogen or $C_{1-6}$ linear, branched or cyclic alkyl;

= is a double or a triple bond;

$R_{13}$ is selected from a group comprising —$R_{14}$, —$OR_{14}$, halogen, —$C_{1-6}$ haloalkyl, —$OC_{1-6}$ haloalkyl, —CN, —$N(R_{14})_2$, —$NR_{14}SO_2R_{14}$, —$NR_{14}CHO$, —$NR_{14}COR_{14}$, —OC(O)$R_{14}$, —OC(O)N($R_{14}$)$_2$, —OP(O)(OH)$_2$ and —OC(O)OR$_{14}$ wherein $R_{14}$ at each occurrence is selected from hydrogen, and $C_{1-6}$ linear, branched or cyclic alkyl; and X is oxygen.

6. The method of claim 5, wherein $R_1$ is a mono-substitution and is —OH;

$R_2$ is di-substitution;

$R_7$ and $R_8$ are hydrogen;

$R_{13}$ is $R_{14}$, and $R_{14}$ is hydrogen;

$R_4$ is methyl;

L is $C_{1-3}$ linear alkyl; and $R_9$ and $R_{10}$ together with the nitrogen atom to which they are attached forms a 4-5 membered ring wherein the ring is substituted with $R_6$; wherein $R_6$ is selected from $C_{1-3}$ linear alkyl and wherein $R_6$ is further substituted with halogen; and = is a double bond.

7. The method of claim 6, wherein $R_2$ is fluoro.

8. A method of inhibiting breast cancer cell growth comprising administering a compound of Formula I to a human:

Formula I

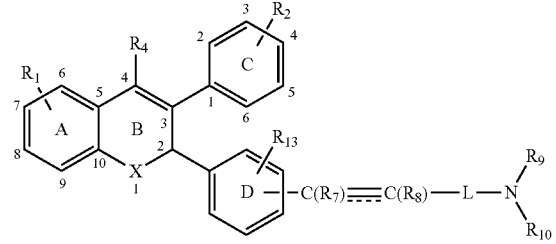

or salts or stereoisomers thereof wherein, $R_1$ is mono or di-substitution on ring A and is selected from a group consisting of, —$OR_3$, halogen, —$C_{1-6}$ haloalkyl, —$OC_{1-6}$ haloalkyl, —CN, —$N(R_3)_2$, —$NR_3SO_2R_3$, —$NR_3CHO$, —$NR_3COR_3$, —OC(O)$R_3$, —OC(O)N($R_3$)$_2$, —OP(O)(OH)$_2$ and —OC(O)OR$_3$ wherein $R_3$ at each occurrence is selected from hydrogen, $C_{1-6}$ linear, branched or cyclic alkyl and $C_{1-6}$ linear, branched or cyclic haloalkyl;

$R_2$ is mono or di-substitution and is a halogen;

$R_4$ is selected from hydrogen and —$C_{1-5}$ alkyl;

L is selected from $C_{1-7}$ linear or branched alkyl;

$R_7$ and $R_8$ are absent or independently selected from hydrogen and $C_{1-5}$ alkyl;

$R_9$ and $R_{10}$ together with the nitrogen atom to which they are attached forms a 4 to 5 membered ring optionally containing 1 to 2 additional heteroatoms selected from oxygen, nitrogen or sulfur; and the ring is optionally substituted with one or more group selected from halogen, —$OR_6$, —$N(R_6)_2$ and $R_6$ wherein $R_6$, at each occurrence is selected from a group comprising hydrogen, $C_{1-20}$ linear, branched or cyclic alkyl optionally interrupted with one or more radicals independently selected from —O—, —$NR_5$—, —S—, —SO—, —$S(O)_2$—, —$CR_5$=$CR_5$—, —C≡C—, —$NR_5CO$—, —$CONR_5$—, —$NR_5CONR_5$—, $NR_5C(O)O$— and —$OC(O)O$—;

optionally, $R_6$ is further substituted with one or more groups selected from a group comprising halogen, —$OR_{12}$, —$N(R_{12})_2$, and —$COOR_{12}$, —$CON(R_{12})_2$ or —$CON(R_{12})OH$; wherein $R_{12}$ at each occurrence is selected from hydrogen or $C_{1-6}$ linear, branched or cyclic alkyl;

= is a double or a triple bond;

$R_{13}$ is selected from a group comprising —$R_{14}$, —$OR_{14}$, halogen, —$C_{1-6}$ haloalkyl, —$OC_{1-6}$ haloalkyl, —CN, —$N(R_{14})_2$, —$NR_{14}SO_2R_{14}$, —$NR_{14}CHO$, —$NR_{14}COR_{14}$, —$OC(O)R_{14}$, —$OC(O)N(R_{14})_2$, —$OP(O)(OH)_2$ and —$OC(O)OR_{14}$ wherein $R_{14}$ at each occurrence is selected from hydrogen, and $C_{1-6}$ linear, branched or cyclic alkyl; and X is oxygen.

9. The method of claim 8 wherein the human has breast cancer.

10. The method of claim 8, wherein $R_1$ is a mono-substitution and is —OH;

$R_2$ is di-substitution;

$R_7$ and $R_8$ are hydrogen;

$R_{13}$ is is $R_{14}$, and $R_{14}$ hydrogen;

$R_4$ is methyl;

L is $C_{1-3}$ linear alkyl; and $R_9$ and $R_{10}$ together with the nitrogen atom to which they are attached forms a 4-5 membered ring wherein the ring is substituted with $R_6$; wherein $R_6$ is selected from $C_{1-3}$ linear alkyl and wherein $R_6$ is further substituted with halogen; and = is a double bond.

11. The method of claim 10, wherein $R_2$ is fluoro.

* * * * *